United States Patent [19]
Aono et al.

[11] Patent Number: 5,506,267
[45] Date of Patent: Apr. 9, 1996

[54] THIOGLYCEROL DERIVATIVES

[75] Inventors: Tetsuya Aono, Nagaokakyo; Koichi Yukishige, Takatsuki; Seiichi Tanida, Nagaokakyo, all of Japan

[73] Assignee: Takeda Chemical Industries, Ltd., Osaka, Japan

[21] Appl. No.: 302,337

[22] Filed: Sep. 8, 1994

[30] Foreign Application Priority Data

Sep. 8, 1993 [JP] Japan .................................. 5-223669
Jan. 21, 1994 [JP] Japan .................................. 6-005320

[51] Int. Cl.$^6$ ................................................. A61K 31/16
[52] U.S. Cl. .................. 514/616; 514/618; 514/706; 514/709; 554/48; 554/56; 554/57; 554/85; 554/101
[58] Field of Search ................... 554/48, 56, 57, 554/85, 101; 814/616, 618, 706, 709

[56] References Cited

U.S. PATENT DOCUMENTS 4,666,886  5/1987  Baschang et al. .................... 514/17

FOREIGN PATENT DOCUMENTS

| | | |
|---|---|---|
| 014815 | 9/1980 | European Pat. Off. . |
| 0000330 | 8/1981 | European Pat. Off. . |
| 0210412 | 2/1987 | European Pat. Off. . |
| 0548024 | 6/1993 | European Pat. Off. . |
| 4-9397 | 1/1992 | Japan . |
| 4-46194 | 2/1992 | Japan . |
| 4-99796 | 3/1992 | Japan . |

OTHER PUBLICATIONS

Branch et al, Chemical Abstract of EP–572,909, 121:109667, 1993.
Morishima et al, Chemical Abstracts, 114:144034, 1990.
Metzger et al., Int. J. Peptide Protein Res., "Synthesis of $N_\alpha$–Fmoc protected derivatives of S–(2,3–dihydroxyproply-)–cysteine and their application in peptide synthesis", vol. 38, No. 6, pp. 545–554 (1991).
Chem. Pharm. Bull., "Synthesis of Optically Active Lipopeptide Analogs from the Outer Membrane of *Escherichia coli*" Kurimura et al., 39 (10), pp. 2590–2596 (1991).
Chem. Pharm. Bull., "Synthesis and Mitogenic Activity of Chiral Lipopeptide WS1279 and Its Derivatives" Kurimura et al., 41 (11), pp. 1965–1970 (1993).
Chem. Pharm. Bull., "Synthesis of Biologically Active Pentapeptide Analogs of the N–Terminal Part of Lipoprotein From the Outer Membrane of *Escherichia coli*" Kurimura et al., 38 (4), pp. 1110–1112 (1990).
Peptide Chemistry 1990: Y. Shimonishi (Ed.), Protein Research Foundation, Osaka, Japan (1990), "Synthesis and Mitogenic Activity of Lipopeptide and Its Analogs" Kurimura et al., pp. 37–42.
Peptide Chemistry 1991: A. Suzuki (Ed.) Protein Research Foundation, Osaka, Japan (1991), "Stereospecific Synthesis and Mitogenic Activity of Lipopeptide WS 1279 and Its Derivatives" Kurimura et al., pp. 361–366.
Int. J. Peptide Protein Res., "Synthesis of Novel Immunologically Active Tripalmitoyl–S–Glycerylcysteinyl Lipopeptides as Useful Intermediates for Immunogen Preparations" Metzger et al., 37, 1991, pp. 46–57.

*Primary Examiner*—José G. Dees
*Assistant Examiner*—Deborah D. Carr
*Attorney, Agent, or Firm*—Wenderoth, Lind & Ponack

[57] ABSTRACT

A compound of the invention is represented by the formula:

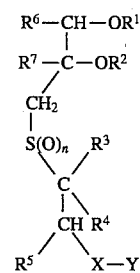

wherein $R^1$ and $R^2$ are the same or different, an acyl group; $R^3$, $R^4$, $R^6$ and $R^7$ are the same or different, hydrogen or an alkyl group; $R^5$ is hydrogen, an alkyl group or a hydroxyl group which may optionally be protected, or $R^4$ and $R^5$ are combined to form a chemical bond; X is a carbonyl group or a sulfonyl group; Y is an amino acid sequence consisting of 1 to 7 amino acid residues which may optionally be protected and having optionally an intervening —$SO_2NH$—; n is an integer of 0 to 2, or a salt thereof.

The compound or salt thereof of the present invention possesses immunoenhancing activity and platelet reduction recovery activity, and can be used as a prophylactic/therapeutic agent for leukocytopenia in cancer chemotherapy or radiotherapy, as an immunoenhancing agent in bone marrow transplantation therapy and the treatment of osteomyelodysplasia and aplastic anemia, and as a prophylactic/therapeutic agent for thrombocytopenia.

18 Claims, No Drawings

THIOGLYCEROL DERIVATIVES

FIELD OF THE INVENTION

The present invention relates to a new thioglycerol derivative. With immunoenhancing and platelet increasing activity, the thioglycerol derivative of the present invention serves well as a prophylactic/therapeutic agent for various diseases such as leukocytopenia, which is caused by various causes, diseases resulting from leukocyte reduction, diseases therapeutically necessitating an increase in bone marrow cells or leukocytes, thrombocytopenia, diseases resulting from platelet reduction, and diseases therapeutically necessitating an increase in megakaryocytes or platelets.

BACKGROUND OF THE INVENTION

As a thioglycerol compound possessing leukocyte increasing activity, Japanese Patent Unexamined Publication No. 46194/1992 describes the substance WS-1279A, represented by the formula:

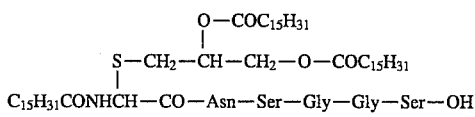

Synthesis of WS-1279A was reported by Tsuda et al. [Chemical Pharmaceutical Bulletin, Vol. 39, pp. 607–611 (1991)] and Achiwa et al. [Japanese Patent Unexamined Publication No. 99796/1992; Chemical Pharmaceutical Bulletin, Vol. 39, pp. 2590–2596 (1991); Peptide Chemistry, pp. 361–366 (1991)]. In addition, Japanese Patent Unexamined Publication Nos. 9224/1979, 139348/1984, 6410/1990 and 9397/1992, Japanese Patent Examined Publication No. 60760/1988 and other publications describe thioglycerol compounds, but none describes leukocyte increasing activity.

Chemotherapy or radiotherapy on cancer patients can cause severe leukocytopenia or thrombocytopenia. Leukocytopenia, which results in impaired resistance to infectious and other diseases, and thrombocytopenia, which results in hemostatic dysfunction, both pose a major therapeutic problem for which no satisfactory treatment is available. There is therefore a need for a drug that promotes recovery of leukocyte or platelet count. There is another need for a drug offering rapid recovery of leukocyte count in bone marrow transplantation therapy and the treatment of osteomyelodysplasia. This kind of drug can also be used in the fields of thrombocytopenia following bone marrow transplantation and autoimmune diseases associated with platelet reduction, such as aplastic anemia and idiopathic thrombocytopenic purpura.

With this situation in mind, the present inventors designed and synthesized various compounds and investigated their leukocyte and platelet reduction recovering activity. As a result, the inventors found that a thioglycerol derivative promotes bone marrow cell growth to increase the peripheral leukocyte count and hence enhance immunity in mice, and that mouse megakaryocyte growth and differentiation can be promoted by stimulating bone marrow cells. The inventors made further investigations based on these findings, and developed the present invention.

SUMMARY OF THE INVENTION

The present invention is to provide:

1) A compound represented by the formula [I]:

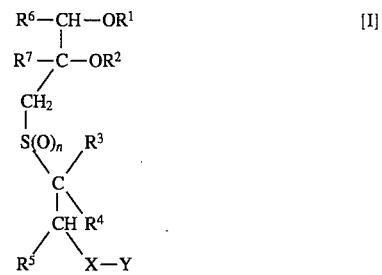

wherein $R^1$ and $R^2$ are the same or different, an acyl group; $R^3$, $R^4$, $R^6$ and $R^7$ are the same or different, hydrogen or an alkyl group; $R^5$ is hydrogen, an alkyl group or a hydroxyl group which may optionally be protected, or $R^4$ and $R^5$ are combined to form a chemical bond; X is a carbonyl group or a sulfonyl group; Y is an amino acid sequence consisting of 1 to 7 amino acid residues which may optionally be protected and having optionally an intervening —$SO_2NH$—; n is an integer of 0 to 2, or a salt thereof;

2) The compound according to 1), wherein $R^1$ and $R^2$ are the same or different, an acyl group; $R^3$ and $R^4$ are the same or different, hydrogen or an alkyl group; $R^5$, $R^6$ and $R^7$ are hydrogen, or $R^4$ and $R^5$ are combined to form a chemical bond; X is a carbonyl group or a sulfonyl group; Y is an amino acid sequence consisting of 1 to 7 amino acids residues which may optionally be protected and having optionally an intervening —$SO_2NH$—; n is 0;

3) The compound according to 1), wherein the acyl group is an aliphatic acyl group having 6 to 26 carbon atoms;

4) The compound according to 1), wherein the acyl group is an aliphatic acyl group having 10 to 20 carbon atoms;

5) The compound according to 1), wherein the acyl group is a substituted carbamoyl group;

6) The compound according to 5), wherein the substituent in the substituted carbamoyl group is an aliphatic hydrocarbon group having 4 to 24 carbon atoms;

7) The compound according to 1), wherein $R^3$ and $R^4$ are hydrogen;

8) The compound according to 1), wherein the amino acid sequence represented by Y consists of 1 to 5 amino acid residues;

9) The compound according to 1), wherein $R^5$ is hydrogen or an alkyl group having 1 to 4 carbon atoms;

10) The compound according to 1), wherein $R^6$ and $R^7$ are hydrogen;

11) The compound according to 1), wherein n is 0;

12) A compound according to 1), wherein the compound is 4-[6,7-bis( 12-phenyldodecanoyloxy)-4-thiaheptanoylaminomethyl]benzoyl-glutamic acid;

13) A compound according to 1), wherein the compound is 4-[6,7-bis(palmitoyloxy)- 4-thiaheptanoylamino]benzoyl-glutamic acid;

14) A compound according to 1), wherein the compound is 4-[6,7-bis( 12-phenyldodecanoyloxy)-4-thiaheptanoylamino]benzoyl-glutamic acid;

15) A compound according to 1), wherein the compound is 4-[6,7-bis(palmitoyloxy)- 4-thia-2(Z)-heptanoylaminomethyl]benzoyl-glutamic acid;

16) A compound according to 1), wherein the compound is 4-[6,7-bis(palmitoyloxy)- 2-methyl-4-thiaheptanoylamino]benzoyl-glutamic acid;

17) A compound according to 1), wherein the compound is 4-[6,7-bis(palmitoyloxy)- 4-thiaheptanoylamino] benzoylphenylalanine;

18) A composition for immuno-enhancement, which comprises or a salt thereof as defined in 1 ); and 19) A composition for preventing or treating thrombocytopenia, which comprises a compound or a salt thereof as defined in 1 ).

DETAILED DESCRIPTION OF THE INVENTION

With respect to general formulas [I] and [II] (described hereinafter), the acyl group represented by $R^1$ and $R^2$ include a substituted carbamoyl group and an aliphatic acyl group.

The substitutuent in the substituted carbamoyl group is preferably a straight-chain or branched, saturated or unsaturated hydrocarbon group. Such hydrocarbon groups include aliphatic hydrocarbon groups having 4 to 24 carbon atoms (e.g., straight-chain alkyl groups such as butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl, branched alkyl groups such as 3,7,11-trimethyldodecyl, 3,7,11,15-tetramethylhexadecyl and 12-cyclohexyldodecyl, alkenyl groups such as geranyl, farnesyl, geranylgeranyl and 4,8,12-trimethyl-3,7,11-tridecatrienyl). Of these substituents, one or two may substitute for the carbamoyl group.

The above-described substituent is more preferably an aliphatic hydrocarbon group having 8 to 22 carbon atoms (e.g., straight-chain alkyl groups such as octyl, nonyl, decyl, undecyl, dodecyl, tridecyl, tetradecyl, pentadecyl, hexadecyl, heptadecyl, octadecyl, nonadecyl and eicosyl, branched alkyl groups such as 3,7,11-trimethyldodecyl, 3,7,11,15-tetramethylhexadecyl and 12-cyclohexyldodecyl, alkenyl groups such as geranyl, farnesyl, geranylgeranyl and 4,8,12-trimethyl-3,7,11-tridecatrienyl).

The above-described substituent is still more preferably an aliphatic hydrocarbon group having 10 to 20 carbon atoms (e.g., straight-chain alkyl groups such as decyl, undecyl, dodecyl, tridecyl, tetradecyl, pentadecyl, hexadecyl, heptadecyl, octadecyl, nonadecyl and eicosyl, branched alkyl groups such as 3,7,11-trimethyldodecyl, 3,7,11,15-tetramethylhexadecyl and 12-cyclohexyldodecyl, alkenyl groups such as geranyl, farnesyl, geranylgeranyl and 4,8,12-trimethyl-3,7,11-tridecatrienyl).

The aliphatic acyl group is exemplified by saturated or unsaturated aliphatic acyl groups. The aliphatic acyl group is preferably an aliphatic acyl group having 6 to 26 carbon atoms (e.g., hexanoyl, heptanoyl, octanoyl, dodecanoyl, tridecanoyl, tetradecanoyl, pentadecanoyl, hexadecanoyl, heptadecanoyl, octadecanoyl, nonadecanoyl, nocosanoyl, tetracosanoyl, myristoleoyl, oleoyl, palmitoleoyl, etheidoyl, cis,cis-9,12-octadecadienoyl, 9,12,15-octadecatrienoyl, 9,11,13-octadecatrienoyl, 5,8,11,14-eicosatetraenoyl, cis-15-tetracosaenoyl).

The above-described acyl group is more preferably an aliphatic acyl group having 8 to 24 carbon atoms (e.g., octanoyl, dodecanoyl, tridecanoyl, tetradecanoyl, pentadecanoyl, hexadecanoyl, heptadecanoyl, octadecanoyl, nonadecanoyl, nocosanoyl, tetracosanoyl, myristoleoyl, oleoyl, palmitoleoyl, etheidoyl, cis,cis-9,12-octadecadienoyl, 9,12,15-octadecatrienoyl, 9,11,13-octadecatrienoyl, 5,8,11,14-eicosatetraenoyl, cis-15-tetracosaenoyl).

The above-described acyl group is still more preferably an aliphatic acyl group having 10 to 20 carbon atoms (e.g., dodecanoyl, tridecanoyl, tetradecanoyl, pentadecanoyl, hexadecanoyl, heptadecanoyl, octadecanoyl, nonadecanoyl, nocosanoyl, myristoleoyl, oleoyl, palmitoleoyl, etheidoyl, cis,cis-9,12-octadecadienoyl, 9,12,15-octadecatrienoyl, 9,11,13-octadecatrienoyl, 5,8,11,14-eicosatetraenoyl, cis-15-tetracosaenoyl).

The substituent in the above-described substituted carbamoyl group and aliphatic acyl group may further have a substituent. Such substituents include halogen atoms (e.g., fluorine, chlorine), cycloalkyl groups having 3 to 8 carbon atoms (e.g., cyclopropyl, cyclobutyl, cyclopentyl, cyclohexyl) and aryl groups having 6 to 14 carbon atoms (e.g., phenyl, biphenylyl, 1- or 2-naphthyl). The substituent is preferably a cycloalkyl group having 3 to 8 carbon atoms (e.g., cyclopropyl, cyclobutyl, cyclopentyl, cyclohexyl) or an aryl group having 6 to 14 carbon atoms (e.g., phenyl, biphenylyl, 1- or 2-naphthyl). The aryl group may have a substituent exemplified by alkyl groups having 1 to 6 carbon atoms (e.g., methyl, ethyl, propyl, isopropyl) and halogen atoms (e.g., fluorine, chlorine).

With respect to general formulas [I] and [r[] (described hereinafter), $R^1$ or $R^2$ is preferably a saturated or unsaturated aliphatic acyl group, more preferably an aliphatic acyl group having 10 to 20 carbon atoms which may be substituted by a cycloalkyl group having 3 to 8 carbon atoms (e.g., cyclopropyl, cyclobutyl, cyclopentyl, cyclohexyl) or an aryl group having 6 to 14 carbon atoms (e.g., phenyl, tolyl, xylyl, biphenylyl, 1- or 2-naphthyl).

With respect to general formulas [I], [II] and [IV] (described hereinafter), the alkyl group for $R^3$, $R^4$, $R^5$, $R^6$ or $R^7$ is preferably an alkyl group having 1 to 6 carbon atoms (e.g., methyl, ethyl, propyl, isopropyl, butyl, isobutyl, sec-butyl, pentyl, isopentyl, 1-ethylpropyl, hexyl, isohexyl). The alkyl group is more preferably an alkyl group having 1 to 4 carbon atoms (e.g., methyl, ethyl, propyl, isopropyl, butyl, isobutyl, sec-butyl). The alkyl group is still more preferably methyl or ethyl. The above-described alkyl group may have 1 to 4 substituents selected from (1) hydroxy, (2) amino, (3) carboxyl, (4) nitro, (5) mono- or di- $C_{1-6}$ alkylamino such as methylamino, ethylamino, propylamino, dimethylamino and diethylamino, (6) $C_{1-6}$ alkoxy such as methoxy, ethoxy, propoxy and hexyloxy, (7) $C_{1-6}$ alkylcarbonyloxy such as acetoxy and ethylcarbonyloxy, and (8) halogen such as fluorine, chlorine, bromine and iodine.

With respect to general formula [I], [II] and [IV] (described hereinafter), $R^5$ is preferably hydrogen or an alkyl group having 1 to 4 carbon atoms.

With respect to general formula [I] , $R^4$ and $R^5$ may be combined to form a chemical bond.

With respect to general formula [I], the protecting group for the hydroxyl group for $R^5$ which may be protected is exemplified by:

(1) alkoxycarbonyl groups having 2 to 7 carbon atoms such as methoxycarbonyl, ethoxycarbonyl, propoxycarbonyl and tert-butoxycarbonyl, which may have 1 to 4 substituents selected from halogen atoms such as chlorine, bromine and fluorine, aryl groups having 6 to 10 carbon atoms such as phenyl and naphthyl, aralkyl groups having 7 to 12 carbon atoms such as benzyl and phenylethyl, and the nitro group, (2) a formyl group, (3) alkanoyl groups having 2 to 7 carbon atoms such as acetyl and propionyl which may have 1 to 3 substituents selected from halogen atoms such as chlorine, bromine and fluorine, amino groups which may be protected (the protecting group exemplified by the same amino group protecting groups as specified below), aryl groups having 6 to 10 carbon atoms such as phenyl and naphthyl, and the nitro group, (4) aryl-oxycarbonyl groups having 7 to 11 carbon atoms such as phenyloxycarbonyl and naphthyloxycarbonyl which may have 1 to 4 substituents selected from halogen atoms such as chlorine, bromine and fluorine, alkyl groups having 1 to 6 carbon atoms such as methyl, ethyl, propyl and isopropyl, aryl groups having 6 to 10 carbon atoms such as phenyl and naphthyl, and the nitro group, (5) aryl carbonyl groups having 7 to 11 carbon atoms such as benzoyl and naphthylcarbonyl which may have 1 to 4 substituents selected from halogen atoms such as chlorine, bromine and fluorine, alkyl groups having 1 to 6 carbon atoms such as methyl, ethyl, propyl and isopropyl, aryl groups having to 10 carbon atoms such as phenyl and naphthyl, and the nitro group, (6) aralkyl-carbonyl groups having 8 to 13 carbon atoms such as benzylcarbonyl and phenethylcarbonyl which may have 1 to 4 substituents selected from halogen atoms such as chlorine, bromine and fluorine, alkyl groups having I to 6 carbon atoms such as methyl, ethyl, propyl and isopropyl, aryl groups having 6 to 10 carbon atoms such as phenyl and naphthyl, and the nitro group, (7) groups such as pyranyl and furanyl which may have 1 to 4 substituents selected from halogen atoms such as chlorine, bromine and fluorine, alkyl groups having 1 to 6 carbon atoms such as methyl, ethyl, propyl and isopropyl, aryl groups having 6 to 10 carbon atoms such as phenyl and naphthyl, aralkyl groups having 7 to 12 carbon atoms such as benzyl and phenylethyl, and the nitro group, and (8) tri-$C_{1-4}$ alkylsilyl groups such as trimethylsilyl and triethylsilyl.

The above-described protecting group is preferably an alkanoyl group having 2 to 7 carbon atoms such as acetyl or propionyl which may have 1 to 3 substituents selected from halogen atoms such as chlorine, bromine and fluorine, amino groups which may be protected (the protecting group exemplified by the same amino group protecting groups as specified below), aryl groups having 6 to 10 carbon atoms such as phenyl and naphthyl, and the nitro group.

With respect to general formulas [I], [II] and [IV], $R^6$ and $R^7$ are preferably hydrogen.

With respect to general formulas [I], [III] (described hereinafter) and [IV], the amino acids in the amino acid sequence for Y may be of the natural type or not.

Natural amino acids include amino acids obtained from nature as protein-constituent amino acids, microbial metabolites or animal/plant components.

Protein-constituent amino acids include aliphatic monoaminocarboxylic acids (e.g., glycine, alanine, valine, leucine, isoleucine), aliphatic oxyamino acids (e.g., serine, threonine), acidic amino acids (e.g., aspartic acid, glutamic acid), amides of acidic amino acids (e.g., asparagine, glutamine), aromatic amino acids (e.g., phenylalanine, tyrosine, tryptophan), iminocarboxylic acids (e.g., proline, hydroxyproline), basic amino acids (e.g., arginine, lysine, histidine) and sulfur-containing amino acids (e.g., methionine, cystine, cysteine).

Amino acids obtained from nature as microbial metabolites or animal/plant components include aliphatic monoaminocarboxylic acids (e.g., L-α-aminobutyric acid, γ-aminobutyric acid, β-aminoisobutyric acid, β-alaninc, homoserine, α-methyl-D-serine, O-carbamyl-D-serine, δ-hydroxy-δ-oxo-norvaline), monoaminodicarboxylic acids (e.g., L-α-aminoadipic acid, L-theanine, L-γ-methyleneglutamic acid, L-γ-methylglutamic acid), diaminomonocarboxylic acids (e.g., L-ornithine, β-lysine, α,β-diaminopropionic acid, L-α,γ-diaminobutyric acid), diaminodicarboxylic acids (e.g., diaminopimelic acid), sulfonate-containing amino acids (e.g., cysteic acid), aromatic amino acids (e.g., quinulenine, 3,4-dioxyphenyl-L-alanine), heterocyclic amino acids (e.g., 2,3-dicarboxyadilyzine, [S]-2-amino-3-(isoxazolin- 5-on-4-yl)-propionic acid, anticapsin), basic amino acids (e.g., L-4-oxalysine, L-4-oxolysine, [3R,5R]-3,6-diamino-5-hydroxyhexanoic acid), sulfur-containing amino acids (e.g., lanthionine, S-methyl-L-cysteine), cyclic amino acids (e.g., pipecolic acid, azetidine-2-carboxylic acid, [1R,2S]-2-aminocyclopentane-1-carboxylic acid), amino acids substituted by a special functional group (e.g., citrulline, alanosine, L-azaserine), and sulfonic acid type amino acids (e.g., taurine, sulfanilic acid).

The non-natural amino acid is preferably an aliphatic or aromatic amino acid represented by the general formula:

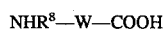

$$NHR^8—W—COOH \qquad [V]$$

wherein $R^8$ represents hydrogen or a lower alkyl group; W represents a divalent hydrocarbon group which may have a substituent.

With respect to general formula [V], the lower alkyl group for $R^8$ is exemplified by methyl, ethyl and propyl.

With respect to general formula [V], the divalent hydrocarbon group for W is exemplified by divalent aliphatic hydrocarbon groups and divalent aromatic hydrocarbon groups, as well as divalent groups resulting from a combination of such an aliphatic hydrocarbon group and such an aromatic hydrocarbon group.

Here, divalent aliphatic hydrocarbon groups include straight-chain or branched, saturated hydrocarbon groups represented by $—C_mH_{2m}—$ ($1 \leq m \leq 15$, m is an integer) (e.g., methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, ethylethylene, propylene), straight-chain or branched, unsaturated hydrocarbon groups represented by $—C_3H_2(p-q)—$ ($2 \leq p \leq 15$, p>q, p and q are integers) (e.g., propenylene, vinylene) and aliphatic cyclic hydrocarbon groups represented by $—C_{rH2}(r-1)—$ (r>3, r is an integer) (e.g., cyclohexylene, cyclopentylene). The divalent aliphatic hydrocarbon group is preferably a straight-chain or branched, saturated hydrocarbon group represented by $—C_{mH2m}—$ ($1 \leq m \leq 15$, m is an integer).

Divalent aromatic hydrocarbon groups include phenylene, pyridylene, furylene, thiazolylene, thienylene and biphenylene, which correspond to benzene, pyridine, furan, thiazole, thiophene and biphenyl, respectively. The aromatic hydrocarbon group may condense with a heterocyclic ring having an amide or imide bond therein. In this case, the bond may be present on the aromatic hydrocarbon group or the heterocyclic ring. The heterocyclic ring is exemplified by 5-membered rings such as 2-pyrrolidone, 1-pyrrolin-2-one and succinimide, and 6-membered rings such as 2-(5H, 6H)pyridinone, 2(3H,4H)pyridinone, 2-piperidinone and gtutarimide. The heterocyclic ring is preferably a 5-membered ring such as 2-pyrrolidone, 1-pyrrolin-2-one or succinimide. Preferable condensed rings include indolin-2-one, isoindolin-1one, phthalimide, 2-quinolone, 1-isoquinolone, 2-(3H,4H)quinolinone, 1(3H,4H)isoquinolinone and 4H-isoquinolinone-1,3-dione. The condensed ring is more preferably indolin-2-one, isoindolin-1-one, phthalimide or the like. Divalent condensed ring groups include groups represented by the formulas:

The divalent aromatic hydrocarbon group is preferably an aromatic hydrocarbon group having 6 to 12 carbon atoms such as phenylene or biphenylene.

When an aliphatic hydrocarbon group and an aromatic hydrocarbon group are combined together to form a divalent group, the aliphatic hydrocarbon group is preferably a straightchain or branched, saturated hydrocarbon groups represented by $-C_mH_{2m}-$ ($1 \leq m \leq 15$, m is an integer) (e.g., methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, ethylethylene, propylene). The aliphatic hydrocarbon group is more preferably methylene or ethylene. The aromatic hydrocarbon group is preferably an aromatic hydrocarbon group having 6 to 12 carbon atoms such as phenylene or biphenylene, which correspond to benzene or biphenyl, respectively.

With respect to general formula [V], the substituent in the divalent hydrocarbon group for W is exemplified by carboxyl groups, amino groups, sulfo groups and halogen atoms (e.g., chlorine, fluorine). Said substituent is preferably a carboxyl group or a halogen atom (e.g., chlorine, fluorine).

With respect to general formulas [I], [III] and [IV] (described hereinafter), the amino acid sequence for Y more preferably consists of 1 to 5 amino acid residues.

With respect to general formulas [I], [III] and [IV] (described hereinafter), the protecting group in the amino acid sequence for Y is a group known to protect the amino group, carboxyl group or hydroxyl group in peptide synthesis, which is eliminated upon, for example, hydrolysis, hydrogenolysis, reduction, aminolysis or hydrazinolysis.

Amino group protecting groups include urethane type protecting groups (e.g., carbobenzoxy, t-butyloxycarbonyl, allyloxycarbonyl, t-amyloxycarbonyl, isobornyloxycarbonyl, 4-methoxybenzyloxycarbonyl, 2-chlorobenzyloxycarbonyl, adamantyloxycarbonyl, 9-fluorenyl-methyloxycarbonyl, 2,2,2-trichloroethyloxycarbonyl), acyl type protecting groups (e.g., formyl, trifluoroacetyl, chloroacetyl, phthalyl, tosyl, 2-nitrosulphenyl, 4-methoxy-2-nitrosulphenyl, benzoyl) and alkyl type protecting groups (e.g., trityl, benzyl).

Of these, urethane type protecting groups are preferred.

The carboxyl group is protected by conversion into the amido group, the hydrazido group or an ester. The amido group or the hydrazido group is preferably substituted. The amido group is preferably substituted by, for example, a $C_{7-19}$ aralkyl group which may be substituted by, example, an alkoxy group (e.g., 3,4-dimethoxybenzyl group, bis-(p-methoxyphenyl)-methyl group). The hydrazido group is preferably substituted by, for example, a $C_{1-6}$ alkyloxycarbonyl group which may be substituted by a halogen (e.g., fluorine, chlorine, bromine) or a $C_{6-12}$ aryl group (e.g., phenyl, p-biphenyl) (e.g., benzyloxycarbonyl group, trichloroethyloxycarbonyl group, tert-butyloxycarbonyl group, 2-(p-biphenyl)-isopropyloxycarbonyl group), a halogenated $C_{2-6}$ alkanoyl group (e.g., trifluoroacetyl group) or a C7-19 aralkyl group (e.g., trityl group).

The carboxyl group is preferably esterified by, for example, a lower alcohol which may be substituted (e.g., methanol, ethanol, cyanomethyl alcohol, benzoylmethyl alcohol, tert-butanol), an alalkanol [e.g., benzyl alcohol or benzhydrol which may be substituted by a lower alkyl group, a lower alkoxy group or a halogen atom (e.g., benzhydrol, p-nitrobenzyl alcohol, p-methoxybenzyl alcohol, 2,4,6-trimethylbenzyl alcohol)], a phenol or thiophenol which may be substituted by an electron-attracting substituent (e.g., thiophenol, thiocresol, p-nitrothiophenol, 2,4,5- or 2,4,6-trichlorophenol, p-cyanophenol, p-methanesulfonylphenol), an N-hydroxyimide (e.g., Nhydroxysuccinimide, N-hydroxyphthalimide), N-hydroxypiperizine or 8-hydroxyquinoline.

The special protecting group for the carboxyl group, capable of splitting off under neutral conditions, is exemplified by the hydrocarbyl-silyl-ethyl groups (e.g., 2-(trimethylsilyl)-ethyl group) described in German Patent Publication No. 2706490.

The hydroxy group may be protected by, for example, acylation or etherification.

The acyl group for acylation is appropriately a group derived from carbonic acid (e.g., benzyloxycarbonyl group, ethyloxycarbonyl group). Appropriate groups for etherification include the benzyl group, tetrahydropyranyl group and tert-butyl group. For protecting the hydroxy group, 2,2,2-trifluoro-1-tert-butyloxycarbonylaminoethyl group and 2,2,2-trifluoro-1-benzyloxycarbonylaminoethyl group, both described on pages 3838–3849, Chemiche Berichte, Vol. 100 (1967), are appropriate.

In the amino acid sequence for Y, when the amino acid is a sulfonic acid type amino acid, the amino acid sequence has an intervening —$SO_2NH$—.

With respect to general formulas [I], [II] and [IV] (described hereinafter), n is preferably 0.

The preferred examples of compound [I] or a salt thereof include 4-[6,7-bis(12-phenyldodecanoyloxy)-4-thiaheptanoylaminomethyl]benzoyl-glutamic acid,
4-[6,7-bis(palmitoyloxy)-4-thiaheptanoylamino]benzoylglutamicacid,
4-[6,7-bis(12-phenyldodecanoyloxy)-4-thiaheptanoylamino]benzoyl-glutamic acid,
4-[6,7-bis(palmitoyloxy)-4-thia-2(Z)-heptenoylaminomethyl]benzoylglutamic acid,
4-[6,7-bis(palmitoyloxy)-2-methyl-4-thiaheptanoylamino]benzoyl-glutamic acid,
4-[6,7-bis(palmitoyloxy)-4-thiaheptanoylamino]benzoylphenylalanine, or salts thereof.

Compound [I] or a salt thereof is produced by, for example, subjecting a compound represented by the formula [II]:

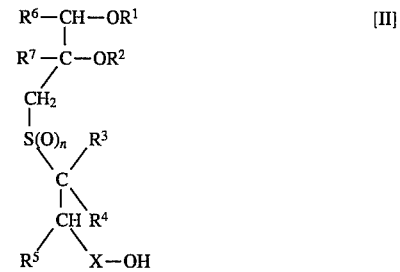

wherein $R^1$ and $R^2$ are the same or different, an acyl group; $R_3$, $R^4$, $R^6$ and $R^7$ are the same or different, hydrogen or an alkyl group; $R^5$ is hyrdrogen, an alkyl group or a hydroxyl group which may optionally be protected, or $R^4$ and $R^5$ are combined to form a chemical bond; X is a carbonyl group or a sulfonyl which a compound represented by the formula [III]:

wherein Y is an amino acid sequence consisting of 1 to 7 amino acid residues which may optionally be protected and having optionally an intervening —$SO_2NH$—, or a salt thereof, and if necessary, followed by a deprotection reaction.

This reaction is normally carried out in a solvent which does not interfere with the reaction. The solvent is selected from solvents known to be usable in peptide condensation reaction. Such solvents include amides (e.g., anhydrous or hydrated formamide, dimethylformamide, N-methylpyrrolidone), sulfoxides (e.g., dimethyl sulfoxide), aromatic amines (e.g., pyridine), halogenated hydrocarbons (e.g., chloroform, dichloromethane), ethers (e.g., tetrahydrofuran, dioxane), nitriles (e.g., acetonitrile) and esters (e.g., ethyl acetate, ethyl formate). These solvents may be used singly or in combination in appropriate ratios.

Reaction temperature is chosen as appropriate over the range known to serve for peptide bond formation reaction. Specifically, reaction temperature is chosen as appropriate over the range from about −20° to 40° C.

Reaction time is chosen as appropriate over the range known to serve for peptide bond formation reaction. Specifically, reaction time is chosen as appropriate over the range from several minutes to about 48 hours.

The amount of compound [III] or a salt thereof used is normally about 1 to 5 mol, preferably about 1 to 2 mol per tool of compound [II] or a salt thereof.

The deprotection reaction is carried out by a known method such as a common method in peptide chemistry.

For example, deprotection of the amino group protected by an urethane type protecting group is achieved by bringing the amino group in contact with an acid without solvent or in a solvent which does not interfere with the reaction. Such solvents include halogenated hydrocarbons (e.g., dichloromethane, chloroform, 1,2-dichloroethane), alcohols (e.g., methanol, ethanol), water and mixtures thereof in appropriate ratios. Useful acids include haloacetic acids (e.g., trifluoroacetic acid) and halogen halide acids (e.g., hydrochloric acid, hydrobromic acid).

It is advantageous that the N-benzyloxycarbonyl group or N-4-methoxybenzyloxycarbonyl group be eliminated by catalytic hydrogenation using a palladium catalyst such as palladium/barium sulfate or palladium black or a rhodium catalyst. In this case, a solvent known from the literature, such as a cyclic ether (e.g., tetrahydrofuran), is used singly or, in some cases, in mixture with another inert solvent [e.g., lower aliphatic acid amide (e.g., dimethylformamide)].

It is advantageous that the N-9-fluorylenyloxycarbonyl group be eliminated using an organic amine such as diethylamine, piperidine, morpholine, 4-dimethylaminopyridine or dicyclohexylamine. The reaction is carried out in a solvent which does not interfere with the reaction. Such solvents include amides (e.g., dimethyl formamide, acetamide), alcohols (e.g., methanol, ethanol), and mixtures thereof in appropriate ratios.

It is advantageous that the N-2,2,2-trichloroethyloxycarbonyl group be eliminated using a metal (e.g., zinc) along with an organic carboxylic acid (e.g., acetic acid, propionic acid). The reaction is carried out in a solvent which does not interfere with the reaction. Such solvents include the above-described organic carboxylic acids, alcohols (e.g., methanol, ethanol), water and mixtures thereof in appropriate ratios.

The deprotection reaction (deacylation) of the acylated hydroxy group is achieved by bringing the acylated hydroxy group in contact with an acid in a solvent which does not interfere with the reaction. Such solvents include halogenated hydrocarbons (e.g., dichloromethane, chloroform, 1,2-dichloroethane), alcohols (e.g., methanol, ethanol), water and mixtures thereof in appropriate ratios. Useful acids include haloacetic acids (e.g., trifluoroacetic acid) and hydrogen halide acids (e.g., hydrochloric acid, hydrobromic acid).

It is advantageous that the O-benzyl group be eliminated by catalytic hydrogenation using a palladium catalyst such as palladium/barium sulfate or palladium black or a rhodium catalyst. In this case, a solvent known from the literature, such as an alcohol (e.g., ethanol) or a cyclic ether (e.g., tetrahydrofuran) is used singly or, in some cases, in mixture with another inert solvent [e.g., lower aliphatic acid amide (e.g., dimethylformamide)].

For the O-tetrahydropyranyl group or O-tert-butyl group, deprotection can be achieved by acid hydrolysis as in the above-described deacylation.

The carboxyl protecting group can be eliminated by acid hydrolysis in the same manner as above. For example, the benzyl ester can be eliminated by catalytic hydrogenation in the same manner as for the above-described elimination of the O-benzyl group.

The 2-(trimethylsilyl)-ethyl group can be eliminated by reacting a salt of hydrofluoric acid, such as a quaternary nitrogen base salt of hydrofluoric acid (e.g., tetraethylammonium fluoride) in an appropriate solvent under neutral conditions.

Compound [I] or a salt thereof can also be produced by subjecting a compound or a salt thereof represented by the formula [IV]:

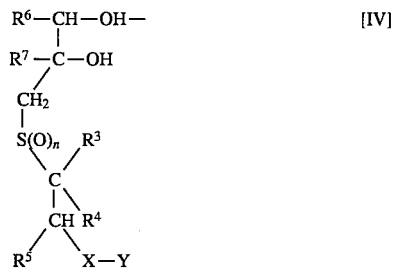

wherein $R^3$, $R^4$, $R^6$ and $R^7$ are the same or different, hydrogen or an alkyl group; $R^5$ is hydrogen, an alkyl group or a hydroxyl group which may optionally be protected, or $R^4$ and $R^5$ are combined to form a chemical bond; X is a carbonyl group or a sulfonyl group; Y is an amino acid sequence consisting of 1 to 7 amino acid residues which may optionally be protected and having optionally an intervening $—SO_2NH—$; n is an integer of 0 to 2, or a salt thereof, to an acylation reaction, and if necessary, followed by deprotection reaction.

When $R^1$ or $R^2$ is an aliphatic acyl group, the acylation reaction is carried out using, for example, a compound represented by the formula:

wherein R has the same definition as the aliphatic acyl group for $R^1$ or $R^2$ above; Z represents a halogen atom (e.g., chlorine, bromine) or a hydroxyl group.

The reaction is normally carried out in a solvent which does not interfere with the reaction. Such solvents include halogenareal hydrocarbons (e.g., chloroform, dichloromethane), aromatic hydrocarbons (e.g., benzene, toluene, xylene), amides (e.g., dimethylformamide, dimethylacetamide, N-methylpyrrolidone), sulfoxides (e.g., dimethyl sulfoxide), ethers (e.g., tetrahydrofuran, dioxane), nitriles (e.g., acetonitrile) and pyridine. These solvents may be used singly or in combination in appropriate ratios. In this reaction, it is preferable that a base (e.g., triethylamine, N,N-dimethylaniline, 4-dimethylaminopyridine, pyridine) be present for the purpose of accelerating the reaction.

When Z is a hydroxyl group, the reaction is carried out in the presence of a condensing agent. Useful condensing agents include dicyclohexylcarbodiimide, 1,1'-carbonylimidazole and N-hydroxysuccinimide.

The amount of compound [VII] used is normally about 1 to 10 mol, preferably about 1 to 5 mol per tool of compound [IV] or a salt thereof.

Reaction temperature is normally about 0° to 80° C. Reaction time is normally about 1 to 48 hours, varying depending on reaction conditions.

When $R^1$ or $R^2$ is a substituted carbamoyl group, the acylation reaction reaction is carried out using an isocyanate corresponding to the substituted carbamoyl group for $R^1$ or $R^2$.

The reaction is normally carried out in a solvent which does not interfere with the reaction. Such solvents include halogenated hydrocarbons (e.g., chloroform, dichloromethane), aromatic hydrocarbons (e.g., benzene, toluene, xylene), amides (e.g., dimethylformamide, dimethylacetamide, N-methylpyrrolidone), sulfoxides (e.g., dimethyl sulfoxide), ethers (e.g., tetrahydrofuran, dioxane), nitriles (e.g., acetonitrile) and pyridine. These solvents may be used singly or in combination in appropriate ratios. In this reaction, it is preferable that a base (e.g., triethylamine, N,N-dimethylaniline, 4-dimethylaminopyridine, pyridine, di-n-dibutyltin dichloride) be present for the purpose of accelerating the reaction.

The amount of isocyanate used is normally about 1 to 10 mol, preferably about 1 to 5 mol per mol of compound [IV] or a salt thereof.

Reaction temperature is normally about 0° to 150° C. Reaction time is normally about 1 to 24 hours, varying depending on reaction conditions.

When $R^1$ and $R^2$ are different groups, the above-described reactions are carried out in two steps.

The above-described acylation reaction is followed by deprotection if necessary. The deprotection reaction is carried out in the same manner as the deprotection reaction described above.

Concerning the production of compound [I] or a salt thereof exemplified above, time of introduction of the amino acid sequence for Y is not limited to the above-described time, and it may be changed as necessary. For the protecting group for the amino acids constituting the amino acid sequence for Y, the protecting group may be introduced or eliminated as necessary.

The compound or a salt thereof of general formula [I] wherein n is the integer 1 or 2 is produced by, for example, oxidizing the compound or a salt thereof of general formula [I] wherein n is 0. This oxidation is carried out in a solvent which does not interfere with the reaction, using an oxidizing agent. Such solvents include halogenated hydrocarbons (e.g., chloroform, dichloromethane), ethers (e.g., tetrahydrofuran, dioxane), ketones (e.g., acetone, methyl ethyl ketone), alcohols (e.g., methanol, ethanol, t-butyl alcohol), nitriles (e.g., acetonitrile), carboxylic acids (e.g., acetic acid) and water. These solvents may be used singly or in combination in appropriate ratios. Useful oxidizing agents include oxygen-light, hydrogen peroxide, sodium metaperiodate, perbenzoic acids such as perbenzoic acid and mchloroperbenzoic acid, perchlorates such as lithium perchlorate, silver perchlorate, mercuric perchlorate and tetrabutylammonium perchlorate, nitrosylsulfuric acid, alkyl nitrites such as isoamyt nitrite, halogens such as iodine, bromine and chlorine, N-bromosuccinimide, sulfuryl chloride and chloramine T. The oxidizing agent is preferably sodium metaperiodate or a perbenzoic acid such as perbenzoic acid or m-chloroperbenzoic acid. The mount of oxidizing agent used is normally about 1 to 10 mol, preferably about 1 to 5 mol per mol of the starting material compound. Reaction temperature is normally about 0° to 150° C. Reaction time is normally about 1 to 24 hours, varying depending on reaction conditions.

Compound [I] or a salt thereof thus obtained can be isolated by conventional means of separation and purification (e.g., extraction, distribution, reprecipitation, chromatography, recrystallization).

When diastereomers are present in compound [I], they can be isolated by the above-described means of separation and purification as desired. All such isomers are of course included in the compounds of the present invention. When compound [I] has been obtained in racemates, they can be separated into the d- and l-configurations by optical resolution.

Compound [I] can be converted into a salt with a base, particularly a pharmaceutically acceptable base. Such bases include alkali metals (e.g., sodium, potassium), alkaline earth metals (e.g., calcium, magnesium) and organic bases (e.g., triethylamine, piperidine). Compound [I] can also be obtained as an acid-addition salt, particularly a pharmacologically acceptable acid-addition salt. Such acids include inorganic acids (e.g., hydrochloric acid, sulfuric acid, phosphoric acid) and organic acids (e.g., acetic acid, propionic acid, citric acid, tartaric acid, malic acid, oxalic acid).

With respect to the salts of compounds [II], [III] and [IV] above, the same applies as with compound [I].

A compound or a salt thereof of general formula [II] wherein n is 0 (compound [II']) can be produced by, for example, the method schematized by the following reaction formulas:

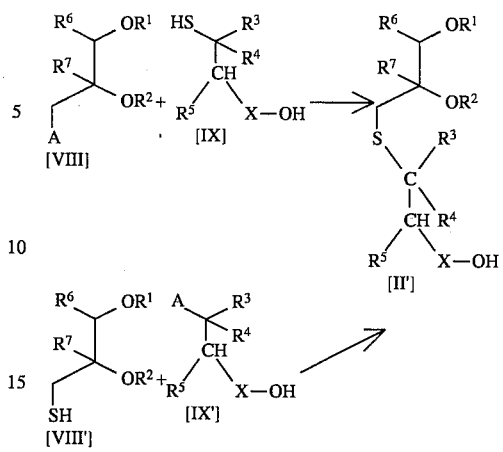

wherein $R^1$, $R^2$, $R^3$, $R^4$, $R^5$, $R^6$, $R^7$ and X have the same definitions as above; A represents iodine, bromine or a group represented by the formula $R'—SO_2O—$ ($R'$ represents methyl, phenyl, p-tolyl or the like).

The above reaction is normally carried out in a solvent which does not interfere with the reaction. Such solvents include halogenated hydrocarbons (e.g., chloroform, dichloromethane), aromatic hydrocarbons (e.g., benzene, toluene, xylene), amides (e.g., dimethylformamide, dimethylacetamide, N-methylpyrrolidone), sulfoxides (e.g., dimethyl sulfoxide), ethers (e.g., tetrahydrofuran, dioxane), nitriles (e.g., acetonitrile) and pyridine. These solvents may be used singly or in combination in appropriate ratios. In this reaction, it is preferable that a base (e.g., triethylamine, diisopropylethylamine, N,N-dimethylaniline, 4-dimethylaminopyridine, pyridine) be present for the purpose of accelerating the reaction. Reaction temperature is normally about 0° to 150° C. Reaction time is normally about 1 to 48 hours, varying depending on reaction conditions. Compound [II] can also be produced by the method schematized by the following reaction formulas:

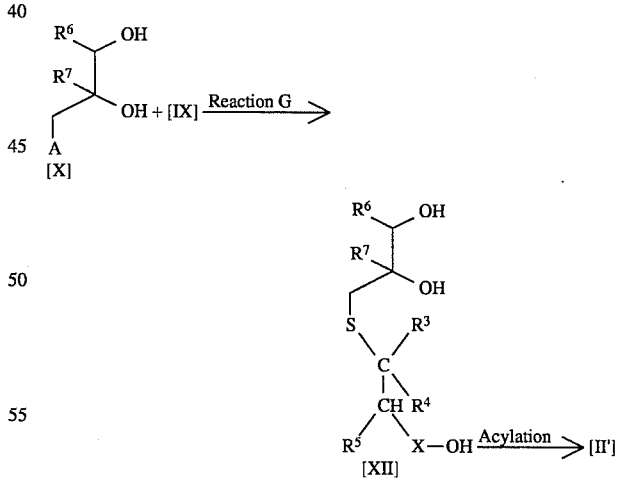

wherein the symbols have the same definitions as above. Here, reaction G is carried out in the same manner as the reaction of compound [VIII] or a salt thereof with compound [IX] or a salt thereof. Acylation is carried out in the same manner as with the above-described compound [I] or a salt thereof. A compound or a salt thereof of general formula [IV] wherein n is 0 (compound [IV']) can be produced by, for example, the method schematized by the following reaction formulas:

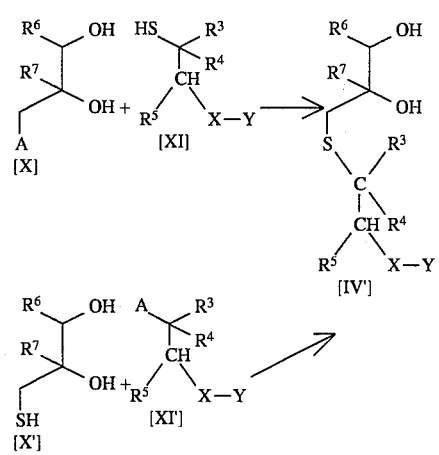

wherein $R^3$, $R^4$, $R^5$, $R^6$, $R^7$, X and Y have the same definitions as above; A represents iodine, bromine or a group represented by the formula $R'-SO_2O-$ (R' represents methyl, phenyl, p-tolyl or the like).

The above reaction is carried out in the same manner as with the above-described compound [II'] or a salt thereof.

Compound [IV'] can also be produced by the method schematized by the following reaction formulas:

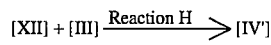

Here, reaction H is carried out in the same manner as the reaction of compound [II] or a salt thereof with compound [III] or a salt thereof. The above-described starting material compounds [VIII] through [XI] and [VIII'] through [XI'] or salts thereof (hereinafter referred to as compounds VIII], [IX], [X], [XI], [VIII'], [IX'], [X'], [XI'] etc.) are obtained by per se known methods (e.g., those using commercial reagents) or those described in Reference Examples. When these compounds are used as salts, the same salts as the above-described salts of compound [I] are used. For example, compounds [VIII], [VIII'], [X] and [X'] can be produced by the methods described in Synthesis, 889 (1990) by Luis Moroder, HansJurgen Musiol and Gabriele Siglmuller, in the Journal of Organic Chemistry, Vol. 47, No. 18, 3581–3585 (1982) and the Journal of Pharmaceutical Sciences, Vol. 70, No. 10, 1154–1156 (1981)], or modifications thereof. Compound [IX] can be produced by, for example, the method schematized by the following reaction formulas:

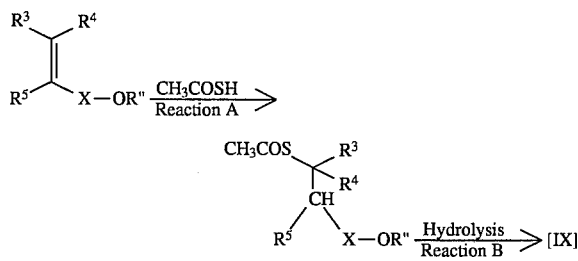

wherein R' represents an alkyl group such as methyl or ethyl; the other symbols have the same definitions as above.

Here, reaction A is normally carried out in a solvent which does not interfere with the reaction in the presence of a base. Such solvents include amides (e.g., dimethylformamide, dimethylacetamide, N-methylpyrrolidone) and halogenated hydrocarbons (e.g., chloroform, dichloromethane). Such bases include alkali metal hydroxides (e.g., potassium hydroxide), alkali metal carbonates (e.g., potassium carbonate) and pyridine. Reaction temperature is normally about 0° to 150° C. Reaction time is normally about 1 to 24 hours, varying depending on reaction conditions.

Reaction B is normally carried out in a solvent which does not interfere with the reaction in the presence of water and a base. Such solvents include alcohols (e.g., methanol, ethanol) and water-alcohol mixtures (e.g., aqueous methanol, aqueous ethanol). Such bases include alkali metal hydroxides (e.g., sodium hydroxide, potassium hydroxide) and alkali metal alcoholates (e.g., sodium methoxide). Reaction temperature is normally about 0° to 50° C. Reaction time is normally about 1 to 10 hours, varying depending on reaction conditions.

Compound [IX'] can be produced by, for example, the method schematized by the following reaction formulas:

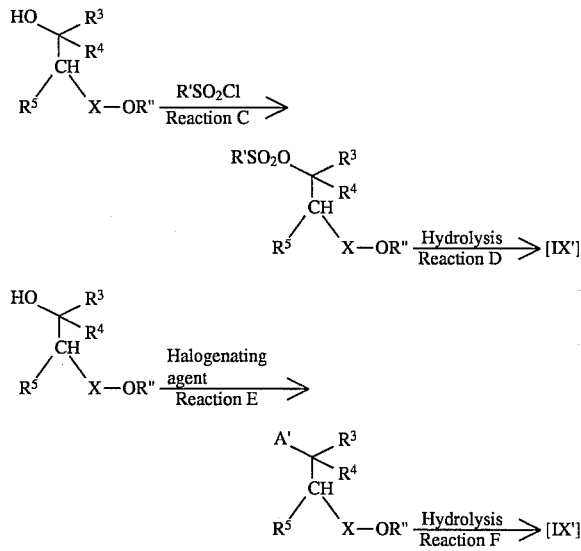

wherein R" represents an alkyl group such as methyl or ethyl; A' represents iodine or bromine; the other symbols have the same definitions as above.

Here, reaction C is normally carried out in a solvent which does not interfere with the reaction. Such solvents include halogenated hydrocarbons (e.g., chloroform, dichloromethane), aromatic hydrocarbons (e.g., benzene, toluene, xylene), amides (e.g., dimethylformamide, dimethylacetamide, N-methylpyrrolidone), sulfoxides (e.g., dimethyl sulfoxide), ethers (e.g., tetrahydrofuran, dioxane), nitriles (e.g., acetonitrile) and pyridine. These solvents may be used singly or in combination in appropriate ratios. In this reaction, it is preferable that a base (e.g., triethylamine, N,N-dimethylaniline, 4-dimethylaminopyridine, pyridine) be present for the purpose of accelerating the reaction. Reaction temperature is normally about 0° C. to room temperature. Reaction time is normally about 1 to 10 hours, varying depending on reaction conditions.

Reaction D is normally carried out in a solvent which does not interfere with the reaction under acidic conditions. Such solvents include water-alcohol mixtures (e.g., aqueous methanol, aqueous ethanol) and ethers (e.g., tetrahydrofuran, dioxane). Reaction temperature is normally about 0° C. to room temperature. Reaction time is normally about 1 to 10 hours, varying depending on reaction conditions.

Reaction E is carried out in a solvent which does not interfere with the reaction, using a halogenating agent. This reaction is exemplified by reactions in a solvent such as petroleum ether or a halogenated hydrocarbon (e.g., chloroform, dichloromethane) using a phosphorus halide (e.g., phosphorus tribromide, phosphorus trichloride, phosphorus pentabromide, phosphorus pentachloride), reactions in a solvent such as an alkyl halide (e.g., carbon tetrachloride, carbon tetrabromide) using triphenyl phosphonate, triphenylphosphine or the like, reactions in a solvent such as an amide (e.g., dimethylformamide, dimethylacetamide, N-methylpyrrolidone) using diphenyltrihalogenophospholane, triphenylphosphine dihalogenide or the like, and reactions in a solvent such as an amine (e.g., pyridine) using sulfonyl chloride, thionyl halide or the like. Reaction temperature is normally about −30° to 50° C. Reaction time is normally about 20 minutes to 3 hours.

Reaction E above is carried out in the same manner as reaction D above.

Compounds [XI] and [XI'] are produced by reacting compound [IX] or [IX'] with compound [III] or a salt thereof in the same manner as the reaction of compound [II] or a salt thereof with compound [III] or a salt thereof.

A compound represented by general formula [III] or a salt thereof can be produced by condensing a starting material having a reactive carboxyl group corresponding to one of the two fragments resulting from division of the amino acid sequence for Y at a given position of peptide bond and a starting material having a reactive amino group corresponding to the other fragment by a conventional means of peptide synthesis.

The conventional means of peptide synthesis may be based on liquid-phase synthesis or solid-phase synthesis. Such peptide synthesis can be achieved by a known method. Specifically, it is achieved by the methods described in Peptide Synthesis, by M. Bondasky and M. Ondetti, Interscience, New York, 1966; The Proteins, Volume 2, by F. M. Finn and K. Hofmann, edited by H. Nenrath and R. L. Hill, Academic Press Inc., New York, 1976; Peputido Gosei no Kiso to Jikken, by N. Izumiya et al., Maruzen, 1985; Seikagaku Jikken Koza 1, by H. Yajima, S. Sakakibara et al., edited by the Biochemical Society of Japan, Tokyo Kagaku Dojin, 1977; Zoku Seikagaku Jikken Koza 2, by S. Kimura et al., edited by the Biochemical Society of Japan, Tokyo Kagaku Dojin, 1987; Solid Phase Peptide Synthesis, by J. M. Stewart and J. D. Young, Pierce Chemical Company, Illinois, 1984, or modifications thereof. Specifically, such methods include the azide method, the chloride method, the acid anhydride method, the acid arthydride mixture method, the DCC method, the active ester method, the Woodward reagent K method, the carbonylimidazole method, the oxidation reduction method, the DCC/I-IONB method, the DIC/HONB method, the DCC/HONB method and the BOP reagent method.

Abbreviations for amino acids and peptides used in the present specification are based on abbreviations specified by the IUPAC-IUB Commission on Biochemical Nomenclature or abbreviations in common use in relevant fields. When an optical isomer may be present in amino acid, it is of the L-configuration, unless otherwise stated.

The skeletal compound for the compounds mentioned in the present specification is 6,7-dihydroxy-4-thiaheptanoic acid, represented by the formula:

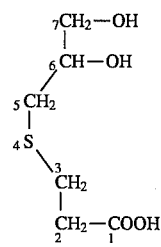

Compound [I] or a salt thereof the present invention (hereinafter on bone marrow cell growth promoting activity and leukocyte increasing activity, and platelet reduction recovery action.

The inventive compound is used as a prophylactic/therapeutic agent for leukocytopenia resulting from radiotherapy or chemotherapy for cancer in mammals (e.g., mice, dogs, pigs, bovines, horses, monkeys, humans), and as an immunoenhancing agent in bone marrow transplantation therapy and the treatment of osteomyelodysplasia and aplastic anemia, and as a prophylactic/therapeutic agent for thrombocytopenia. The inventive compound is further used in a diagnostic test to determine a subject's level of immune activity.

The composition for immuno-enhancement of the present invention is used for preventing or treating infectious diseases such as bacterial diseases (s.g., pertussis, diphtheria, tetanus), vital diseases (e.g., measles, mumps, rubella, polio, herpes), mycosis (e.g., moniliasis, aspergillosis), rickettsiosis (e.g., typhus) and tumor The inventive compound is further used as an immuno adjuvant (a substance which enhances antigenicity and gives a superior immune response when mixed with and antigen.

With low toxicity, the inventive compound can be safely used.

When administered to a human or non-human mammal, the inventive compound can be safely administered orally or non-orally as such or in a pharmaceutical composition along with an appropriate pharmacologically acceptable carrier, exeipient and diluent.

Such pharmaceutical compositions include oral preparations (e.g., powders, granules, capsules, tablets), non-oral preparations [e.g., injections, drip infusions, external preparations (e.g., transnasal preparations, percutaneous preparations), and suppositories (e.g., rectal suppositories, vaginal suppositories)].

These preparations can be produced by known methods in common use for pharmaceutical preparations.

An oral preparation can be produced by adding an excipient (e.g., lactose, sucrose, starch), a disintegrating agent (e.g., starch, calcium carbonate), a binder (e.g., starch, gum arabic, carboxymethyl cellulose, polyvinylpyrrolidone, hydroxypropyl cellulose), a lubricant (e.g., talc, magnesium stearate, polyethylene glycol 6000) and other additives to the inventive compound, compressively shaping the mixture and, where necessary, coating for taste masking, enteric dissolution or sustained release. Coating may be achieved by a known method. Coating agents for this purpose include hydroxypropylmethyl cellulose, ethyl cellulose, hydroxymethyl cellulose, hydroxypropyl cellulose, polyoxyethylene glycol, Tween 80, Prulonic F68, cellulose acetate phthalate, hydroxypropylmethyl cellulose phthalate, hydroxymethyl cellulose acetate succinate, Eudragit (produced by gohm Company, Germany, methacrylic acid/acrylic acid copolymer) and dyes such as iron oxide.

An injection can be produced by, for example, preparing the inventive compound as an aqueous injection along with a dispersing agent (e.g., Tween 80, produced by Atlas Powder Company, USA, HCO 60, produced by Nikko Chemicals Co., Ltd., polyethylene glycol, carboxymethyl cellulose, sodium alginate), a preservative (e.g., methyl paraben, propyl paraben, benzyl alcohol), an isotonizing agent (e.g., sodium chloride, mannitol, sorbitol, glucose) and other additives, or as an oily injection in solution, suspension or emulsion in a vegetable oil such as olive oil, sesame oil, cottonseed oil or corn oil, propylene glycol or the like.

An external preparation can be produced by compounding the inventive compound as a solid, semi-solid or liquid composition. Such a solid composition is produced by, for example, powdering the inventive compound as such or in mixture with an excipient (e.g., glycol, mannitol, starch, microcrystalline cellulose), a thickening agent (e.g., natural rubber, cellulose derivative, acrylic acid polymer) and other additives. Such a liquid composition is produced by preparing the inventive compound as an oily or aqueous suspension in almost the same manner as with the injection. The semi-solid composition is preferably an aqueous or oily gel, or cartilageous. All these compositions may contain pH regulators (e.g., carbonic acid, phosphoric acid, citric acid, hydrochloric acid, sodium hydroxide), preservatives (e.g., paraoxybenzoates, chlorobutanol, benzalkonium chloride) and other additives.

A suppository is produced by preparing the inventive compound as an oily or aqueous solid, semi-solid or liquid composition. Useful oily bases for such compositions include glycerides of higher fatty acids (e.g., cacao fat, uitepsols, produced by Dynamite Nobel Company), moderate fatty acids (e.g., mygliols, produced by Dynamite Nobel Company), and vegetable oils (e.g., sesame oil, soybean oil, cottonseed oil). Aqueous bases include polyethylene glycols and propylene glycol. Bases for aqueous gels include natural rubbers, cellulose derivatives, vinyl polymers and acrylic acid polymers.

Depending on target disease, route of administration, age of patient, and severity of disease, the dose of the inventive compound in humans is normally about 0.1 to 300 mg for an ordinary adult patient (50 kg body weight) per day, based on active ingredient content. When used as an injection, the inventive compound is used at about 0.1 to 100 mg, preferably about 0.2 to 50 mg for an ordinary adult patient (50 kg body weight) per day, based on active ingredient content. One of ordinary skill in the art would be capable of determining the proper dosage to use for a human or non-human subject depending upon the target disease, a route of administration, etc. without undue experimentation.

The present invention is hereinafter described in more detail by means of the following reference examples and working examples. Percent figures are by weight, unless otherwise stated. With respect to mixed solvents, mixing ratios are shown by volume. The abbreviations used in the reference examples and working examples are defined as follows:

s: singlet, d: doublet, t: triplet, q: quartet, dd: double doublet, dr: double triplet, m: multiplet, br: broad, J: coupling constant, DEPC: diethyl cyanophosphate.

REFERENCE EXAMPLE 1

B is
((2-p-methoxybenzyloxycarbonyl)ethyl)disulfide

To a solution of bis(2-hydroxycarbonylethyl)disulfide (10.00 g) in dimethylformamide (150 ml), triethylamine (26.5 ml) and p-methoxybenzyl chloride (14.2 ml) were added at room temperature, followed by stirring at 70° C. for 24 hours. After addition of water, the reaction mixture was extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The residue was crystallized (hexane) to yield the title compound (6.41 g, yield 30%) as a white powder.

$IR_{max}^{Ksr}$ cm$^{-1}$: 1725, 1610
$^1$H-NMR (CDCl$_3$)δ: 2.67–2.79 (4H, m), 2.82–2.95 (4H, m), 3.80 (6H, s), 5.07
(4H, s), 6.82–6.93 (4H, m), 7.22–7.34 (4H, m)

REFERENCE EXAMPLE 2

6,7-dihydroxy-4-thiaheptanoic acid p-methoxybenzyl ester

To a solution of bis((2-p-methoxybenzyloxycarbonyl)ethyl)disulfide as obtained in Reference Example 1 (2.25 g) in chloroform (50 ml), triethylamine (2.1 ml) and dithioerythritol (3.09 g) were added at room temperature, followed by stirring at room temperature for 4 hours in a nitrogen stream. After addition of a 5% aqueous solution of citric acid, the reaction mixture was extracted with methylene chloride, washed with saturated saline, and dried over anhydrous sodium sulfate, and the solvent was distilled off. To a solution of the residue in dimethylformamide (25 ml), triethylamine (3.5 ml) and 1-bromoglycerol (4.56 g) were added at room temperature, followed by stirring at 80° C. for 24 hours. After cooling and addition of water, the reaction mixture was extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The residue was purified by silica gel chromatography (ethyl acetate) to yield the title compound (2.00 g, yield 67%) as a white powder.
$IR_{max}^{KBr}$ cm$^{-1}$:3400, 1725, 1610
$^1$H-NMR (CDCl$_3$)δ:2.52–2.89(6H, m), 3.43–3.95 (3H, m), 3.81 (3H, s), 5.08
(2H, s), 6.82–6.96 (2H, m), 7.25–7.40 (2H, m)

REFERENCE EXAMPLE 3

6,7-bis(palmitoyloxy)-4-thiaheptanoic acid p-methoxybenzyl ester

To a solution of 6,7-dihydroxy-4-thiaheptanoic acid p-methoxybenzyl ester as obtained in Reference Example 2 (1.99 g) in methylene chloride (26 ml), triethylamine (4.6 ml), palmitoyl chloride (6.00 g) and dimethylaminopyridine (5 mg) were added at 0° C., followed by stirring at room temperature for 24 hours. After addition of 5% citric acid, the reaction mixture was extracted with methylene chloride. The extract was washed with a saturated aqueous solution of sodium hydrogen carbonate and saturated saline, and dried over anhydrous sodium sulfate, and the solvent was distilled off. The residue was recrystallized (methanol-hexane) to yield the title compound (2.30 g, yield 45%) as a white powder.
$I_{max}^{KBr}$ cm$^{-1}$: 1730, 1620
$^1$H-NMR (CDCl$_3$)δ:0.88 (6H, t, J=6.6 Hz), 1.12–1.48 (48H, m), 1.50–1.72 (4H,m), 2.31 (4H, t, J=7.6 Hz), 2.57–2.90 (6H, m), 3.81 (3H, s), 4.16 (1H, dd, J=6.0, 12.0 Hz), 4.35 (1H, dd, J=3.6, 12.0 Hz), 5.08 (2H, s), 5.04–5.20 (1H, m), 6.83–6.93 (2H, m), 7.24–7.33 (2H, m)

REFERENCE EXAMPLE 4

6,7-bis(palmitoyloxy)-4-thiaheptanoic acid

To 6,7-bis(palmitoyloxy)-4-thiaheptanoic acid p-methoxybenzyl ester as obtained in Reference Example 3 (1.17 g), a solution of anisole (0.33 ml) in trifluoroacetic acid (3.3 ml) was added at room temperature, followed by stirring at room temperature for 30 minutes. The reaction mixture was concentrated, and the residue was washed with hexane to yield the title compound (643 mg, yield 65%) as a powder.
$IR_{max}^{KBr}$ cm$^{-1}$: 3450, 1735, 1700
$^1$H-NMR (CDCl$_3$) 0.88 (6H, t, J=6.8 Hz), 1.12–1.43 (48H, m), 1.51–1.74 (4H, m), 2.25–2.38 (4H, m), 2.62–2.92 (6H, m), 4.17 (1H, dd, J=5.9, 11.8 Hz), 4.37 (1H, dd, J=3.5, 11.8 Hz), 5.08–5.21 (1H,m)

REFERENCE EXAMPLE 5

2,2'-dithiobis[4-((1,3-bis(t-butoxycarbonyl)propyl) carbamoyl)phenyl)carbamoylethane]

To a solution of 4-aminobenzoylglutamic acid di-t-butyl ester (1.15 g) in pyridine (10 ml), phosphorus trichloride (0.17 ml) was added at room temperature, followed by stirring at room temperature for 2 hours, after which 3,3'-dithiodipropionic acid (0.42 g) was added, followed by stirring at room temperature for 65 hours. After addition of water, the reaction mixture was extracted with ethyl acetate. The extract was washed with 5% citric acid, a saturated aqueous solution of hydrogen carbonate and saturated saline, and dried over anhydrous sodium sulfate, and the solvent was distilled off. The residue was purified by silica gel column chromatography (hexane:ethyl acetate=2:3 to 1:2) to yield the title compound (0.96 g, yield 54%) as a white powder.
$IR_{max}^{KBr}$ cm$^{-1}$: 3.310, 1715, 1640
$^1$H-NMR (CDCl$_3$)δ:1.42 (18H), 1.48 (18H, s), 1.95–2.47 (SH, m), 2.78 (4H, t. J =7.2 Hz), 3.05 (4H, t, J=7.2 Hz), 4.57–4.71 (2H, m), 7.15 (2H, d, J=7.2 Hz), 7.61 (4H, d, J=8.8 Hz), 7.75 (4H, d, J=8.8 Hz), 8.59 (2H, bs)

REFRENCE EXAMPLE 6

(4-(6,7-dihydroxy-4-thiaheptanoylamino) benzoyl)glutamic acid di-t-butyl ester To a solution of 2,2'-dithiobis[(4-((1,3-bis(t-butoxycarbonyl)propyl) carbamoyl)phenyl)carbamoylethane] as obtained in Reference Example 5 (603 mg) in chloroform (6.8 ml), triethylamine (0.29 ml) and dithioerythritol (421 mg) were added at roo_m temperature, followed by stirring at room temperature for 4 hours in a nitrogen stream. After addition of a 5% aqueous solution of citric acid, the reaction mixture was extracted with methylene chloride. The extract was washed with saturated saline, and dried over anhydrous sodium sulfate, and the solvent was distilled off. To a solution of the residue in dimethylformamide (24 ml), triethylamine (0.48 ml) and 1-bromoglycerol (623 mg) were added at room temperature, followed by stirring at 80° C. for 34 hours. After cooling and addition of water, the reaction mixture was extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The residue was purified by silica gel chromatography (ethyl acetate) to yield the title compound (329 mg, yield 45%) as a white powder.
$IR_{max}^{KBr}$ cm$^{-1}$: 3360, 1720, 1680, 1660, 1600
$^1$H-NMR (CDCl$_3$) 3:1.42 (9H, s), 1.48 (9H, s), 1.89–3.00 (10H, m), 3.25–3.95 (3H, m), 4.56–4.69 (1H, m), 7.29 (1H, d, J=8.0 Hz), 7.60 (2H, d, J=8.8 Hz) 7.74 (2H, d,J=8.8 Hz), 8.87 (1H, bs)

REFERENCE EXAMPLE 7

6,7bis(octadecylcarbamoyloxy)-4-thiaheptanoic acid t-butyl ester (A)

6-hydroxy:7-octadecylcarbamoyloxy-4-thiaheptanoic acid t-butyl ester (B)

A solution of 6,7-dihydroxy-4-thiaheptanoic acid t-butyl ester (2.0 g), dimethylaminopyridine (1.55 g) and octadecyl isocyanate (3.75 g) in dichloroethane (15 ml) was stirred at 80° C. for 1 hour, followed by solvent concentration under reduced pressure. The residue was purified by silica gel column chromatography (n-hexane:ethyl acetate=3:1 to 1:1) to yield the title compound (B) (3.75 g, yield 83%) as a colorless wax-like substance and the title compound (A) (1.013 g, yield 14%) as a colorless wax-like substance.
(A)
IR (Neat) υ: 3320, 2920, 2850, 1730, 1690, 1650, 1540, 1460, 1360, 1250, 1140 cm$^{-1}$
$^1$H-NMR (CDCl$_3$)δ:0.88 (6H, t, J=6.8 Hz), 1.26 (60H, s), 1.45 (9H, s), 1.40–1.60 (4H, m), 2.53 (2H, t, J=7.2 Hz), 2.74 (2H, d, J=6.6 Hz), 2.81 (2h, t, J=7.2 Hz), 3.10–3.25 (4H, m), 4.15–4.35 (2H, m), 4.70–4.90 (2H, m), 5.03 (1H, m)
(B)
IR (Neat) υ: 3350, 2920, 2850, 1720, 1700, 1530, 1465, 1365, 1250, 1150 cm$^{-1}$
$^1$H-NMR (CDCl$_3$) 8:0.88 (3H, t, J=6.8 Hz), 1.26 (30H, s), 1.46 (9H, s), 1.40– 1.60 (2H,m), 2.53 (2H, t, J=7.2 Hz), 2.59 (1H, dd, J=14.1, 7.6 Hz), 2.73 (1H dd, J= 14.5, 5.2 Hz), 2.80 (2H, t, J=7.2 Hz), 3.17 (2H, q, J=6.6 Hz), 3.27 (1H, d, J=3.8 Hz), 3.94 (1H, m), 4.09 (1H, dd, J=11.4, 6.0 Hz), 4.23 (1H, dd, J=11.4, 3.4 Hz), 4.86 (1H, brt, J=6.6 Hz)

REFERENCE EXAMPLE 8

7-octadecylcarbamoyloxy-6-palmitoyloxy-4-thiaheptanoic acid t-butyl ester

A solution of 6-hydroxy-7-octadecylcarbamoyloxy-4-thiaheptanoic acid t-butyl ester as obtained in Reference Example 7 (2.98 g), dimethylaminopyridine (820 mg) and palmitoyl chloride (1.54 g) in dichloromethane (10 ml) was stirred at room temperature for 30 minutes, followed by solvent concentration under reduced pressure. The residue was purified by silica gel column chromatography (n-hexane:ethyl acetate=10:1) to yield the title compound (3.425 g, yield 79%) as a colorless wax-like substance.
IR (Neat) υ: 2920, 2850, 1730, 1710, 1460, 1370, 1250, 1150, 730 cm$^{-1}$
$^1$H-NMR (CDCl$_3$)δ:0.88 (6H, t, J=6.6 Hz), 1.25 (54H, s), 1.49 (9H, s), 1.40–1.70 (4H, m), 2.32 (2H, t, J=7.5 Hz), 2.52 (2H, t, J=7.0 Hz), 2.70– 2.85 (4H, m, 3.16 (2H, q, J=6.6 Hz), 4.19 (1H, dd, J=11.8, 5.6 Hz), 4.31 (1H, dd, J=11.8, 3.4 Hz), 4.71 (1H, brt, J=4.6 Hz), 5.13 (1H, m)

REFERENCE EXAMPLE 9

7-octadecylcarbamoyloxy-6-palmitoyloxy-4-thiaheptanoic acid

A solution of 7-octadecylcarbamoyloxy-6-palmitoyloxy-4-thiaheptanoic acid t-butyl ester as obtained in Reference Example 8 (3.425 g) in trifluoroacetic acid (5 ml)-dichloromethane (3 ml) was stirred at room temperature for 1 hour, followed by solvent concentration under reduced pressure, to yield the title compound (3.14 g, yield 99%) as a colorless solid.
IR (KBr) υ: 3351, 2917, 2850, 1735, 1700, 1535, 1469, 1263, 1174, 1145 cm$^{-1}$
$^1$H-NMR (CDCl$_3$) δ:0.88 (6H, t, J=6.6 Hz), 1.25 (54H, s), 1.40–1.70 (4H, m), 2.33 (2H, t, J=7.5 Hz), 2.60–2.75 (4H, m), 2.84 (2H, t, J=6.0 Hz), 3.10–3.25 (2H, m), 4,19 (1H, dd, J=11.8, 5.8 Hz), 4.32 (1H, dd, J=11.8, 3.4 Hz), 4.72 (1H, brs), 5.14 (1H, m)

REFERENCE EXAMPLE 10

6,7-bis(octadecylcarbamoyloxy)-4-thiaheptanoic acid

A solution of 6,7-bis(octadecylcarbamoyloxy)-4-thiaheptanoic acid t-butyl ester as obtained in Reference Example 7 (1010 mg) in trifluoroacetic acid (3 ml)-dichloromethane (0.5 ml) was stirred at room temperature for 1 hour, followed by solvent concentration under reduced pressure, to yield the title compound (938 mg, yield 99%) as a colorless solid.
IR (KBr) υ: 3324, 2919, 2850, 1699, 1552, 1535, 1467, 1284, 1203, 1155 cm$^{-1}$
$^1$H-NMR (CDCl$_3$) δ:0.88 (6H, t, J=6.8 Hz), 1.25 (60H, s), 1.40–1.55 (4H, m), 2.60–2.90 (6H, m), 3.10–3.25 (4H, m), 4.15–4.35 (2H, m), 4.70–4.90 (2H, (1H, m)

REFERENCE EXAMPLE 11

6,7-dihydroxy-4-thia-2(E)-heptenoic acid t-butyl ester and 6,7-dihydroxy- 4-thia-2(Z)-heptenoic acid t-butyl ester To a solution of t-butyl propiolate (1.17 g) and thioglycerol (1.0 g) in dichloromethane (5 ml), one drop of triethylamine was added, followed by stirring at room temperature for 30 minutes. The reaction mixture was concentrated; the resulting residue was purified by silica gel column chromatography (n-hexane:ethyl acetate=1:1) to yield the E-configuration (1.50 g, yield 70%) and Z-configuration (645 mg, yield 30%) of the title compound as colorless oily substances.
IR (Neat) υ: 3400, 2970, 2925, 1700, 1680, 1575, 1365, 1310, 1250, 1140 cm$^{-1}$ E-configuration
$^1$H-NMR (CDCl$_3$)δ:1.48 (9H, s), 2.39 (1H, brs), 2.80–3.10 (3H, m), 3.55–3.851 Z-configuration
$^1$H-NMR (CDCl$_3$) δ:1.50 (9H, s), 2.58 (1H, brs), 2.80–3.10 (3H, m), 3.55–3.85 (2H, m), 3.92 (1H, m), 5.81 (1H, d,J=10.2 Hz), 7.02 (1H, d, J=10.2 Hz)

REFERENCE EXAMPLE 12

6,7-bis(palmitoyloxy)-4-thia-2(E)-heptenoic acid t-butyl ester

To a solution of 6,7-dihydroxy-4-thia-2(E)-heptenoic acid t-butyl ester as obtained in Reference Example 11 (600 mg) and dimethylaminopyridine (687 mg) in dichloromethane (15 ml), palmitoyl chloride (1548 mg) was added, followed by stirring at room temperature for i hour. The mixture was diluted with dichloromethane, washed with water, and dried over sodium sulfate, followed by solvent concentration. The resulting residue was purified by silica gel column chromatography (n-hexane:ethyl acetate:dichloromethane=20:1:1) to yield the title compound (1.48 g, yield 81%) as a colorless crystal.
IR (KBr) υ: 2920, 2850, 1740, 1690, 1570, 1460, 1360, 1230, 1150 cm$^{-1}$
$^1$H-NMR (CDCl$_3$) δ: 0.88 (6H, t, J=6.8 Hz), 1.25 (48H, s), 1.48 (9H, s), 1.50–1.70 (4H, m), 2.32 (2H, t, J=7.6 Hz), 2.33 (2H, t, J=7.6 Hz), 3.03 (2 H, d, J=6.4 Hz), 4.17 (1H, dd, J=12.0, 5.4 Hz), 4.32 (1H, dd, J=12.0, 4.0 Hz), 5.21 (1H, m), 5.78 (1H, d, J=15.2 Hz), 7.49 (1H, d, J=15.2 Hz)

REFERENCE EXAMPLE 13

6,7-bis(palmitoyloxy)-4-thia-2(E)-heptenoic acid

To a solution of 6,7-bis(palmitoyloxy)-4-thia-2(E)-heptenoic acid t-butyl ester as obtained in Reference Example 12 (1.4 g) in dichloromethane (2 ml), trifluoroacetic acid (4 ml) was added, followed by stirring at room temperature for 1 hour. The solvent was concentrated under reduced pressure to yield 6,7-bis(palmitoyloxy)-4-thia-2(E)-heptenoic acid (1.26 g, yield 98%).
IR (KBr) υ: 2917, 2850, 1735, 1664, 1579, 1469, 1405, 1267, 1195, 1172, 1110 cm$^{-1}$
$^1$H-NMR (CDCl$_3$) δ:0.88 (6H, t, J=6.8 Hz), 1.25 (48H, s), 1.50–1.70 (4H, m), 2.25–2.40 (4H, m), 3.07 (2H, d, J=6.6 Hz), 4.18 (1H, dd, J=12.5, 5.4 Hz), 4.33 (1H, dd, J=12.0, 4.2 Hz), 5.22 (1H, m), 5.89 (1H, d, J=15.2 Hz), 7.74 (1H, d, J=15.2 Hz)

REFERENCE EXAMPLE 14

6,7-bis(palmitoyloxy)-4-thia-2(Z)-heptenoic acid t-butyl ester

To a solution of 6,7-dihydroxy-4-thia-2(Z)-heptenoic acid t-butyl ester as obtained in Reference Example 11 (308 mg) and triethylamine (355 mg) in dichloromethane (10 ml), palmitoyl chloride (795 mg) was added, followed by stirring at room temperature for I hour. The mixture was diluted with dichloromethane, washed with water, and dried over sodium sulfate, followed by solvent concentration. The resulting residue was purified by silica gel column chromatography (n-hexane:ethyl acetate:dichloromethane=40:1:1) to yield the title compound (460 mg, yield 49%) as a colorless crystal.
IR (KBr) υ: 2920, 2850, 1740, 1690, 1570, 1460, 1360, 1230, 1150 cm$^{-1}$
$^1$H-NMR (CDCl$_3$)δ:0.88 (6H, t, J=6.8 Hz), 1.26 (48H, s), 1.50 (9H, s), 1.50–1.70 (4H, m), 2.32 (4H, t, J=7.4 Hz), 2.95 (2H, d, J=6.4 Hz), 4.20 (1H, dd, J=12.0, 5.4 Hz), 4.38 (1H, dd, J=12.0, 3.6 Hz), 5.14 (1H, m), 5.80 (1H, d, J=10.2 Hz), 7.00 (1H, d, J=10.2 Hz)

REFERENCE EXAMPLE 15

6,7-bis(palmitoyloxy)-4-thia-2(Z)-heptenoic acid

To a solution of 6,7-bis(palmitoyloxy)-4-thia-2(Z)-heptenoic acid t-butyl ester as obtained in Reference Example 14 (450 mg) in dichloromethane (1 ml), trifluoroacetic acid (4 ml) was added, followed by stirring at room temperature for 1 hour. The solvent was concentrated under reduced pressure to yield 6,7-bis(palmitoyloxy)-4-thia-2(Z)-heptenoic acid (406 mg, yield 98%).
IR (KBr) υ: 2919, 2850, 1733, 1658, 1564, 1467, 1261, 1191, 1170, 1114 cm$^{-1}$
$^1$H-NMR (CDCl$_3$) 3:0.88 (6H, t, J=6.8 Hz), 1.25 (48H, s), 1.50–1.70 (4H, m), 2.32 (4H, t, J=7.2 Hz), 2.98 (2H, d, J=6.4 Hz), 4.19 (1H, dd, J=12.0, 5.4 Hz 4.36 (1H, dd, J=12.0, 3.8

Hz), 5.14 (1H, m), 5.91 (1H, d, J=10.0 Hz), 7.25 ( 1H, d, J=10.0 Hz)

REFERENCE EXAMPLE 16

N-vinylsulfonyl-Gly-Gly-Gly-Glu(O$^t$BU)$_2$

Gly-Gly-Gly-Glu(O$^t$Bu)$_2$·hydrochloride (1.168 g, 2.5 mM) was dissolved in dichloromethane (15 ml) and triethylamine (1.4 ml, 10 ml). To this solution, a solution of chloroethylsulfonyl chloride (619 mg, 3.75 mM) in dichloromethane (15 ml) was added, followed by stirring under ice cooling conditions for 30 minutes. The reaction mixture was poured over ice water (20 ml) containing acetic acid (0.4 ml); the organic layer was separated, dried over sodium sulfate, purified by silica gel column (20 g) (chloroform-methanol (3:47)) to yield the title compound (1.086 g, yield 83%) as a colorless solid.
IR (Neat) υ: 3330, 2980, 2930, 1730, 1660, 1540, 1480, 1455, 1450, 1420, 1370, 1330, 1250, 1150, 1025, 970, 845, 750 cm$^{-1}$
$^1$H-NMR (CDCl$_3$)δ:1,439 (9H, s), 1.461 (9H, s), 1.80–2.25 (2H, m), 2.296 (2H, t, J=6.8 Hz), 3.726 (2H, d, J=5.8 Hz), 4.004 (4H, m), 4.430 (1H, m), 6.002 (2H, d, J=9.2 Hz), 6.264 (1H, d, J=16.6 Hz), 6.563 (1H, dd, J=9.2, 16.6 Hz), 7.115 (1H, d, J=7.8 Hz), 7.385 (1H, t, J=5.0 Hz), 7.706 (1H, t, J=5.0 Hz)

REFERENCE EXAMPLE 17

N-(vinylsulfonyl)-N-t-butyloxycarbonyl-Gly-Gly-Gly-Glu(O$^t$Bu)$_2$

N-vinylsulfonyl-Gly-Gly-Gly-Glu(O$^t$Bu)$_2$ as obtained in Reference Example 16 (324 mg, 0.623 mM) was dissolved in tetrahydrofuran (2 ml) and pyridine (1 ml). To this solution, a solution of di-t-butyl dicarbonate (163 mg, 0.75 mM) in tetrahydrofuran (1 ml) was added, followed by stirring at room temperature for 30 minutes. The reaction mixture was concentrated to dryness under reduced pressure; the residue was purified by silica gel column (5 g) (chloroform-methanol (49:1)) to yield the title compound (161 mg, yield 2.8%) as a colorless solid.
IR (Neat) υ: 3330, 3070, 2970, 2930, 1730, 1660, 1540, 1365, 1250, 1145, 1070, 1020, 845 cm$^{-1}$
$^1$H-NMR (CDCl$_3$)δ:1.433 (9H, s), 1.467 (9H, s), 1.487 (9H, s), 1.80–2.22 (2H, m), 2.289 (1H, t, J=6.4 Hz), 2.306 (1H, t, J=7.4 Hz), 3.982 (2H, d, J= 5.4 Hz) 4.024 (2H, d, J=5.2 Hz), 4.438 (2H, s), 4.463 (1H, m), 6.135 (1H, d, J= 9.6 Hz), 6.430 (1H, d, J=16.6 Hz), 6.70–6.92 (3H, m), 7.01 (1H, dd, J=9.8, 16.6 Hz)

REFERENCE EXAMPLE 18

N-( 5,6-dihydroxy-3thiahexanesulfonyl)-N-t-butyloxycarbonyl-Gly-Gly-Gly-Glu(O$^t$Bu)$_2$ N-(vinylsulfonyl)-N-t-butyloxycarbonyl-Gly-Gly-Gly-Glu(O$^t$Bu)$_2$ as obtained in Reference Example 17 (161 mg, 0.267 mM) was dissolved in a mixture of N,N-dimethylformamide (1 ml) and pyridine (1 ml). To this solution, 1-thioglycerol (72 mg, 0.667 mM) was added, followed by stirring at 80° C. for 5 hours. After addition of chloroform (20 ml), H$_2$O (20 ml) and saturated saline (1 ml) and vigorous shaking, the organic layer was separated to yield the title compound (192 mg, yield 100%) as a colorless solid.

IR (KBr) υ: 3330, 2975, 2925, 1730, 1665, 1530, 1365, 1250, 1150 cm$^{-1}$
$^1$H-NMR (CDCl$_3$) δ:1.444 (9H, s), 1.468 (9H, s), 1.520 (9H, s), 1.65–2.20 (4H, m), 2.293 (1H, t, J=7.0 Hz), 2,306 (1H, t, J=7.8 Hz), 2.686 (2H, t, J=7.4 Hz), 3.043 (2H, dd, J=6.2, 10.2 Hz), 3.5–4.15 (9H, m), 4.434 (2H, s), 4.457 (1H, m), 7.072 (1H, d, J =7.8 Hz), 7.10–7.40 (2H, bs)

REFERENCE EXAMPLE 19

N-[6-(vinylsulfonylamino)hexanoyl]glutamic acid di-t-butyl ester (6-aminohexanoyl)Glu(O$^t$Bu)$_2$ (574 mg, 1.5 mM) and triethylamine (0.65 ml, 4.6 mM) were dissolved in dichloromethane (9.25 ml). To this solution, a solution of chloroethylsulfonyl chloride (382 mg, 2.31 mM) in dichloromethane (9.25 ml) was added drop by drop over a period of about 15 minutes, followed by stirring for 30 minutes. To the reaction mixture, ice water (12 ml) and then acetic acid (0.24 ml) were added, followed by vigorous stirring, after which the chloroform layer was separated and then concentrated to dryness under reduced pressure. The residue was purified by silica gel column (15 g) (methanol-chloroform (3:197)) to yield the title compound (600 mg, yield 86.6%) as a colorless solid.
IR (Neat) υ: 3570, 3290, 2980, 2930, 2860, 1730, 1650, 1530, 1475, 1450, 1420, 1390, 1360, 1325, 1250, 1150, 1080, 960, 840,734 cm$^{-1}$
$^1$H-NMR (CDCl$_3$) δ: 1.386 (4H, m), 1.447 (9H, s), 1.471 (9H, s), 1.50–2.15 (6H, m), 2.246 (4H, m), 3.037 (2H, t, J=6.8 Hz), 4.480 (1H, m), 4.720 (1H, bs) 5.927 (1H, d, J=9.6 Hz), 6.233 (1H, d, J=18.6 Hz), 6.241 (1H, bs), 6.519 (1H, dd, J=9.6, 18.6 Hz)

REFERENCE EXAMPLE 20

6-[N-(vinylsulfonyl)-N-(t-butyloxycarbonyl)amino]-hexanoylglutamic acid di-t-butyl ester N-[6-(vinylsulfonylamino)hexanoyl]glutamic acid di-t-butyl ester as obtained in Reference Example 19 (660 mg, 1.3 mM) and di-t-butyl dicarbonate (425 mg, 1.94 mM) were dissolved in pyridine (3 ml), followed by stirring at room temperature for 1 hour. The reaction mixture was concentrated to dryness under reduced pressure; the residue was purified by silica gel column (7 g) (hexane-chloroform (1:1)) to yield the title compound (617 mg, yield 84.3%) as a colorless solid.
IR (Neat) υ: 3380, 2980, 2930, 1725, 1650, 1530, 1470, 1450, 1360, 1280, 1250, 1145 cm$^{-1}$
$^1$H-NMR (CDCl$_3$) δ:1.333 (2H, m), 1.443 (9H, s), 1.468 (9H, s), 1.512 (9H, s), 1.659 (4H, m), 1.80–2.13 (2H, m), 2.13–2.40 (4H, m), 3.660 (2H, t, J= 7.6 Hz) 4.571 (1H, m), 6.084 (1H, d,J=9.8 Hz), 6.131 (1H, d,J=7.6 Hz), 6,362 (1H, d, J=16.6 Hz), 6.862 (1H, dd, J=9.8, 16.6 Hz)

REFERENCE EXAMPLE 21

6-[N-(5,6-dihydroxy-3-thiahexanesulfonyl)-N-(t-butyloxycarbonyl)amino] -hexanoylglutamic acid di-t-butyl ester To 6-[N-(vinylsulfonyl)-N-(t-butyloxycarbonyl)amino]-hexanoylglutamic acid di-t-butyl ester as obtained in Reference Example 20 (200 mg, 0.22 mM), (2S)-1-thioglycerol (49 mg, 0.45 mM) and then triethylamine (18 mg) were added, followed by stirring for 2 hours. The reaction mixture was concentrated to dryness under reduced pressure; the residue was purified by silica gel column (5 g) (methanol-chloroform (1:99)) to yield the title compound (174 mg, yield 72.1%) as a colorless solid.
IR (Neat) υ: 3400, 2970, 2920, 2860, 1720, 1640, 1540, 1450, 1390, 1365, 1345, 1275, 1520, 1145, 1130 cm$^{-1}$
$^1$H-NMR (CDCl$_3$) δ:1.366 (2H, m), 1.447 (9H, s), 1.470 (9H, s), 1.536 (9H, s),1.667 (4H, m), 1.80–2.40 (8H, m), 2.696 (2H, t, J=7.8 Hz), 2.964 (2H, t, J=7.8 Hz), 3.50–3.80 (7H, m), 3.855 (1H, m), 4.454 (1H, m), 6.301 (1H, d, J=7.8 H

REFERENCE EXAMPLE 22

6,7-dihydroxy-4-thiaheptanoic acid t-butyl ester

Acrylic acid t-butyl ester (15 g) and thioglycerol (15 g) were mixed together in the absence of solvent. To the reaction mixture, one drop of triethylamine was added to cause an exothermic reaction, yielding a homogeneous reaction mixture, which was then diluted with ethyl acetate, washed with water and dried, followed by solvent concentration under reduced pressure, to yield the title compound (25.79 g, yield 93%) as a colorless oily substance.
IR (Neat) υ: 3380, 2970, 2920, 1720, 1360, 1245, 1145 cm$^{-1}$
$^1$H-NMR (CDCl$_3$)δ:1.46 (9H, s), 2.40–2.85 (7H, m), 3.15–3.30 (1H, m), 3.50–3.65 (1H, m), 3.70–3.90 (2H, m)

REFERENCE EXAMPLE 23

6,7,bis(palmitoylxy)-4-thiaheptanoic acid t-butyl ester

To a solution of 6,7-dihydroxy-4-thiaheptanoic acid t-butyl ester as obtained in Reference Example 22 (2.0 g) and dimethylaminopyridine (2.27 g) in dichloromethane (20 ml), palmitoyl chloride (4.66 g) was added followed by stirring at room temperature for 1 hour. The mixture was concentrated; the resulting residue was purified by silica gel column chromatography (nhexane:ethyl acetate=10:1) to yield the title compound (4.848 g, yield 80%) as a colorless oily substance.
IR (Neat) υ: 2920, 2850, 1725, 1455, 1360, 1245, 1150 cm$^{-1}$
$^1$H-NMR (CDCl$_3$) δ:0.88 (6H, t, J=6.8 Hz), 1.26 (48H, s), 1.45 (9H, s), 1.50–1.70 (4H, m), 2.31 (4H, t, J=7.4 Hz), 2.52 (2H, t, J=6.8 Hz), 270–2.85 (4H, m), 4.19 (1H, dd, J=12.0, 5.8 Hz), 4.36 (1H, dd, J=12.0, 3.4 Hz), 5.16 (1H, m)

REFERENCE EXAMPLE 24

6,7-bis(palmitoyloxy)-4-thiaheptanoic acid

To a solution of 6,7-bis(palmitoyloxy)-4-thiaheptanoic acid t-butyl ester as obtained in Reference Example 23 (4.84 g) in dichloromethane (1 ml), trifluoroacetic acid (4 ml) was added, followed by stirring at room temperature for 1 hour. The reaction mixture was concentrated; the residue was washed with hexane to yield the title compound (4.46 g, yield 100%) as a colorless powder.

REFERENCE EXAMPLE 25

Fmoc-Glu(OBu$^t$)-Glu(OBu$^t$)$_2$

A solution of N-(9-fluorenylmethyloxycarbonyl)glutamic acid γ-t-butyl ester (3.0 g), glutamic acid di-t-butyl ester hydrochloride (2.50 g), DEPC (1.73 g) and triethylamine (2.13 g) in dimethylformamide (30 ml) was stirred at room temperature for 1 hour. The solvent was concentrated; the resulting residue was purified by silica gel column chromatography (n-hexane:ethyl acetate = 4:1) to yield the title compound (4.328 g, yield 92%) as a colorless syrup.
IR (Neat) υ: 3300, 2930, 1727, 1710, 1660, 1533, 1450, 1367, 1253, 1153 cm$^{-1}$ $^1$H-NMR (CDCl$_3$) δ:1.42 (9H, s), 1.46 (18H, s), 1.80–2.50 (8H, m), 4.10–4.50 (5H, m), 5.74 (1H, d, J=7.2 Hz), 6.96 (1H, d, J=7.2 Hz), 7.25–7.45 (4H, m), 7.60 (2H, d, J=7.2 Hz), 7.76 (2H, d, J=6.8 Hz)

REFERENCE EXAMPLE 26

Glu(OBu$^t$)-Glu(OBu$^t$)$_2$

To a solution of Fmoc-Glu(OBu$^t$)-Glu(OBu$^t$)$_2$ as obtained in Reference Example 25 (4.32 g) in dichloromethane (10 ml)-piperidine (10 ml) was stirred at room temperature overnight. The mixture was concentrated; the resulting residue was purified by silica gel column chromatography (chloroform) to yield the title compound (2.51 g, yield 87%) as a colorless oily substance.
IR (Neat) υ: 3320, 2980, 2930, 1730, 1675, 1505, 1455, 1390, 1365, 1250, 1150 cm$^{-1}$
1H-NMR (CDCl$_3$) δ:1.42 (9H, s), 1.45 (9H, m), 1.46 (9H, s), 1.80–2.40 (8H, m), 3.45 (1H, q, J=7.0 Hz), 3.73 (2H, brs), 4.42 (1H, m), 7.75 (1H, d, J=8.2 Hz)

REFERENCE EXAMPLE 27

6,7dihydroxy-3methyl-4-thiaheptanoic acid t-butyl ester

To thioglycerol (0.835 ml), t-butyl crotonate (10 ml) and triethylamine (1 ml) were added, followed by stirring at 60° C. for 48 hours. After cooling and addition of water, the reaction mixture was extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off, to yield the title compound (1.82 g, yield 73%) as a colorless oily substance.
IRυ$_{max}^{neat}$ cm$^{-1}$: 3400, 1725
$^1$H-NMR(CDCl$_3$)δ: 1.34 (3H, d, J=6.8 Hz), 1.47 (9H, s), 2.34–2.84 (4H, m), 3.11–3.34 (1H, m), 3.50–3.93 (3H, m)

REFERENCE EXAMPLE 28

6,7-bis(palmitoyloxy)-3-methyl-4-thiaheptanoic acid t-butyl ester

To a solution of 6,7-dihydroxy-3-methyl-4-thiaheptanoic acid t-butyl ester as obtained in Reference Example 27 (500 mg) in chloroform (30 ml), triethylamine (5.6 ml), palmitoyl chloride (5.50 g) and dimethylaminopyridine (5 mg) were added, followed by stirring at room temperature for 48 hours. After addition of water, the reaction mixture was extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The residue was purified by silica gel chromatography (hexane:ethyl acetate=1:1) to yield the title compound (1.43 g, yield 99%) as a colorless oily substance.
IRυ$_{max}^{neat}$ cm$^{-1}$: 1730
$^1$H-NMR(CDCl$_3$)δ: 0.88 (6H, t, J=6.8 Hz), 1.05–1.41 (51H, m), 1.46 (9H, s), 1.52–1.72 (4H, m), 2.25–3.32 (9H, m), 4.12–4.42 (2H, m), 5.07–5.22 (1

REFERENCE EXAMPLE 29

6,7-bis(palmitoyloxy)-3,methyl-4-thiaheptanoic acid

To a solution of 6,7-bis(palmitoyloxy)-3-methyl-4-thiaheptanoic acid t-butyl ester as obtained in Reference Example 28 (1.43 g) in chloroform (4 ml), trifluoroacetic acid (4 ml) was added, followed by stirring at room temperature for 4 hours. The mixture was concentrated to yield the title compound (1.31 g, yield 100%) as a colorless solid.
IR$\nu_{max}^{KBr}$ cm$^{-1}$: 3450, 1730
$^1$H-NMR (CDCl$_3$)δ:0.88 (6H, t, J=6.6 Hz), 1.03–1.50 (51H, m), 1.50–1.74 ( 4H, m), 2.32 (4H, t, J=7.8 Hz), 2.37–2.86 (3H, m), 2.76 (2H, d, J=6.6 Hz), 4.18 ( 1H, dd, J=4.6, 11.8 Hz), 4.37 (1H, dd, J=3.4, 11.8 Hz), 5.07–5.23 (1H, m)

REFERENCE EXAMPLE 30

4-(vinylsulfonylaminomethyl)benzoyl-glutamic acid di-t-butyl ester 4-(aminomethyl)benzoyl-glutamic acid di-t-butyl ester hydrochloride as obtained in Reference Example 37 (255 mg) and triethylamine (0.27 ml) were dissolved in dichloromethane (4 ml). To this solution, a solution of chloroethylsulfonyl chloride (161 mg) in dichloromethane (4 ml) was added drop by drop under ice cooling conditions over a period of about 15 minutes, followed by stirring at the same temperature for 30 minutes. To the mixture, ice water (12 ml). and chloroform (10 ml) were added, followed by vigorous stirring, after which the organic layer was separated, and concentrated to dryness under reduced pressure. The resulting residue was purified by silica gel column chromatography (methanol:chloroform=1:99) to yield the title compound (172 mg, yield 58.3%) as a colorless solid.
IR (Neat)$\nu$: 3300, 2970, 2920, 1725, 1640, 1610, 1570, 1530, 1500, 1450, 1360, 1320, 1250, 1145, 1090, 1065, 840, 850 cm$^{-1}$
$^1$H-NMR (DMSO-d$_6$)δ:1.423 (9H, s), 1.495 (9H, s), 1.88–2.28 (2H, m), 2.28– 2.54 (2H, m), 4.272 (2H, d, J=6.6 Hz), 4.655 (1H, m), 4.820 (1H, bs), 5.941 (1d, J=9.6 Hz), 6.266 (1H, d, J=16.4 Hz), 6.496 (1H, dd, J=9.6, 16.4 Hz), 7.091 (1H, d, J=6.6 Hz), 7.390 (2H, d, J=8.4 Hz), 7.808 (2H, d, J=8.4 Hz)

REFERENCE EXAMPLE 31

4-(N-vinylsulfonyl-N-t-butyloxycarbonylaminomethyl)benzoylglutamic acid di-t-butyl ester 4-(vinylsulfonylaminomethyl)benzoyl-glutamic acid di-t-butyl ester as obtained in Reference Example 30 (172 mg) and di-t-butyl dicarbonate (118 mg) were dissolved in pyridine (1 ml), followed by stirring at room temperature for 1 hour. The organic layer was concentrated to dryness under reduced pressure; the resulting residue was purified by silica gel column chromatography (chloroform:n-hexane=1:1) to yield the title compound (145 mg, yield 70.3%) as a colorless solid.
IR (neat) $\nu$: 3350, 2980, 2925, 1725, 1650, 1610, 1575, 1530, 1500, 1475, 1455, 1390, 1360, 1300, 1280, 1140 cm$^{-1}$
$^1$H-NMR (CDCl$_3$)δ:1.418 (9H, s), 1.469 (9H, s), 1.493 (9H, s), 1.95–2.28 ( 2H, m), 2.28–2.60 (2H, m), 4.662 (1H, m), 4.914 (2H, s), 6.016 (1H, d, J=10.0 Hz), 6.307 (1H, d, J=16.4 Hz), 6.755 (1H, dd, J= 10.0, 16.4 Hz), 6.014 (1H, d, J=7.8 Hz), 7.408 (2H, d, J=8.2 Hz), 7.797 (2H, d, J=8.4 Hz)

REFERENCE EXAMPLE 32

4-(N-(2-((2R)-2,3-dihydroxypronylthio)ethylsulfonyl)-N-t-butyloxycarbonylaminomethyl)benzoyl-glutamic acid di-t-butyl ester To 4-(N-vinylsulfonyl-N-t-butyloxycarbonylaminomethyl)benzoylglutamic acid di-t-butyl ester as obtained in Reference Example 31 (145 mg) and (2R)-3-mercapto-1,2-propanediol (34 mg), triethylamine (18 mg) was added, followed by stirring at room. temperature for 30 minutes. To the reaction mixture, chloroform (20 ml) and saturated saline (20 ml) were added, followed by vigorous shaking. The chloroform layer was then separated, dried over sodium sulfate, and concentrated to dryness under reduced pressure. The resulting residue was purified by silica gel column chromatography (methanol:chloroform=1:99) to yield the title compound (0.151 g, yield 88.8%) as a colorless solid.
IR (neat) $\nu$: 3380, 2980, 2980, 2870, 1725, 1645, 1570, 1535, 1500, 1470, 1450, 1410, 1390, 1260, 1350, 1300, 1280, 1250, 1140 cm$^{-1}$
$^1$H-NMR (CDCl$_3$)δ:1.431 (9H, s), 1.498 (9H, s), 1.545 (9H, s), 1.90–2.28 (2H, m), 2.28–2.60 (6H, m), 2.860 (1H, bs), 3.045 (1H, bs), 8.40–3.70 (5H, m), 4.689 (1H, m), 4.918 (2H, s), 7.279 (1H, d, J=7.0 Hz), 7.479 (2H, d, J=8.2 Hz), 7.816 (2H, d, J=8.2 Hz)

REFERENCE EXAMPLE 33

6,7-bis(12-phenyldodecanoyloxy)-4-thiaheptanoic acid t-butyl ester

To a solution of 6,7-dihydroxy-4-thiaheptanoic acid t-butyl ester as obtained in Reference Exampl.e 22 (500 mg), 12-phenyldodecanoic acid as synthesized by the method of Goto et al. [Nippon Kagaku Zasshi, Vol. 88, p. 102 (1967)] (1.23 g) and 4-dimethylarninopyridine (650 mg) in dichloromethane (10 ml)-acetonitrile (10 ml), diisopropylcarbodiimide (670 mg) was added, followed by stirring at room temperature for I day. After solvent concentration under reduced pressure, the resulting residue was purified by silica gel column chromatography (n-hexane:ethyl acetate=3:1) to yield the title compound (1.221 g, yield 77%) as a colorless oily substance.
IR (Neat) $\nu$: 2920, 2850, 1730, 1490, 1450, 1360, 1240, 1150, 690 cm$^{-1}$
$^1$H-NMR (CDCl$_3$) 3:1.26 (28H, s), 1.45 (9H, s), 1.50–1.70 (SH, m), 2.31 (4H, t, J=7.2 Hz), 2.45–2.65 (6H, m), 2.70–2.85 (4H, m), 4.18 (1H, dd, J=12.0, 6.0 4.36 (1H, dd, J=12.0, 3.5 Hz), 5.17 (1H, m), 7.10–7.30 (10H, m)

REFERENCE EXAMPLE 34

6,7-bis(12-phenyldodecanoyloxy)-4-thiaheptanoic acid

A solution of 6,7-bis(12-phenyldodecanoyloxy)-4-thiaheptanoic acid t-butyl ester as obtained in Reference Example 33 (1.22 g) in dichloromethane (2 ml)-trifluoroacetic acid (6 ml) was stirred at room temperature for 2 hours, after which the solvent was distilled off under reduced pressure, to yield the title compound (1.12 g, yield 99%) as a colorless oily substance.
IR (Neat) $\nu$: 2920, 2850, 1735, 1710, 1450, 1240, 1160, 695 cm$^{-1}$
$^1$H-NMR (CDCl$_3$) 3:1.26 (28H, s), 1.50–1.75 (8H, m), 2.31 (4H, t, J=7.5 Hz), 2.55–2.90 (10H, m), 4.17 (1H, dd, J=12.0, 5.8 Hz), 4.36 (1H, dd, J=12.0, 3.8 Hz), 5.15 (1H, m), 7.10–7.35 (10H, m)

REFERENCE EXAMPLE 35

4-(benzyloxycarbonylaminomethyl)benzoic acid

To a solution of 4-(aminomethyl)benzoic acid (25 g) in a 2N aqueous solution of sodium hydroxide (100 ml), a solution of benzyloxycarbonyl chloride (33.8 g) in tetrahydrofuran (50 ml) was added drop by drop under ice cooling conditions, followed by stirring at room temperature for 2 hours. The resulting precipitate was collected by filtration, washed with water, 1N hydrochloric acid and ether and dried under reduced pressure to yield the title compound (10.5 g, yield 22%) as a colorless powder.
IR (KBr) $\upsilon$: 3313, 1684, 1612, 1529, 1430, 1322, 1292, 1253, 1054, 761, 696 cm$^{-1}$
$^1$H-NMR (CDCl$_3$) 3:4.26 (2H, d, J=6.2 Hz), 5.05 (2H, s), 7.31 (2H, d, J= 8.0 Hz), 7.36 (5H, s), 7.87 (2H, d, J=8.0 Hz)

REFERENCE EXAMPLE 36

4-(benzyloxycarbonylaminomethyl)benzoyl-glutamic acid di-t-butyl ester

To a solution of 4-(benzyloxycarbonylaminomethyl)benzoic acid as obtained in Reference Example 35 (1.0 g), glutamic acid di-t-butyl ester hydrochloride (1.15 g) and DEPC (860 mg) in dimethylformamide (20 ml), triethylamine (1.06 g) was added drop by drop, followed by stirring at room temperature for 1 hour. After solvent concentration under reduced pressure, the resulting residue was purified by silica gel column chromatography (n-hexane:ethyl acetate= 2:1) to yield the title compound (1.86 g, yield 100%) as a colorless wax-like substance.
IR (Neat) $\upsilon$: 1720, 1700, 1640, 1530, 1500, 1360, 1250, 1145 cm$^{-1}$
$^1$H-NMR (CDCl$_3$) 8:1.42 (9H, s), 1.49 (9H, s), 1.90–2.55 (4H, m), 4.43 (2H, d, J=6.0 Hz), 4.66 (1H, m), 5.15 (3H, s), 7.01 (1H, d, J=7.0 Hz), 7.30–7.40 (7H, m), 7,79 (2H, d, J=8.4 Hz)

REFERENCE EXAMPLE 37

4-(aminomethyl)benzoyl-glutamic acid di-t-butyl ester hydrochloride

A suspension of 4-(benzyloxycarbonylaminomethyl)benzoyl-glutamic acid di-t-butyl ester as obtained in Reference Example 36 (1.85 g) and 10% palladium carbon (200 mg) in methanol (13 ml) was subjected to catalytic reduction with hydrogen (80 ml). After the catalyst was filtered out, a 4N solution of hydrochloric acid in ethyl acetate (0.88 ml) was added to the flitrate, followed by solvent concentration, to yield the title compound as an amorphous substance.
IR (KBr) $\upsilon$: 3400, 3000, 1731, 1650, 1540, 1506, 1369, 1235, 1151 cm$^{-1}$
$^1$H-NMR (CDCl$_3$) 8:1.41 (9H, s), 1.48 (9H, s), 1.90–2.40 (4H, m), 4.13 (2H, s), 4.59 (1H, m), 7.48 (2H, d, J=8.0 Hz), 7.69 (3H, d, J=8.0 Hz)

REFERENCE EXAMPLE 38

(2R,6R) 4-[2-(9-fluorenylmethyloxycarbonylamino)-6,7-bis (palmitoyloxy)-4-thiaheptanoylaminomethyl]benzoyl-glutamic acid di-t-butyl ester A solution of(2R,6R) 6,7-bis(palmitoyloxy)-2-(9-fluorenyl-methyloxycarbonylamino)- 4-thiaheptanoic acid as synthesized by the method of J. W. Metzger et al. [International Journal of Peptide Protein Research, Vol. 38, p. 545 (1991)] (200 mg), 4-(aminomethyl)benzoyl-glutamic acid di-t-butyl ester hydrochloride as obtained in Reference Example 37 (106 mg), DEPC (55 mg) and triethylamine (70 mg) in dimethylformamide (10 ml) was stirred at room temperature for 30 minutes. After solvent concentration under reduced pressure, the resulting residue was purified by silica gel column chromatography (n-hexane:ethyl acetate=2:1) to yield the title compound (247 mg, yield 87%) as a colorless wax-like substance.
IR (Neat) $\upsilon$: 3300, 2920, 2850, 1730, 1660, 1530, 1500, 1445, 1360, 1240, 1150 cm$^{-1}$ $^1$H-NMR (CDCl$_3$)δ:0.88 (6H, t, J=6.8 Hz), 1.25 (48H, m), 1.42 (9H, s), 1.49 (9H, s), 1.40–1.65 (4H, m), 1.95–2.50 (8H, m), 2.77 (2H, d, J=6.6 Hz), 2.90–3.00 (2H, m), 4.05–4.55 (5H, m), 4.66 (1H, m), 5.24 (1H, m), 5.78 (1H, br), 6.98 (1H, br), 7.02 (1H, d, J=7.4 Hz), 7.25–7.45 (6H, m), 7.58 (2H, d, J=7.4 Hz), 7.76 (2H, d, J=7.2 Hz), 7.78 (2H, d, J=8.4 Hz)

REFERENCE EXAMPLE 39

(2R,6R) 4 -[2-amino-6,7-bis(palmitoyloxy)-4-thiaheptanoylaminomethyl] benzoyl-glutamic acid di-t-butyl ester A solution of (2R,6R) 4-[2-(9-fluorenylmethyloxycarbonylamino)-6,7-bis(palmitoyloxy)- 4-thiaheptanoylaminomethyl]benzoyl-glutamic acid di-t-butyl ester as obtained in Reference Example 38 (243 mg) in dichloromethane (0.5 ml)-piperidine (2 ml) was stirred at room temperature for 30 minutes. After solvent concentration under reduced pressure, the resulting residue was purified by silica gel column chromatography (n-hexane:ethyl acetate=3:1 to 1:3) to yield the title compound (195 mg, yield 97%) as a colorless wax-like substance.
IR (Neat) $\upsilon$: 3350, 2920, 2850, 1730, 1650, 1535, 1520, 1500, 1460, 1450, 1360, 1250, 1150 cm$^{-1}$
$^1$H-NMR (CDCl$_3$) 3:0.88 (6H, t, J=6.8 Hz), 1.25 (48H, s), 1.42 (9H, s), 1.49 (9H, s), 1.45–1.65 (4H, m), 1.73 (2H, brs), 1.90–2.50 (8H, m), 2.75 (2H, d, J=6.4 Hz), 2.81 (1H, dd, J=13.4, 8.4 Hz), 3.14 (1H, dd, J=13.4, 3.8 Hz), 3.57 (1H, dd, J=8.4, 4.0 Hz), 4.14 (1H, dd, J=12.0, 6.2 Hz), 4.36 (1H, dd, J=12.0, 3.2 Hz), 4.49 (2H, d, J=6.2 Hz), 4.66 (1H, m), 5.16 (1H, m), 7.02 (1H, d, J=7.4 Hz), 7.35 (2H, d, J=8.2 Hz), 7.79 (2H, d, J=8.2 Hz), 7.83 ( 1H, br)

REFERENCE EXAMPLE 40

6,7-dihydroxy-2-methyl-4-thiaheptanoic acid t-butyl ester

To thioglycerol (0.835 ml), t-butyl methacrylate (10 ml) and triethylamine (1 ml) were added, followed by stirring at 60° C. for 48 hours. After cooling and addition of water, the reaction mixture was extracted with chloroform. The extract was washed with a 5% aqueous solution of citric acid, a saturated aqueous solution of sodium hydrogen carbonate and saturated saline, and dried over anhydrous sodium sulfate, and the solvent was distilled off, to yield the title compound (2.11 g, yield 84%) as a colorless oily substance.
IR$\upsilon_{max}^{neat}$ cm$^{-1}$: 3400, 1720
$^1$H-NMR (CDCl$_3$)δ:1.21 (3H, d, J=6.6 Hz), 1.47 (9H, s), 2.50–2.90 (5H, m), 3.50–3.63 (1H, m), 3.68–3.88 (2H, m)

REFERENCE EXAMPLE 41

6,7-bis(palmitoyloxy)-2-methyl-4-thiaheptanoic acid t-butyl ester

To a solution of 6,7-dihydroxy-2-methyl-4-thiaheptanoic acid t-butyl ester as obtained in Reference Example 40 (500 mg) in chloroform (30 ml), triethylamine (5.6 ml), palmitoyl chloride (5.50 g) and dimethylaminopyridine (5 mg) were added, followed by stirring at room temperature for 48 hours. After addition of water, the reaction mixture was extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (hexane:ethyl acetate=1:1) to yield the title compound (1.33 g, yield 91%) as a colorless oily substance.
IR$\upsilon_{max}^{neat}$ cm$^{-1}$ 1730, 1640
$^1$H-NMR (CDCl$_3$)δ:0.88 (6H, t, J=6.8 Hz), 1.03–1.40 (51H, m), 1.45 (9H, s), 1.50–1.70 (4H, m), 2.31 (4H, t, J=7.4 Hz), 2.45–2.90 (5H, m), 4.18 (1H, dd, J=5.8, 11.8 Hz), 4.36 (1H, dd, J=3.4, 11.8 Hz), 5.08–5.23 (1H, m)

REFERENCE EXAMPLE 42

6,7-bis(palmitoyloxy)-2-methyl-4-thiaheptanoic acid

To a solution of 6,7-palmitoyloxy-2-methyl-4-thiaheptanoic acid t-butyl ester as obtained in Reference Example 41 (1.33 g) in chloroform (4 ml), trifluoroacetic acid (4 ml) was added, followed by stirring at room temperature for 4 hours. The reaction mixture was concentrated to yield the title compound (1.23 g, yield 100%) as a colorless solid.
IR$\upsilon_{max}^{KBr}$ cm$^{-1}$: 1730
$^1$H-NMR (CDCl$_3$) 3:0.88 (6H, t, J=6.8 Hz), 1.03–1.48 (51H, m), 1.48–1.72 (4 H, m), 2.31 (4H, t, J=7.8 Hz), 2.32 (2H, t, J=7.8 Hz), 2.62–3.00 (5H, m), 4.16 (1H, dd, J=6.0, 12.0 Hz), 4.37 (1H, dd, J=3.2, 12.0 Hz), 5.07–5.22 (1H, m)

REFERENCE EXAMPLE 43

3,4-epoxy-2-butanol 3-buten-2-ol (10.05 g) was dissolved in methylene chloride (200 ml). To this solution, m-chloroperbenzoic acid (28.4 g) was added under ice cooling conditions, followed by stirring at room temperature for I day. After the separating white solid was filtered out, the flitrate was concentrated under reduced pressure (20 mmHg, 65° C.) to yield the title compound (4.55 g, yield 4%) as a colorless oily substance.
IR (Neat) υ: 3412, 3000, 2933, 2881, 1650, 1450, 1371, 1288, 1101, 974, 935, 87 cm$^{-1}$
$^1$H-NMR (CDCl$_3$)δ:4.00 (1H, m), 3.62 (1.3H, m), 3.05–2.94 (2.5H, m), 2.85–2.68 (4.7H, m), 1.28 (6.7H, dd, J=8.8, 6.6 Hz)

REFERENCE EXAMPLE 44

6,7-dihydroxy-4-thiaoctanoic acid methyl ester

To a solution of 3,4-epoxy-2-butanol as obtained in Reference Example 43 (1.13 g) in methylene chloride (4 ml), methyl 3-mercaptopropionate (2.00 ml) and sodium methylate (260 µl) were added under ice cooling conditions, followed by stirring at room temperature for 1 day. To the reaction mixture, 1N hydrochloric acid was added, and the mixture was extracted with ethyl acetate; the solvent was distilled off under reduced pressure. The resulting residue was purified by silica gel column chromatography (ethyl acetate:hexane=2:1) to yield the title compound (1.47 g, yield 55%) as a colorless oily substance.
IR (Neat) υ:3419, 2972, 2927, 1732, 1439, 1362, 1252, 1140, 1055, 2985 cm$^{-1}$
$^1$H-NMR (CDCl$_3$)δ:3.90 (0.5H, m), 3.72 (3H, s), 3.63 (0.5H, m), 3.50 (1H, m), 2.88–1.18(3H, m)

REFERENCE EXAMPLE 45

6,7-dihydroxy-4-thiaoctanoic acid 6,7-dihydroxy-4-thiaoctanoic acid methyl ester as obtained in Reference Example 44 (1.47 g) was dissolved in a mixture of methanol (20 ml) and water (1 ml). To this solution, sodium methylate (1.5 ml) was added under ice cooling conditions, followed by stirring at room temperature for 1 day. To the reaction mixture, 1N hydrochloric acid was added, and the mixture was extracted with ethyl acetate; the solvent was distilled off under reduced pressure to yield the title compound (1.00 g, yield 73%) as a colorless oily substance.
IR (Neat) υ:3400, 2975, 2925, 1720, 1400, 1230, 1130, 1050, 990 cm$^{-1}$
$^1$H-NMR (CDCl$_3$) 3:3.58–3.28 (4H, m), 2.69–2.37 (6H, m), 1.06–0.90 (3H, m)

REFERENCE EXAMPLE 46

6,7-bis( 12-cyclohexyldodecanoyloxy)-4-thiaheptanoic acid t-butyl ester 12-cyclohexyldodecanoyl chloride (301 mg, 1.0 mM) and 6,7-dihydroxy- 4-thiaheptanoic acid t-butyl ester (112 mg, 0.5 mM) as obtained in Reference Example 22 were dissolved in dichloromethane (2 ml). To this solution, dimethylaminopyridine (122 mg, 1.0 mM) and triethylamine (0.1 ml, 0.0725 mM) were added under ice cooling conditions and, followed by stirring under ice cooling conditions for 30 minutes and then at room temperature for 1 hour. To the reaction mixture, dichloromethane (15 ml) and water (20 ml) were added, followed by vigorous stirring, after which the dichloromethane layer was separated and then concentrated to dryness under reduced pressure to yield the title compound (389 mg, yield 71.5%) as a colorless syrup.
IR(neat)υ:2920, 2850, 1735, 1440, 1410, 1390, 1360, 1245, 1150cm$^{-1}$
$^1$H-NMR(CDCl$_3$) 3; 0.872(2H,m), 1.17844(H,m), 1.253(52H,s), 1.660(4H,m), 2.314(4H,t,J=7.8 Hz), 2.523(2H,t,J=8.2 Hz), 2.748(2H,t,J=6.6 Hz), 2.797( 2H,t,J= 6.6 Hz), 4.186(1H,dd,J=6.0 Hz, 12.0 Hz), 4.366(1H,dd,J= 1.4 Hz),12.0 Hz), 5.153(1H,m)

REFERENCE EXAMPLE 47

6,7-bis(12-cyclohexyldodecanoyloxy)-4-thiaheptanoic acid 6,7-bis(12-cyclohexyldodecanoyloxy)-4-thiaheptanoic acid t-butyl ester (346 mg, 0.45 mM) as obtained in Reference Example 46 were dissolved in trifluoroacetic acid (2 ml), followed by stirring at room temperature for 1 hour. The reaction mixture was concentrated to dryness under reduced pressure. The resulting residue was dissolved in dichloromethane (2×2 ml) and then concentrated to dryness under reduced pressure to yield the title compound (333 mg, yield 100%) as a colorless solid.
IR(neat) $\upsilon$; 2920, 2850, 1735, 1705, 1440, 1410, 1360, 1340, 1240, 1155, 1105, 1050 cm$^{-1}$

REFERENCE EXAMPLE 48

12-cyclohexyldodecanoic acid $CrO_3$ (VI) (3.204 g, 32.04 mM) was dissolved in sulfuric acid (2.76 ml), followed by stirring for a time, and then water (4.8 ml) was added to yield a solution. This solution was added drop by drop to a solution of 12-cyclohexyldodecanol (5.36 g, 20 mM) in acetone (300 ml) under ice cooling conditions, followed by stirring for 1 hour. To the mixture, iso-prapanol (about 2 ml) was added and then concentrated to dryness under reduced pressure. To the resulting residue, water (50 ml) and chloroform (50 ml) were added, followed by vigorous stirring, after which the chloroform layer was separated. The chloroform layer was dryed over anhydrous sodium sulfate, purified by silica gel colum (50 g) (methanol-chloroform (1:49)) to yield the title compound (5.3 g, yield 58.7%) as a colorless powder.

REFERENCE EXAMPLE 49

11-cyclohexylundecyl isocyanae 12-cyclohexyldodecanoic acid (1.695 g, 6 mM) as obtained in Reference Example 48 was dissolved in a mixed solution of dichloromethane (6 ml) and thionyl chloride (6 ml), followed by a reflux for 1 hour. The reaction mixture was concentrated to dryness under reduced pressure. The resulting residue was dissolved in tetrahydrofuran (15 ml), and to thus obtained solution was added drop by drop a solution of sodium azide (520 mg, 8 mM) in methanol (20 ml) under ice cooling conditions. Thus obtained solution was stirred under ice cooling conditions for 30 minutes and then at room temperature for 1 hour, concentrated to dryness under reduced pressure. The resulting residue was dissolved in toluene (20 ml). The toluene layer was washed with saturated saline (10×2 ml), dried over anhydrous sodium sulfate, and then concentrated to about the half amount of it, followed by stirring at 100° C. for 30 minutes. The reaction mixture was concentrated to dryness under reduced pressure. The resulting residue was purified by silica gel colum (5 g) (n-hexane) to yield the title compound (724 mg, yield 41.8%) as a colorless oily substance.

REFERENCE EXAMPLE 50

6,7-bis(11-cyclohexylundecylcarbamoyloxy)-4-thiaheptanoic acid t-butyl ester 11-cyclohexylundecyl isocyanate (236 mg, 0.812 mM) as obtained in Reference Example 49 and 6,7-dihydroxy-4-thiaheptanoic acid t-butyl ester (84 mg, 0.375 mM) as obtained in Reference Example 22 were dissolved in dichloromethane (1.5 ml) and then tin-di-n-butyl (247 mg, 0.375 mM) was added, followed by stirring at room temperature for 16 hours. The reaction mixture was purified by silica gel colum (5 g) (n-hexane-chloroform (1:4)) and then silica gel column (5 g) (ethyl acetate-n-hexane (1:4)) to yield the title compound (316 mg, yield 100%) as a colorless syrup.
IR(neat)$\upsilon$; 3330, 2920, 2850, 1730, 1710, 1700, 1530, 1460, 1440, 1360, 1250, 1140 cm$^{-1}$
$^1$H-NMR(CDCl$_3$)$\delta$; 0.863(4H,m), 1.444(4H,m), 1.252(48H, s), 1.451(11H,s), 1.660(8H,m), 2.525(2H,t,J=7.0 Hz), 2.737(2H,d,J=6.2 Hz), 2.804(2H,t,J=8.0 Hz), 3.159(9H,q,J=6.8 Hz), 4.250 (2H,d,J=5.4 Hz), 4.68–4.90(2H,m), 5.020(1H,m)

REFERENCE EXAMPLE 51

6,7-bis(11-cyclohexylundecylcarbamoyloxy)-4-thiaheptanoic acid 6,7-bis(11-cyclohexylundecylcarbamoyloxy)-4-thiaheptanoic acid t-butyl ester as obtained in Reference Example 50 was dissolved in trifluoroacetic acid (1 ml), followed by stirring at room temperature for 1 hour. The reaction mixture was concentrated to dryness under reduced pressure. The resulting residue was dissolved in dichloromethane (1 ml) and then concentrated to dryness under reduced pressure to yield the title compound (291 mg, yield 100%) as a colorless solid. This compound was used in the following reaction without being purified.

REFERENCE EXAMPLE 52

(2R)-3-acetylthio-2-methylpropionic acid methyl ester

To a solution of (S)-( + )-3-hydroxy-2-methylpropionic acid methyl ester (8.00 g) and triphenyl phosphin (26.64 g) in tetrahydrofuran (170 ml) was added azodicarboxylic acid diethyl ester (16 ml) was added, followed by stirring at 0° C. for 30 minutes. After addition of thioacetic acid at 0° C., the reaction mixture was stirred at room temperature for 16 hours, after which saturated aqueous solution of sodium hydrogen carbonate was added and the reaction mixture was extracted with ethyl acetate. The extract was washed with saturated saline, dried over anhydrous sodium sulfate, and the solvent was distilled off. The resulting residue was washed with hexane and the flitrate was concentrated. The resulting residue was distilled (83–87° C./0.2 mmHg) to yield the title compound (4.95 g, yield 41%) as a colorless oily substance.
IR(neat)$\upsilon$; 2980, 2950, 1730, 1690, 1455, 1430, 1350, 1220, 1170, 1130, 950 cm$^{-1}$
$^1$H -NMR(CDCl$_3$)$\delta$; 1.24(3H,d,J=7.0 Hz), 2.33(3H,s), 2.60–2.79(1H,m), 2.97–3.18(2H,m), 3.70(3H,s).

REFERENCE EXAMPLE 53

(2R,6R)-6,7-dihydroxy-2-methyl-4-thiaheptanoic acid methyl ester

To (2R)-3-acetylthio-2-methylpropionic acid methyl ester (528 mg) as obtained in Reference Example 52 was added 7% ammonia-ethanol solution (3 ml), followed by stirring at room temperature for 4 hours, and the reaction mixture was concentrated. The resulting residue was dissolved in dichloromethane (18 ml), after which zinc (1.37 g), an acidic solution (methanol: hydrochloric acid: sulufuric acid=100:

6.5: 1) (9.6 ml), and glycidol (2.22 g) were added, and was refluxed with heating for 24 hours. After cooling and addition of water, the reaction mixture was extracted with dichloromethane. The extract was washed with saturated saline, dried over anhydrous sodium sulfate, and the solvent was distilled off. The resulting residue was purified by silica gel column chromatography (ethyl acetate) to yield the title compound (162 mg, yield 26%) as a colorless oily substance.

IR(neat)cm$^{-1}$; 3400, 2930, 2870, 1730, 1630, 1450, 1430, 1370, 1355, 1210, 1160, 1070, 1030.

$^1$H-NMR(CDCl$_3$)δ; 1.26(3H,d,J=6.8 Hz), 2.53–3.10(5H,m), 3.55–3.99(3H,m), 3.72(3H,s).

REFERENCE EXAMPLE 54

(2R,6R)-6,7-isopropylidene-2-methyl-4-thiaheptanoic acid methyl ester

To a solution (2R,6R)-6,7-dihydroxy-2-methyl-4-thiaheptanoic acid methyl ester (162 mg) as obtained in Reference Example 53 in dichloromethane (1.6 ml), 2,2-dimethoxypropane (0.34 ml) and p-toluenesulfuric acid-monohydrate (5 mg) were added, followed by stirring at room temperature for 24 hours. To the reaction mixture was added saturated aqueous solution of sodium hydrogen carbonate, and the reaction mixture was extracted with ethyl acetate. The extract was washed with saturated saline, dried over anhydrous sodium sulfate, and the solvent was distilled off, to yield the title compound (180 mg, yield 93%) as a colorless oily substance.

IR(neat)cm$^{-1}$; 2980, 2930, 2870, 1730, 1450, 1430, 1370, 1250, 1210, 1160, 055, 860.

$^1$H-NMR(CDCl$_3$) 3; 1.25(3H,d,J=6.8 Hz), 1.36(3H,s), 1.43(3H,s), 2.55– 2.95(5H,m), 3.65–3.76(1H,m), 3.71(3H, s), 4.04–4.32(2H,m).

REFERENCE EXAMPLE 55

(2R,6R)-6,7-isoprolpylidene-2-methyl-4-thiaheptanoic acid

To a solution of (2R,6R)-6,7-isopropylidene-2-methyl-4-thiaheptanoic acid methyl ester (180 mg) as obtained in Reference Example 54 in tetrahydrofuran (2.2 ml), an aqueous solution of 1N sodium hydroxide (2.2 ml) was added, followed by stirring at room temperature for 3.5 hours. After addition of a 5% aqueous solution of citric acid, the reaction mixture was extracted with ethyl acetate. The extract was washed with saturated saline, dried over anhydrous sodium sulfate, and the solvent was distilled off, to yield the title compound (168 mg), yield 99%) as a colorless oily substance.

IR(neat)cm$^{-1}$; 2980, 2930, 1730, 1700, 1450, 1410, 1370, 1220, 1150, 1055, 860.

$^1$H-NMR(CDCl$_3$)δ; 1.29(3H,d,J=6.8 Hz), 1.36(3H,s), 1.43(3H,s), 2.56– 2.98(5H,m), 3.71(1H,dd,J=6.2,8.2 Hz), 4.11(1H,dd,J=6.0,8.2 Hz),4.18– 4.33(1H,m).

REFERENCE EXAMPLE 56

4-((2R,6R)-6,7-isopropylidene-2-methyl-4-thiaheptanoylamino)benzoylglutamic acid di-t-butyl ester To a solution of 4-aminobenzoylglutamic acid di-t-butyl ester (543 mg) in pyridine (4 ml), phosphorous trichloride (0.063 ml) was added, followed by stirring at room temperature for 2 hours. To the reaction mixture was added a solution of (2R,6R)-6,7-isopropylidene-2-methyl-4-thiaheptanoic acid (168 mg) as obtained in Reference Example 55 in pyridine (3 ml), followed by stirring at room temperature for 24 hours. After addition of a 5% aqueous solution of citric acid, the reaction mixture was extracted with ethyl acetate. The extract was washed with a saturated aqueous solution of sodium hydrogen carbonate and saturated saline, dried over anhydrous sodium sulfate, and the solvent was distilled off. The resulting residue was purified by silica gel column chromatography (hexane:acetone=2:1) to yield the title compound (358 mg, yield 84%) as a colorless oily substance.

IR(neat)cm$^{-1}$; 3310, 2970, 2930, 1730, 1640, 1595, 1530, 1500, 1365, 1250, 1150.

$^1$H-NMR(CDCl$_3$)δ; 1.32(3H,d,J=6.8 Hz), 1.35(3H,s), 1.42(12H,s), 1.95– 3.03(9H,m), 3.65–4.72(4H,m), 7.00(1H, d,J = 7.4 Hz), 7.58–7.86(5H,m).

REFERENCE EXAMPLE 57

4-((2R,6R)-6,7-dihydroxy-2-methyl4-thiaheptanoylamino)benzoylglutamic acid di-t-butyl ester To a solution of 4-((2R,6R)-6,7-isopropylidene-2-methyl-4-thiaheptanoylamino)benzoylglutamic acid di-t-butyl ester (100 mg) as obtained in Reference Example 56 in tetrahydrofuran (2 ml), a 50% aqueous solution of formic acid (2 ml) was added, followed by stirring at room temperature for 5 hours. After addition of water, the reaction mixture was extracted with ethyl acetate. The extract was washed with a saturated aqueous solution of sodium hydregen carbonate and saturated saline, dried over anhydrous sodium sulfate, and the solvent was distilled off. The resulting residue was purified by silica gel column chromatography (ethyl acetate to hexane) to yield the title compound (58 mg, yield 62%) as a colorless oily substance.

IR(neat)cm$^{-1}$; 3430, 2970, 2920, 1730, 1630, 1520, 1500, 1360, 1250,1150.

$^1$H-NMR(CDCl$_3$)δ; 1.27(3H,d,J=6.6 Hz), 1.42(9H,s), 1.49(9H,s), 1.90– 3.00(9H,m), 3.54–3.92(3H,m), 4.56–4.70(1H,m), 7.26(1H,d,J=7.4 Hz), 7.60(2H,d,J=8.8 Hz), 7.73(2H,d,J=8.8 Hz), 8.69(1H,bs).

REFERENCE EXAMPLE 58

4-[6(R),7-dihydroxy-4-thiaheptanoylamino]benzoylglutamic acid di-t-butyl ester

To a solution of 2,2'-dithiobis[(4-((1,3-bis(t-butoxycarbonyl)propyl)carbamoyl)phenyl)carbamoylethane] (100 mg) as obtained in Reference Example 5 and zinc powder (1.15 mg) in dichloromethane (20 ml), an acidic solution (methanol: hydrochloric acid: sulufuric acid=100: 6.5: 1) (8 ml) was added, followed by stirring at room temperature for 15 minutes. After addition of (R)-glycidol (1.88 g), the reaction mixture was stirred at 40° C. for 5 hours. The reaction mixture was diluted with dichlorornethane, washed with a 5% aqueous solution of KHSO4 and saturated saline, and dried over anhydrous sodium sulfate. The solvent was concentrated and the resulting residue was purified by silica gel column chromatography (chloroform: methanol=30:1→ 10:1) to yield the title compound (1.75 g, yield 64%) as a colorless syrup. ps IR(neat)υ; 3300, 1725, 1635, 1590, 1530, 1500, 1360, 1250, 1150 cm$^{-1}$.

$^1$H-NMR(CDCl$_3$)δ; 1.42(9H,s), 1.48(9H,s), 1.90–2.50(4H, m), 2.50–2.75(4 H,m), 2.87(2H,t,J=6.2 Hz), 3.30–3.95(5H, m), 4.62(1H,m), 7.30(1H,d,J= 7.4 Hz), 7.60(2H,d,J=8.8 Hz), 7.73(2H,d,J=8.8 Hz), 8.91(1H,s).

REFERENCE EXAMPLE 59

(R)-S-benzylthioglycerol

To a solution of(R)-glycidol (1.48 g) and benzylmercaptane (2.48 g) in methanol (6 ml), 28% sodium methylate (3 drops) was added, followed by stirring at room temperature for 30 minutes. The solvent was concentrated to yield the title compound (4.08 g, yield 100%) as a colorless syrup.
IR(neat)υ; 3350, 2910, 1485, 1450, 1415, 1065, 1020, 695 cm$^{-1}$.
$^1$H -NMR(CDCl$_3$)δ; 2.36(2H,s), 2.51(1H,dd,J=13.8,7.6 Hz), 2.60(1H,dd,J=13.8,5.0 Hz), 3.50(1H,dd,J=11.0,5.8 Hz), 3.60–3.85(2H,m), 3.74(2H,s), 7.20–7.45(5H,m).

REFERENCE EXAMPLE 60

6(R), 7-dihydroxy-4-thia-2(E)-heptenoic acid-t-butyl ester and 6(R), 7-dihydroxy-4-thia-2(Z)-heptenoic acid-t-butyl ester To a solution of (R)-S-benzylthioglycerol (4.08 g) as obtained in REFERENCE EXAMPLE 59 in tetrahydrofuran (40 ml)-liquid ammonia (10 ml), sodium (760 mg) was added at −78° C. until a sustained dark blue color was observed. After the ammonia was distilled off, the reaction mixture was made acidic by addition of methanol-hydrochloric acid and was concentrated. The resulting residue was dissolved in methanol (5 ml), after which propiolic acid-t-butyl ester (2.50 g) and triethylamine (1 ml) were added, followed by stirring at room temperature for 5 hours. After removal of precipitated insoluble substances, the solvent was concentrated. The resulting residue was purified by silica gel column chromatography (n-hexane: ethyl acetate= 1) to yield the title compounds (E-configuration, 1.02 g, yield 21%) Z-configuration, 3.01 g, yield 62%) as colorless oily substances. E-configuration
IR(neat) υ; 3400, 2970, 2925, 1700, 1680, 1575, 1365, 1310, 1250, 1140 cm$^{-1}$.
$^1$H-NMR(CDCl$_3$)δ;1.48(9H,s), 2.39(1H,brs), 2.80–3.10(3H, m), 3.55– 3.85(2H,m), 3.93(1H,m), 5.76(1H,d,J=15.2 Hz), 7.54(1H,d,J=15.2 Hz). Z-configuration
IR(neat)υ; 3400, 2970, 2925, 1700, 1680, 1575, 1365, 1310, 1250, 1140 cm$^{-1}$.
$^1$H-NMR(CDCl$_3$)δ; 1.50(9H,s), 2.58(1H,brs), 2.80–3.10(3H,m), 3.55– 3.85(2H,m), 3.92(1H,m), 5.81(1H, d,J=10.2 Hz), 7.02(1H,d,J=10.2 Hz).

REFERENCE EXAMPLE 61

6(R), 7-bis(palmitoyloxy)-4-thia-2(E)-heptenoic acid-t-butyl ester

To a solution of 6(R), 7-dihydroxy-4-thia-2(E)-heptenoic acid-t-butyl ester ( 1.0 g) as obtained in REFERENCE EXAMPLE 60 and dimethylaminopyridine (1.30 g) in dichloromethane (15 ml), palmitoyl chloride (2.47 g) was added, followed by stirring at room temperature for 2 hours. After the solvent was concentrated, the resulting residue was purified by silica gel column chromatography (n-hexane: ethyl acetate=20:1) to yield the title compound (2.814 g, yield 93%) as colorless solid.
IR(neat)υ; 2920, 2850, 1740, 1690, 1570, 1460, 1360, 1230, 1150 cm$^{-1}$.
$^1$H-NMR(CDCl$_3$) δ; 0.88(6H,t,J=6.8 Hz), 1.25(48H,s), 1.48(9H,s), 1.50– 1.70(4H,m), 2.32(2H,t,J=7.6 Hz), 2.33(2H,t,J=7.6 Hz), 3.03(2H,d,J=6.4 Hz), 4.17( 1H,dd,J= 12.0,5.4 Hz), 4.32(1H,dd,J=12.0,4.0 Hz), 5.21(1H,m), 5.78(1H,d,J=15.2 Hz), 7.49(1H,d,J=15.2 Hz).

REFERENCE EXAMPLE 62

6(R), 7-bis(palmitoyloxy)-4-thia-2(E)-hepteonoic acid

To a solution of 6(R), 7-bis(palmitoyloxy)-4-thia-2(E)-heptenoic acid-t-butyl ester (2.81 g) as obtained in Reference Example 61 in dichloromethane (2 ml), trifluoroacetic acid (6 ml) was added, followed by stirring at room temperature for 1 hour. The solvent was distilled off under reduced pressure to yield the title compound (2.688 g, yield 99%) as a colorless powder.
IR(neat)υ; 2917, 2850, 1735, 1664, 1579, 1469, 1405, 1267, 1195, 1172, 1110 cm$^{-1}$.
$^1$H-NMR(CDCl$_3$–CD$_3$OD)δ; 0.88(6H,t,J=6.8 Hz), 1.25(48H,s), 1.50– 1.70(4H,m), 3.06(2H,d,J=6.2 Hz), 4.18(1H,dd,J=12.0,5.4 Hz), 4.34( 1H,dd,J=12.0,4.2 Hz), 5.22(1H,m), 5.87( 1H,d,J=15.2 Hz), 7.66(1H,d,J=15 .2 Hz).

EXAMPLE 1

(6,7,bis(palmitoyloxy)-4-thiaheptanoyl)glycine t-butyl ester

To a solution of 6,7-bis(palmitoyloxy)-4-thiaheptanoic acid as obtained in Reference Example 4 (200 mg) and glycine t-butyl ester hydrochloride (60 mg) in dimethylformamide (3 ml), triethylamine (0.099 ml) and diethyl cyanophosphate (72 ml) were added, followed by stirring at room temperature for 17 hours. After addition of water, the reaction mixture was extracted with chloroform. The extract was washed with a 5% aqueous solution of citric acid, a saturated aqueous solution of sodium. hydrogen carbonate and saturated saline, and dried over anhydrous sodium sulfate, and the solvent was distilled off. The resulting residue was purified by silica gel column chromatography (hexane:ethyl acetate=1:3) to yield the title compound (206 mg, yield 90%) as a wax-like substance.
IRυ$_{max}^{KBr}$ cm$^{-1}$: 3350, 1740, 1660
$^1$H-NMR (CDCl$_3$)δ:0.88 (6H, t, J=6.6 Hz), 1.12–1.42 (48H, m), 1.89 (9H, s), 1.53–1.72 (4H, m), 2.31 (2H, t, J=7.2 Hz), 2.32 (2H, t, J=7.6 Hz), 2.54 ( 2H, t, J=6.8 Hz), 2.73 (2H, d, J=6.6 Hz), 2.89 (2H, t, J=6.8 Hz), 3.95 (2H, d, J=5.0 Hz), 4.17 (1H, dd, J=6.0, 12.0 Hz), 4.38 (1H, dd, J=3.2, 12.0 Hz), 5.09–5.22 (1H, m), 6.10 (1H, m)

EXAMPLE 2

(6,7-7bis(palmitoyloxy)-4-thiaheptanoyl)glycine

To (6,7-bis(palmitoyloxy)-4-thiaheptanoyl)glycine t-butyl ester as obtained in Example 1 (206 mg), trifluoroacetic acid (2 ml) was added, followed by stirring at room temperature for 1 hour. The mixture was concentrated to yield the title compound (188 mg, yield 98%) as a colorless crystal.
IRυ$_{max}^{KBr}$ cm$^{-1}$: 3320, 1730, 1640
$^1$H-NMR (CDCl$_3$)δ:0.88 (6H, t, J=6.8 Hz), 1.03–1.50 (48H, m), 1.50–1.72 ( 4H, m), 2.32 (2H, t, J=7.8 Hz), 2.33 (2H, t, J=7.6 Hz), 2.59 (2H, t, J=7.6 Hz), 2.73 (2H, d, J=6.6 Hz), 2.89 (2H, t, J=7.6 Hz), 4.10 (2H, d, J=5.2 Hz), 4.16 (1H, dd, J=6.2, 11.8 Hz), 4.40 (1H, dd, J=3.2, 11.8 Hz), 5.09–5.23

(1H, m), 6.53 (1H, t, J=5.2 Hz)

EXAMPLE 3

(6,7-bis(palmitoyloxy)-4-thiaheptanoyl)glycylglycine t-butyl ester

To a solution of 6,7-bis(palmitoyloxy)-4-thiaheptanoic acid as obtained in Reference Example 4 (200 mg) and glycylglycine t-butyl ester hydrochloride (80 mg) in dimethyl formamide (3 ml), triethylamine (0.099 ml) and diethyl cyanophosphate (73 mg) were added, followed by stirring at room temperature for 17 hours. After addition of water, the reaction mixture was extracted with chloroform. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (hexane:ethyl acetate=1:3) to yield the title compound (191 mg, yield 78%) as a wax-like substance.
IR$\upsilon_{max}^{KBr}$ cm$^{-1}$: 3370, 3310, 1735, 1675, 1630
$^1$H-NMR (CDCl$_3$)δ: 0.88 (6H, t, J=6.8 Hz), 1.03–1.42 (48H, m), 1.47 (9H, s),
1.52–1.70 (4H, m), 2.31 (2H, t, J=7.6 Hz), 2.32 (2H, t, J=7.6 Hz), 2.56 (2H, t, 2 (J=7.2 Hz), 2.73 (2H, d, J=6.6 Hz), 2.91 (2H, t, J=7.2 Hz), 3.95 (2H, d, J=7.2 Hz), 4.00 (2H, d, J=5.2 Hz), 4.15 (1H, dd, J=6.4, 12.0 Hz), 4.41 (1H, dd, J=3.2, 12.0 Hz), 5.08–5.23 (1H, m), 6.47–6.62 (2H, m)

EXAMPLE 4

(6,7-bis(palmitoyloxy),4-thiaheptanoyl)glycylglycine

To (6,7-bis(palmitoyloxy)-4-thiaheptanoyl)glycylglycine t-butyl ester as obtained in Example 3 (190 mg), trifluoroacetic acid (2 ml) was added, followed by stirring at room temperature for I hour. The mixture was concentrated to yield the title compound (178 mg, yield 100%) as a colorless crystal.
IR$\upsilon_{max}^{KBr}$ cm$^{-1}$: 3300, 1735, 1640
$^1$H-NMR (CDCl$_3$+CD$_3$OD)δ:0.88 (6H, t, J=6.6 Hz), 1.03–1.50 (48H, m), 1.52–1.72 (4H, m), 2.32 (2H, t, J=7.0 Hz), 2.33 (2H, t, J=7.4 Hz), 2.56 (2 H, t, J=7.6 Hz), 2.75 (2H, d, J=6.6 Hz), 2.89 (2H, t, J=7.0 Hz), 3.91–4.03 (4H, m), 4.17 (1H, dd, J=6.2, 11.8 Hz), 4.39 (1H, dd, J=3.2, 11.8 Hz), 5.08–5.22 (1H, m), 7.42–7.62 (1H, m)

EXAMPLE 5

(6,7-bis(palmitoyloxy)-4-thiaheptanoyl) glycylglycylglycine t-butyl ester

To a solution of 6,7-bis(palmitoyloxy)-4-thiaheptanoic acid as obtained in Reference Example 4 (400 mg) and glycylglycylglycine t-butyl ester hydrochloride (149 mg) in dimethylformamide (6 ml), triethylamine (0.094 ml) and diethyl cyanophosphate (150 mg) were added at 0° C., followed by stirring at room temperature for 1 hour. After addition of water, the reaction mixture was extracted with chloroform. The extract was washed with a 5% aqueous solution of citric acid, a saturated aqueous solution of sodium hydrogen carbonate and saturated saline, and dried over anhydrous sodium sulfate, and the solvent was distilled off. The resulting residue was recrystallized (acetone-hexane) to yield the title compound (110 mg, yield 20%) as a wax-like substance.
IR$\upsilon_{max}^{KBr}$ cm$^{-1}$: 3310, 1740, 1635
$^1$H-NMR (CDCl$_3$) 8:0.88 (6H, t, J=7.0 Hz), 1.10–1.40 (48H, m), 1.47 (9H, s), 1.51–1.67 (4H, m), 2.31 (2H, t, J=7.8 Hz), 2.32 (2H, t, J=7.2 Hz), 2.58 ( 2H, t, J=7.2 Hz), 2.73 (2H, d, J=6.6 Hz), 2.83–3.00 (2H, m), 3.93 (2H, d, J= 5.4 Hz 3.96–4.05 (4H, m), 4.13 (1H, dd, J=6.4, 12.0 Hz), 4.42 (1H, dd, J=3.2, 12.0 Hz), 5.08–5.22 (1H, m), 6.71 (1H, t, J=5.4 Hz), 6.79 (1H, t, J= 5.4 Hz), 7.05 t, J=5.4 Hz)

EXAMPLE 6

(6,7-bis(palmi toyloxy)-4-thiaheptanoyl)glycylglycylglycine (6,7-bis(palmitoyloxy)-4-thiaheptanoyl)glycylglycylglycine t-butyl ester as obtained in Example 5 (110 mg) was mixed with trifluoroacetic acid (5 ml), followed by stirring at room temperature for 1 hour. The mixture was concentrated to yield the title compound (81 mg, yield 86%) as a colorless crystal.
IR$\upsilon_{max}^{KBr}$ cm$^{-1}$: 3290, 1740, 1640
$^1$H-NMR (CDCl$_3$+ 5% CD$_3$OD)δ:0.88 (6H, t, J=6.8 Hz), 1.13–1.43 (48H, m), 1.50–1.72 (4H, m), 2.32 (2H, t, J=7.7 Hz), 2.33 (2H, t, J=7.5 Hz), 2.56 (2 H, t, J=7.4 Hz), 2.75 (2H, d, J=7.4 Hz), 3.86–4.03 (6H, m),4.16 (1H, dd, J=6.4, 12.0 Hz), 4.39 (1H, dd, J=3.0, 12.0 Hz), 5.07–5.22 (1H, m)

EXAMPLE 7

(6,7,bis(palmitoyloxy)-4-thiaheptanoyl) glycylglycylglycylglutamic acid di-t-butyl ester To a solution of 6,7-bis(palmitoyloxy)-4-thiaheptanoic acid as obtained in Reference Example 4 (197 mg) and glycylglycylglycylglutamic acid di-tbutyl ester hydrochloride (168 mg) in dimethylformamide (6 ml), triethylamine. (0.105 ml) and diethyl cyanophosphate (73 mg) were added, followed by stirring at room temperature for 24 hours. After addition of water, the reaction mixture was extracted with chloroform. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (chloroform:methanol = 19:1) to yield the title compound (291 mg, yield 91%) as a wax-like substance.
IR$\upsilon_{max}^{KBr}$ cm$^{-1}$: 3330, 1740, 1700, 1630
$^1$H-NMR (CDCl$_3$)δ:0.88 (6H, t, J=6.6 Hz), 1.11–1.40 (48H, m), 1.44 (9H, s), 1.47 (9H, s), 1.51–1.70 (4H, m), 1.82–2.23 (2H, m), 2.31 (4H, t, J=7.8 Hz) 2.59 (2H, t, J=7.0 Hz), 2.73 (2H, d, J=6.6 Hz), 2.91 (2H, t, J=7.0 Hz), 3.88–4.35 (7H, m), 4.35–4.54 (2H, m), 5.07–5.25 (1H, m), 7.00–7.45 (4H, m)

EXAMPLE 8

(6,7:bis(palmitoyloxy)-4-thiaheptanoyl) glycylglycylglycylglutamic acid

To (6,7-bis(palmitoyloxy)-4-thiaheptanoyl)glycylglycylglycylglutamic acid di-t-butyl ester as obtained in Example 7 (291 mg), trifluoroacetic acid (3 ml) was added, followed by stirring at room temperature for 1. hour. The mixture was concentrated to yield the title compound (252 mg, yield 97%) as a colorless crystal.
IR$\upsilon_{max}^{KBr}$ cm$^{-1}$: 3270, 1735, 1660
$^1$H-NMR (CDCl$_3$+5% CD$_3$OD) 3:0.88 (6H, t, J=6.8 Hz), 1.04–1.49 (48H, m), 1.50–1.80 (4H, m), 1.95–2.26 (2H, m), 2.32 (2H, t, J=7.4 Hz), 2.33 (2H, Hz), 2.43 (2H, t, J=6.6 Hz), 2.57 (2H, t, J=7.2 Hz), 2.74 (2H, d, J=6.6 Hz), 2.87 (2H, t, J=7.2 Hz), 3.75–4.11 (6H, m), 4.16 (1H, dd, J=6.4, 12.2 Hz), 4.39 (1H, dd, J=3.2, 12.2 Hz), 4.44–4.56 (1H, m), 5.08–5.23 (1H, m)

EXAMPLE 9

(8-(6,7-bis(palmitoyloxy)-4-thiaheptanoyl) aminooctanoyl)glutamic acid di-t-butyl ester To a solution of 6,7-bis(palmitoyloxy)-4-thiaheptanoic acid as obtained in Reference Example 4 (150 mg) and 8-aminooctanoylglutamic acid di-tbutyl ester (107 mg) in dimethylformamide (4 ml), triethylamine (0.038 ml) and diethyl cyanophosphate (54 mg) were added, followed by stirring at room temperature for 24 hours. After addition of water, the reaction mixture was extracted with chloroform. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (hexane:ethyl acetate=2:3) to yield the title compound (187 mg, yield 81%) as a wax-like substance.

IR$\upsilon_{max}^{KBr}$ cm$^{-1}$: 1730, 1645

$^1$H-NMR (CDCl$_3$)δ:0.88 (6H, t, J=6.8 Hz), 1.09–1.40 (56H, m), 1.45 (9H, s), 1.47 (9H, s), 1.50–2.38 (12H, m), 2.32 (2H, t, J = 8.0 Hz), 2.33 (2H, t, J=2.46 (2H, t, J=7.4 Hz), 2.72 (2H, d, J=6.6 Hz), 2.88 (2H, t, J=7.0 Hz), 3.24 (2H, dr, J=5.6, 5.6 Hz), 4.15 (1H, dd, J=6.4, 12.0 Hz), 4.40 (1H, dd, J=3.4, 12.0 Hz), 4.40–4.55 (1H, m), 5.08–5.24 (1H, m), 5.82 (1H, t, J=5.6 Hz), 6.15 (1H, d, J=8.0 Hz)

EXAMPLE 10

8,(6,7-bis(palmitoyloxy)-4-thiaheptanoyl) aminooctanoylglutami acid

To (8-(6,7-bis(palmitoyloxy)-4-thiaheptanoyl)aminooctanoyl)glutamic acid di-t-butyl ester as obtained in Example 9 (187 mg), trifluoroacetic acid (2 ml) was added, followed by stirring at room temperature for 1 .hour. The mixture was concentrated to yield the title compound (167 mg, yield 100%) as a colorless crystal.

IR$\upsilon_{max}^{Ksr}$ cm$^{-1}$: 3360, 1735, 1630

$^1$H-NMR (CDCl$_3$+ 5% CD$_3$OD)δ: 0.88 (6H, t, J=7.0 Hz), 1.03–1.41 (48H, m), 1.41–1.73 (6H, m), 1.95–2.38 (4H, m), 2.32 (2H, t, J = 7.6 Hz), 2.33 (2H, t,J=7.4 Hz), 2.54 (2H, t, J=7.2 Hz), 2.71 (2H, d, J=6.6 Hz), 2.87 (2H, t, J=7.2 Hz), 3.17–3.35 (1H, m), 4.14 (1H, dd, J=6.6, 12.0 Hz), 4.42 (1H, dd, J=2.8, 12.0 Hz), 4.52–4.70 (1H, m), 5.06–5.22 (1H, m), 6.25–7.23 (2H, m)

EXAMPLE 11

N (alpha)-(t-butyloxycarbonyl)-N(delta)-(6,7-bis(palmitoyloxy)-4-thiaheptanoyl) ornitylglycylglycylglutamic acid di-t-butyl ester To a solution of 6,7-bis(palmitoyloxy)-4-thiaheptanoic acid as obtained in Reference Example 4 (100 mg) and (N(alpha)-(tbutyloxycarbonyl)ornitylglycylglycylglutamic acid di-t-butyl ester (90 mg) in dimethylformamide (3 ml), triethylamine (0.051 ml) and diethyl cyanophosphate (36 mg) were added, followed by stirring at room temperature for 24 hours. After addition of water, the reaction mixture was extracted with chloroform. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (chloroform:methanol=19:1) to yield the title compound (134 mg, yield 85%) as a wax-like substance.

IR$\upsilon_{max}^{KBr}$ cm$^{-1}$: 3300, 1735, 1650

$^1$H-NMR (CDCl$_3$) 3:0.88 (6H, t, J=6.8 Hz), 1.05–1.40 (50H, m), 1.43 (9H, s), 1.44 (9H s), 1.46 (9H, s), 1.50–2.24 (10H, m), 2.24–2.38 (6H, m), 2.48 (2.48 (2H, t, J=6.8 Hz), 2.72 (2H, d, J=6.4 Hz), 2.80–2.93 (2H, m), 3.10–3.55 (1H, m), 3.96 (4H, d, J=5.4 Hz), 4.01–4.50 (4H, m), 5.08–5.22 (1H, m) 5.45–5.59 (1 H, m), 6.38–6.53 (1H, m), 6.97 (1H, d, J=7.6 Hz), 7.10–7.22 (1H, m), 7.30–7.40 (1H, m)

EXAMPLE 12

N (delta)-(6,7-bis(palmitoyloxy)-4-thiaheptanoyl) ornitylglycylglutamic acid hydrochloride To N(alpha)-(t-butyloxycarbonyl)-N(delta)-(6,7-bis(palmitoyloxy)-4-thiaheptanoyl)ornitylglycylglycylglutamic acid di-t-butyl ester as obtained in Example 11 (134 mg), a 4N solution of hydrochloric acid (4 ml) in acetic acid was added, followed by stirring at room temperature for 4 hours. The solvent was distilled off to yield the title compound (115 mg, yield 100%) as a colorless crystal.

Ir$\upsilon_{max}^{KBr}$ cm$^{-1}$ : 3300, 1735, 1650

$^1$H-NMR (CDCl$_3$+CD$_3$OD) 3:0.81 (6H, t, J=6.8 Hz), 0.97–1.42 (50H, m), 1.42–1.68 (4H, m), 1.68–3.28 (19H, m), 3.67–4.50 (7H, m), 5.00–5.18 (1H,m)

EXAMPLE 13

N (alpha)-(6,7-bis(palmitoyloxy)-4-thiaheptanoyl) -N(delta)-(t-butyloxycarbonyl) ornitylglycylglycylglutamic acid di-t-butyl ester To a solution of 6,7-bis(palmitoyloxy)-4-thiaheptanoic acid as obtained in Reference Example 4 (100 mg) and (N(delta)-(t-butyloxycarbonyl)ornitylglycylglycylglutamic acid di-t-butyl ester (107 mg) in dimethylformamide (3 ml), triethylamine (0.025 ml) and diethyl cyanophosphate (37 mg) were added, followed by stirring at room temperature for 24 hours. After addition of water, the reaction mixture was extracted with chloroform. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (chloroform:methanol=19:1) to yield the title compound (180 mg, yield 96%) as a wax-like substance.

IR$\upsilon_{max}^{KBr}$ cm$^{-1}$: 3290, 1725, 1630

$^1$H-NMR (CDCl$_3$)δ:0.88 (6H, t, J=6.6 Hz), 1.05–1.42 (50H, m), 1.43 (9H, s), 1.44 (9H, s), 1.46 (9H, s), 1.50–2.20 (8H, m), 2.31 (4H, t, J=7.6 Hz), 2.50–3.40 (8H, m), 3.75–4.60 (8H, m), 4.78–4.92 (1H, m), 5.08–5.21 (1H, m), 6.90–7.52 (4H, m)

EXAMPLE 14

N(alpha)-(6,7-bis(palmitoyloxy)-4-thiaheptanoyl)ornitylglycylglycylglutamic acid hydrochloride To N(alpha)-(6,7-bis(palmitoyloxy)-4-thiaheptanoyl)-N(delta)-(t-butyloxycarbonyl)ornitylglycylglycylglutamic acid di-t-butyl ester as obtained in Example 13 (180 mg), a 4N solution of hydrochloric acid (4 ml) in acetic acid was added, followed by stirring at room temperature for 17 hours. The solvent was distilled off to yield the title compound (150 mg, yield 100%) as a colorless crystal.
IR$v_{max}^{KBr}$ cm$^{-1}$: 3420, 1740, 1650
$^1$H-NMR (CDCl$_3$+5% CD$_3$OD) δ: 0.88 (6H, t, J = 7.0 Hz), 1.03–1.50 (50H, m), 1.50–1.72 (4H, m), 1.72–3.12 (18H, m), 3.64–4.60 (8H, m), 5.09–5.23 (1H, m)

EXAMPLE 15

N(alpha)-(6,7-bis(palmitoylxy)-4-thiahentanoyl),N(epsiron)-(t-butyloxycarbonyl)lysylglycylglycylglutamic aciddi-t-butyl ester To a solution of 6,7-bis(palmitoyloxy)-4-thiaheptanoic acid as obtained in Reference Example 4 (100 mg) and N(epsiron)-(tbutyloxycarbonyl)lysylglycylglycylglutamic acid di-t-butyl ester (110 mg) in dimethylformamide (3 ml), triethylamine (0.025 ml) and diethyl cyanophosphate (37 mg) were added, followed by stirring at room temperature for 24 hours. After addition of water, the reaction mixture was extracted with chloroform. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (chloroform:methanol=19:1) to yield the title compound (190 mg, yield 100%) as a wax-like substance.
IR$v_{max}^{KBr}$ cm$^{-1}$: 3300, 1730, 1690, 1630
$^1$H-NMR (CDCl$_3$)δ:0.88 (6H, t, J=6.6 Hz), 1.05–1.50 (50H, m), 1.43 (9H, s), t, 1.44 (9H, s), 1.46 (9H, s), 1.50–1.72 (4H, m), 1.72–2.38 (4H, m), 2.31 (4 H, t, 3.00–3.37 (2H, m), 3.72–4.59 (5H, m), 4.80–4.93 (1H, m), 5.08–5.22 (1H, m), 6.89–7.52(4H, m)

EXAMPLE 16

N(alpha)-(6,7-bis(palmitoyloxy)-4-thiaheptanoyl)lysylglycylglycylglutamic acid hydrochloride To N(alpha)-(6,7-bis(palmitoyloxy)-4-thiaheptanoyl)-N(epsiron)-(tbutyloxycarbonyl)lysylglycylglycylglutamic acid di-t-butyl ester as obtained in Example 15 (190 mg), a 4 N hydrochloric acid (4 ml) in acetic acid was added, followed by stirring at room temperature for 17 hours. The solvent was distilled off to yield the title compound (158 mg, yield 100%) as a colorless crystal.
IR$v_{max}^{KBr}$ cm$^{-1}$: 3300, 1740, 1650
$^1$H-NMR (CDCl$_3$+CD$_3$OD) 3:0.88 (6H, t, J=6.8 Hz), 1.04–1.90 (56H, m), 1.90–1.36 (8H, m), 2.32 (2H, t, J=7.8 Hz), 2.33 (2H, t, J=7.6 Hz), 2.60 (2H, t, J=6.6 Hz), 2.76 (2H, d, J=6.4 Hz), 2.86 (2H, t, J=6.6 Hz), 3.80–4.55 (8H, m), 5.09–5.23 (1H, m)

EXAMPLE 17

(4-(6,7,bis(palmitoyloxy)-4-thiaheptanoylmino)benzoyl)glutamic acid di-t-butyl ester To a solution of 4-aminobenzoylglutamic acid di-t-butyl ester (115 mg) in pyridine (2.3 ml), phosphorus trichloride (0.013 ml) was added, followed by stirring at room temperature for 2 hours. To the mixture, 6,7-bis(palmitoyloxy)-4-thiaheptanoic acid (100 mg) was added, followed by stirring at room temperature for 24 hours. The reaction mixture was diluted with water, extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (hexane:ethyl acetate=3:2) to yield the title compound (120 mg, yield 77%) as a wax-like substance.
IR$v_{max}^{KBr}$ cm$^{-1}$: 3350, 1730
$^1$H-NMR (CDCl$_3$)δ:0.88 (6H, t, J=6.6 Hz), 1.03–1.37 (48H, m), 1.42 (9H, s), 1.49 (9H, s), 1.53–1.80 (4H, m), 1.90–3.12 (14H, m), 4.15 (1H, dd, J=6.8, Hz), 4.46 (1H, dd, J=3.0, 12.0 Hz), 4.58–4.72 (1H, m), 5.08–5.23 (1H, m), 7.00 (1H, d, J=7.4 Hz), 7.60 (2H, d, J=8.8 Hz), 7.80 (2H, d, J =8.8 Hz), 8.15 (1H, bs)

EXAMPLE 18

(4,(6,7-bis(palmitoyloxy)-4,thiaheptanoylamino)benzoyl)glutamic acid

A solution of (4-(6,7-bis(palmitoyloxy)-4-thiaheptanoylamino)benzoyl)glutamic acid di-t-butyl ester as obtained in Example 17 (120 mg) in trifluoroacetic acid (5 ml) was stirred at room temperature for 4 hours and then concentrated to yield the title compound (105 mg, yield. 98%) as a colorless crystal.
IR$v_{max}^{KBr}$ cm$^{-1}$: 3450, 1735, 1640
$^1$H-NMR (CDCl$_3$+CD$_3$OD) 3:0.88 (6H, t, J=6.9 Hz), 1.13–1.42 (48H, m), 1.51–1.72 (4H, m), 2.32 (2H, t, J=7.7 Hz), 2.34 (2H, t, J=7.5 Hz), 2.68 (2H, t, J=7.4 Hz), 2.75 (2H, d, J=6.8 Hz), 2.94 (2H, t, J=7.4 Hz), 4.17 (1H, dd, J=6.6, 12.0 Hz), 4.42 (1H, dd, J=3.2, 12.0 Hz), 4.63–4.78 (1H, m), 5.10–5.25 (1H, m), 7.64 (2H, d, J=8.7 Hz), 7.79 (2H, d, J = 8.7 Hz)

EXAMPLE 19

[4-(6,7,bis(palmitoyloxy)-4-thiaheptanoyl-amino )benzenesulfonyl)glutamic acid di-t-butyl ester To a solution of 4-aminobenzenesulfonylglutamic acid di-t-butyl ester (189 mg) in pyridine (2.3 ml), phosphorus trichloride (0.023 ml) was added, followed by stirring at room temperature for 2 hours. To the mixture, 6,7-bis(palmitoyloxy)- 4-thiaheptanoic acid as obtained in Reference Example 4 (150 mg) was added, followed by stirring at room temperature for 24 hours. After addition of water, the reaction mixture was extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (hexane:ethyl acetate=2:1) to yield the title compound (213 mg, yield 89%) as a wax-like substance.
IR$v_{max}^{KBr}$ cm$^{-1}$: 3370, 3270, 1730, 1700
$^1$H-NMR (CDCl$_3$)δ:0.88 (6H, t, J=7.0 Hz), 1.12–1.41 (48H, m), 1.45 (9H, s), 1.63 (9H, s), 1.51–3.18 (14H, m), 3.80 (1H, dt, J=4.7, 9.2 Hz), 4.13 (1H, dd, J=7.0, 12.1 Hz), 4.50 (1H, dd, J=3.1, 12.1 Hz), 5.09–5.23 (iH, m), 5.19 (1H, d, J =9.2 Hz), 7.66–7.81 (4H, m), 8.25 (1H, bs)

EXAMPLE 20

(4-(6,7-bis(palmitoyloxy)-4-thiaheptanoyl-amino)benzenesulfonyl)-glutamic acid

A solution of (4-(6,7-bis(palmitoyloxy)-4-thiaheptanoylamino)benzenesulfonyl)glutamic acid di-t-butyl ester as obtained in Example 19 (213 mg) in trifluoroacetic acid (5 ml) was stirred at room temperature for 4 hours and then concentrated to yield the title compound (190 mg, yield 100%) as a colorless crystal.

IR$\nu_{max}^{KBr}$ cm$^{-1}$: 3340, 3260, 1730, 1650

$^1$H-NMR (CDCl$_3$)δ:0.88 (6H, t, J=6.8 Hz), 1.03–1.49 (48H, m), 1.49–1.72 (4H, m), 1.72–3.10 (14H, m), 3.88–4.55 (3H, m), 5.12–5.30 (1H, m), 5.96–6.10 (1H, m), 7.65–7.90 (4H, m), 8.78 (1H, bs)

EXAMPLE 21

[4-(6,7-bis(palmitoyloxy)-4-thiaheptanoylamino) benzoyl)aspartic acid di-t-butyl ester To a solution of 4-aminobenzoylaspartic acid di-t-butyl ester (168 mg) in pyridine (2.3 ml), phosphorus trichloride (0.02 ml) was added, followed by stirring at room temperature for 2 hours. To the mixture, 6,7-bis(palmitoyloxy)-4-thiaheptanoic acid as obtained in Reference Example 4 (150 mg) was added, followed by stirring at room temperature for 64 hours. After addition of water, the reaction mixture was extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (hexane:ethyl acetate = 3:1) to yield the title compound (197 mg, yield 85%) as a wax-like substance.

IR$\nu_{max}^{KBr}$ cm$^{-1}$: 3330, 1735, 1640 $^1$H-NMR (CDCl$_3$)δ: 0.88 (6H, t, J=6.7 Hz), 1.13–1.39 (48H, m), 1.44 (9H, s), 1.48 (9H, s), 1.52–1.72 (4H, m), 2.27–2.39 (4H, m), 2.62–3.10 (8H, m), 4.15 dd, J=6.7, 12.0 Hz), 4.47 (1H, dd, J=3.3, 12.0 Hz), 4.81–4.93 (1H, m), 5.08–5.25 (1H, m), 7.17 (1H, d, J=7.7 Hz), 7.65 (2H, d, J=8.8 Hz), 7.79 (2H, d, J=8.8 Hz), 8.11 (1H, bs)

EXAMPLE 22

(4-(6,7-bis(palmitoyloxy)-4-thiaheptanoylamino) benzoyl)aspartic acid

To (4-(6,7-bis(palmitoyloxy)-4-thiaheptanoylamino)benzoyl)aspartic acid di-t-butyl ester as obtained in Example 21 (197 mg), trifluoroacetic acid (5 ml) was added, followed by stirring at room temperature for 4 hours. The mixture was concentrated to yield the title compound (170 mg, yield 97%) as a colorless crystal.

IR$\nu_{max}^{KBr}$ cm$^{-1}$:3450, 1730, 1640 $^1$H-NMR (CDCl$_3$)δ:0.88 (6H, t, J=6.8 Hz), 1.03–1.49 (48H, m), 1.50–1.72 (4H, m), 2.32 (2H, t, J=7.6 Hz), 2.35 (2H, t, J=7.6 Hz), 2.68 (2H, t, J=6.6 H (2H, d, J=6.6 Hz), 2.87–3.20 (4H, m), 4.17 (1H, dd, J=6.5, 12.1 Hz), 4.42 (1d J=8.8 Hz), 7.80 (2H, d, J=8.8 Hz)

EXAMPLE 23

(4-(6,7-bis(myristyloxy)-4-thiaheptanoylamino) benzoyl)glutamic acid di-t-butyl ester To a solution of (4-(6,7-dihydroxy-4-thiaheptanoylamino)benzoyl)glutamic acid di-t-butyl ester as obtained in Reference Example 6 (50 mg) in chloroform (1 ml), triethylamine (0.258 ml), myristyl chloride (0.196 ml) and dimethylaminopyridine (1 mg) were added, followed by stirring at room temperature for 24 hours. After addition of water, the reaction mixture was extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (hexane:ethyl acetate=2:1) to yield the title compound (76 mg, yield 85%) as a wax-like substance.

IR$\nu_{max}^{KBr}$ cm$^{-1}$:3400, 1730, 1640 $^1$H-NMR (CDCl$_3$) 3:0.88 (6H, t, J=7.0 Hz), 1.02–1.37 (44H, m), 1.42 (9H, s), 1.49 (9H, s), 1.52–1.73 (4H, m), 1.92–3.12 (14H, m), 4.15 (1H, dd, J=6.8, 12.0 Hz), 4.47 (1H, dd, J=3.0, 12.0 Hz), 4.60–4.73 (1H, m), 5.10–5.24 (1H, m), 7.00 (1H, d, J=7.6 Hz), 7.65 (2H, d, J=8.6 Hz), 7.65 (2H, d, J=8.6 Hz), 7.81 (2H, J=8.6 Hz), 8.10 (1H, bs)

EXAMPLE 24

(4-(6,7-bis(myristyloxy)-4,thiaheptanoylamino) benzoyl)glutamic acid

To (4-(6,7-bis(myristyloxy)-4-thiaheptanoylamino)benzoyl)glutamic acid di-t-butyl ester as obtained in Example 23 (76 mg), trifluoroacetic acid (4 ml) was added, followed by stirring at room temperature for 4 hours. The mixture was concentrated to yield the title compound (66 mg, yield 100%) as a colorless crystal.

IR$\nu_{max}^{KBr}$ cm$^{-1}$:3350, 1730, 1700, 1630

$^1$H-NMR (CDCl$_3$+5% CD$_3$OD)δ:0.88 (6H, t, J=6.6 Hz), 1.03–1.48 (40H, m), 1.51–1.72 (4H, m), 2.03–2.62 (8H, m), 2.69 (2H, t, J=7.4 Hz), 2.76 (2H, d, J=6.8 Hz), 2.95 (2H, t, J=7.4 Hz), 4.07–4.80 (3H, m), 5.10–5.26 (1H, m), 7.65 (2H, d, J=8.8 Hz), 7.80 (2H, d, J=8.8 Hz)

EXAMPLE 25

(4-(6,7-bis(stearyloxy)-4-thiaheptanoylamino) benzoyl)glutamic acid di-t-butyl ester To a solution of (4-(6,7-dihydroxy-4-thiaheptanoylamino)benzoyl)glutamic acid di-t-butyl ester as obtained in Reference Example 6 (50 mg) in chloroform (1 ml), triethylamine (0.258 ml), stearyl chloride (0.25 ml) and dimethylaminopyridine (1 mg) were added, followed by stirring at room temperature for 24 hours. After addition of water, the reaction mixture was extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (hexane:ethyl acetate=2:1) to yield the title compound (75 mg, yield 76%) as a wax-like substance.

IR$\nu_{max}^{KBr}$ cm$^{-1}$:3430, 1750, 1710, 1640

$^1$H-NMR (CDCl$_3$)δ:0.88 (6H, t, J=6.6 Hz), 1.04–1.30 (56H, m), 1.42 (9H, s), 1.49 (9H, s), 1.52–3.15 (18H, m), 4.15 (1H, dd, J=6.8, 12.2 Hz), 4.47 (1H, dd, J=3.2, 12.2 Hz), 4.59–4.73 (1H, m), 5.07–5.24 (1H, m), 6.99 (1H, d, J=7.6 Hz 7.65 (2H, d, J=8.8 Hz), 7.81 (2H, d, J=8.8 Hz), 8.08 (1H, bs)

EXAMPLE 26

(4-(6,7-bis(stearyloxy)-4-thiaheptanoylamino) benzoyl)glutamic acid

To (4-(6,7-bis(stearyloxy)-4-thiaheptanoylamino)benzoyl)glutamic acid di-t-butyl ester as obtained in Example 25 (75 mg), trifluoroacetic acid (5 ml) was added, followed by stirring at room temperature for 24 hours. The mixture was concentrated to yield the title compound (64 mg, yield 94%) as a colorless crystal.

IR$v_{max}^{KBr}$ cm$^{-1}$:1730, 1700
$^1$H-NMR (CDCl$_3$+5% CD$_3$OD)δ:0.88 (6H, t, J=6.4 Hz), 1.10–1.48 (56H, m), 1.52–1.72 (6H, m), 2.03–2.62 (8H, m), 2.69 (2H, t, J=7.2 Hz), 2.76 (2H, d, J=6.6 Hz), 2.94 (2H, t, J=7.2 Hz), 4.07–4.80 (3H, m), 5.10–5.25 (1H, m), 7.65 (2H, d, J=8.8 Hz), 7.80 (2H, d, J=8.8 Hz)

EXAMPLE 27

(4-(6,7-bis(oleinoyloxy)-4-thiaheptanoylamino) benzoyl)glutamic acid di-t-butyl ester To a solution of (4-(6,7-dihydroxy-4-thiaheptanoylamino)benzoyl)glutamic acid di-t-butyl ester as obtained in Reference Example 6 (72 mg) in chloroform (2 ml), oleic acid (0.422 ml), dicyclohexylcarbodiimide (330 mg) and dimethylaminopyridine (16 mg) were added, followed by stirring at room temperature for 48 hours. After addition of water, the reaction mixture was extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (hexane:ethyl acetate=3:1) to yield the title compound (145 mg, yield 100%) as a colorless oily substance.
IR$v_{max}^{neat}$ cm$^{-1}$: 3320, 1730, 1720, 1625
$^1$H-NMR (CDCl$_3$)δ:0.88 (6H, t, J=6.6 Hz), 1.03–1.40 (40H, m), 1.42 (9H, s), 1.49 (9H, s), 1.52–1.75 (4H, m), 1.80–3.13 (22H, m), 4.15 (H, dd, J=6.6, 12.0 Hz), 4.46 (1H, dd, J=3.0, 12.0 Hz), 4.60–4.72 (H, m), 7.00 (1H, d, J=7.4 Hz), 7.65 (2H, d, J=8.8 Hz), 7.81 (2H, d, J=8.8 Hz), 8.07 (1H, bs)

EXAMPLE 28

(4,(6,7,bis(oleinoyloxy)-4-thiaheptanoylamino) benzoyl)glutomic acid

To (4-(6,7-bis(oleinoyloxy)-4-thiaheptanoylamino)benzoyl)glutamic acid di-t-butyl ester as obtained in Example 27 (145 mg), trifluoroacetic acid (5 ml) was added, followed by stirring at room temperature for 4 hours. The mixture was concentrated to yield the title compound (130 mg, yield 100%) as a wax-like substance.
IR$v_{max}^{neat}$ cm$^{-1}$:3330, 1710, 1640
$^1$H-NMR (CDCl$_3$+ 5% CD$_3$OD) 3:0.88 (6H, t, J=6.6 1.02–1.50 (40H, m), 1.50–2.80 (20H, m), 2.68 (2H, t, J=7.6 Hz), 2.76 (2H, d, J=6.8 Hz), 2.95 ( 2H, t, J=7.6 Hz), 4.10–5.45 (8H, m), 7.67 (2H, d, J=8.8 Hz), 7.80 (2H, d, J=8.8 Hz)

EXAMPLE 29

4-(7-octadecylcarbamoyoxy-6-palmitoyloxy4-thiaheptanoylamino)benzoyl-glutamic acid di-t-butyl ester To a solution of phosphorus trichloride (19 mg) in pyridine (4 ml), 4-aminobenzoyl-glutamic acid di-t-butyl ester (106 mg) was added, followed by stirring at room temperature for 1 hour. To this mixture, 7-octadecylcarbamoyloxy-6-palmitoyloxy-4-thiaheptanoic acid as obtained in Reference Example 9 (200 mg) was added, followed by stirring at 50° C. for 1 hour. After solvent concentration under reduced pressure, the resulting residue was purified by silica gel column chromatography (n-hexane:ethyl acetate - 2:1) to yield the title compound (152 mg, yield 51%) as a colorless wax-like substance.

IR (Neat)υ: 3310, 9.920, 2850, 1730, 1700, 1640, 1600, 1525, 1500, 1460, 1365, 1250, 1150 cm$^{-1}$
$^1$ H-NMR (CDCl$_3$)δ: 0.88 (6H, t, J=6.8 Hz), 1.25 (54H, s), 1.42 (9H, s), 1.49 (9H, s), 1.40–1.70 (4H, m), 2.00–2.50 (6H, m), 2.65–3.10 (6H, m), 3.18 J=6.4 Hz), 4.12 (1H, m), 4.48 (1H, dd, J=12.4, 3.4 Hz), 4.66 (1H, m), 4.79 (1 H, brt, J=5.0 Hz), 5.18 (1H, m), 6.98 (1H, d, J=7.0 Hz), 7.67 (2H, d, J=8.8 Hz), 7.80 (2H, d, J=8.8 Hz), 8.45 (1H, brs)

EXAMPLE 30

4-(7-octadecylcarbamoyloxy-6-palmitoyloxy-4-thiaheptano.ylamino)benzoyl-glutamic acid A solution of 4-(7-octadecylcarbamoyloxy-6-palmitoyloxy-4-thiaheptanoylamino)benzoyl-glutamic acid di-t-butyl ethyl as obtained in Example 29 (150 mg) in trifiuoroacetic acid (2 ml)-dichloromethane (0.5 ml) was stirred at room temperature for 1 hour. After solvent concentration under reduced pressure, the resulting residue was crystallized from chloroform-methanol-water to yield the title compound (109 mg, yield 81%) as a colorless powder.
IR (Neat)υ: 2920, 2850, 1730, 1710, 1700, 1680, 1650, 1560, 1540, 1520, 1500, 1460 cm$^{-1}$
$^1$H-NMR (CDCl$_3$-trifluoroacetic acid)δ:0.88 (6H, t, J=6.8 Hz), 1.25 (54H, s), 1.40–1.70 (4H, m), 2.10–2.50 (4H, m), 2.60–2.85 (6H, m), 2.90–3.05 (2H, 3.05–3.20 (2H, m), 4.23 (1H, m), 4..44 (1H, m), 4.88 (1H, m), 5.21 (1H, m), (1H, d, J=6.8 Hz), 7.63 (2H, d, J=8.8 Hz), 7.74 (2H, d, J=8.8 Hz), 8.71 (1 H, brs)

EXAMPLE 31

4-[6,7-bis(octadecylcarbamoyloxy)-4-thiaheptanoylamino]benzoylglutamic acid di-t-butyl ester To a solution of phosphorus trichloride (19 mg) in pyridine (4 ml), 4-aminobenzoyl-glutamic acid di-t-butyl ester (106 mg) was added, followed by stirring at room temperature for 1 hour. To this mixture, 6,7-bis(octadecylcarbamoyloxy)- 4-thiaheptanoic acid as obtained in Reference Example 10 (216 mg) was added, followed by stirring at 50° C. for 1 hour. After solvent concentration under reduced pressure, the resulting residue was purified by silica gel preparative TLC (dichloromethane:methanol=50:1×3) to yield the title compound (102 mg, yield 32%) as a colorless solid.
IR (Neat)[: 3320, 2920, 2850, 1725, 1700, 1670, 1650, 1630, 1600, 1530, 1505, 1465, 1370, 1250, 1150 cm$^{-1}$
$^1$H-NMR (CDCl$_3$)δ:0.88 (6H, t, J=6.8 Hz), 1.25 (60H, s), 1.42 (9H, s), 1.49 (9H, s), 1.40–1.60 (4H, m), 1.90–2.50 (4H, m), 2.60–3.25 (10H, m), 4.17 (1H, dd, J=12.0, 6.4 Hz), 4.42 (1H, dd, J=12.0, 2.8 Hz), 4.66 (1H, m), 4.79 (1H, brt, J=6.4 Hz), 4.90 (1H, brt, J=6.6 Hz), 5.00 (1H, m), 6.97 (1H, d, J=7.4 Hz) 7.69 (2H, d, J=8.8 Hz), 7.79 (2H, d, J=8.8 Hz), 8.70 (1H, brs)

EXAMPLE 32

4-[6,7-bis(octadecylcarbamoyloxy)-4thiaheptanoylamino]benzoylglutamic acid

A solution of 4-[6,7-bis(octadecylcarbamoyloxy)-4-thiaheptanoylamino] benzoyl-glutamic acid di-t-butyl ester as obtained in Example 31 (100 mg) in trifiuoroacetic acid (2 ml)-dichloromethane (0.5 ml) was stirred at room temperature for 1 hour. After solvent concentration under reduced pressure, the resulting residue was crystallized from chloroform-methanolwater to yield the title compound (99 mg, yield 100%) as a colorless powder.

IR (Neat)υ:2920, 2850, 1715, 1700, 1680, 1650, 1630, 1560, 1540, 1520, 1500, 1460 cm$^{-1}$ $^1$H-NMR (CDCl$_3$-trifluoroacetic acid)δ:0.88 (6H, t, J=6.6 Hz), 1.25 (60H, s), 1.40–1.60 (4H, m), 2.10–2.55 (4H, m), 2.65–2.85 (6H, m), 2.90–3.05 (2H,m), 3.15 (2H, t, J=6.6 Hz), 4.20–4.55 (2H, m), 4.95 (1H, m), 5.09 (1H, m), 7.35 (1 H, d, J=7.2 Hz), 7.66 (2H, d, J=8.2 Hz), 7.79 (2H, d, J=8.2 Hz), 8.70 (1H, brs)

EXAMPLE 33

6,7-bis(palmitoyloxy),4-thia-2(E)-heptenoyl, Gly-Gly-Gly-Glu(OBu$^t$)-OBu$^t$ To a solution of 6,7-bis(palmitoyloxy)-4-thia-2(E)-heptenoic acid as obtained in Reference Example 13 (200 mg) and Gly-Gly-Gly-Glu(OBu$^t$)-OBu$^t$ hydrochloride (171 mg) in dimethylformamide (10 ml), diethylphosphorocyanidate (75 mg) was added, followed by stirring for 10 minutes. To this mixture, triethylamine (123 mg) was added, followed by stirring at room temperature overnight. After solvent concentration under reduced pressure, the residue was diluted with chloroform, washed with water and saturated saline, and dried over magnesium sulfate, and the solvent was concentrated. The resulting residue was purified by silica gel column chromatography (chloroform:methanol=50:1) to yield the title compound (306 mg, yield 94%) as a wax-like substance.

IR (Neat)υ: 3300, 2920, 2850, 1730, 1695, 1630, 1590, 1520, 1430, 1365, 1250, 1150 cm$^{-1}$ $^1$H-NMR (CDCl$_3$)δ:0.88 (6H, t, J=6.8 Hz), 1.25 (48H, s), 1.44 (9H, s), 1.47 (9H, s), 1.50–1.70 (4H, m), 1.80–2.40 (8H, m), 3.05 (2H, t, J=4.6 Hz), 4.00– 4.15 (6H, m), 4.18 (1H, dd, J=12.4, 6.0 Hz), 4.36 (1H, dd, J=12.4, 3.2 Hz), 4.47 ( 1H, m), 5.21 (1H, m), 6.07 (1H, d, J=15.0 Hz), 6.75 (1H, brs), 7.19 (1H, brs), 7.35 (1H, d, J=7.4 Hz), 7.53 (1H, brs), 7.60 (1H, d, J=15.0 Hz)

EXAMPLE 34

6,7-bis(palmitoyloxy)-4-thia-2(E)-heptenoyl-Gly-Gly-Gly-Glu

To a solution of 6,7-bis(palmitoyloxy)-4-thia-2(E)-heptenoyl-Gly-Gly-Gly-Glu(OBu$^t$)-OBu$^t$ as obtained in Example 33 (295 mg) in dichloromethane (1 ml), trifluoroacetic acid (4 ml) was added, followed by stirring at room temperature for 1 hour. After solvent concentration under reduced pressure, the resulting residue was dissolved in chloroform (1 ml). To this solution, methanol (10 ml) and then water (3 ml) were added. The separating crystal was collected by filtration, washed with water, and dried, to yield the title compound (234 mg, yield 89%) as a colorless powder.

IR (KBr)υ: 3282, 2920, 2852, 1735, 1631, 1565, 1463, 1419, 1251, 1226, 1168

$^1$H-NMR (CDCl$_3$-trifluoroacetic acid) δ:0.88 (6H, t, J=6.6 Hz), 1.26 (48H, s), 1.50–1.70 (4H, m), 2.05–2.45 (6H, m), 2.55 (2H, t, J=6.6 Hz), 2.97 (1H, dd, J=14.4, 7.2 Hz), 3.14 (1H, dd, J=14.4, 6.4 Hz), 4.00–4.35 (7H, m), 4.45 (1H, dd, J=12.0, 2.6 Hz), 4.68 (1H, m), 5.25 (1H, m), 6.08 (1H, d, J=15.2 Hz), 7.32 (1H, brs), 7.63 (1H, brs), 7.65 (1H, d, J=15.2 Hz), 7.75–7.85 (2H, m)

EXAMPLE 35

6,7-bis(palmitoyloxy)-4-thia-2(Z)-heptenoyl-Gly-Gly-Gly-Glu(OBu$^t$)-OBu$^t$ To a solution of 6,7-bis(palmitoyloxy)-4-thia-2(Z)-heptenoic acid as obtained in Reference Example 15 (200 mg) and Gly-Gly-Gly-Glu(OBu$^t$)-OBu$^t$ hydrochloride (171 mg) in dimethylformamide (10 ml), DEPC (75 mg) was added, followed by stirring for 10 minutes. To this mixture, triethylamine (123 mg) was added, followed by stirring at room temperature overnight. After solvent concentration under reduced pressure, the resulting residue was diluted with chloroform, washed with water and saturated saline, and dried over magnesium sulfate, and the solvent was concentrated. The resulting residue was purified by silica gel column chromatography (chloroform:methanol=50:1) to yield the title compound (310 mg, yield 95%) as a wax-like substance.

IR (Neat)υ: 3300, 2920, 2850, 1730, 1630, 1520, 1360, 1250, 1155 cm$^{-1}$ $^1$-NMR (CDCl$_3$)δ:0.88 (6H, t, J=6.8 Hz), 1.25 (48H, s), 1.44 (9H, s), 1.45 (9H, s), 1.50–1.70 (4H, m), 1.80–2.20 (2H, m), 2.31 (6H, t, J=7.6 Hz), 2.92 2H, d,J=6.2 Hz), 3.90–4.10 (6H, m), 4.18 (1H, dd, J=12.1, 5.4 Hz), 4.30–4.50 ( 2H, m), 5.12 (1H, m), 5.99 (1H, d, J=10.0 Hz), 6.93 (1H, d, J=10.0 Hz), 7.12 (1H, brs), 7.20 ( 1H, d, J=7.8 Hz), 7.44 ( 1H, brs), 7.55 (1H, brs)

EXAMPLE 36

6,7-bis(palmitoyloxy)-4-thia-2(Z)-heptenoyl-Gly-Gly-Gly-Glu

To 6,7-bis(palmitoyloxy)-4-thia-2(Z)-heptenoyl-Gly-Gly-Gly-Glu(OBu$^t$)-OBu$^t$ as obtained in Example 35 (300 mg) in dichloromethane (1 ml), trifluoroacetic acid (4 ml) was added, followed by stirring at room temperature for 1 hour. The solvent was concentrated under reduced pressure. The resulting residue was dissolved in chloroform (1 ml). To this solution, methanol (10 ml) and then water (3 ml) were added. The separating crystal was collected by filtration, washed with water, and dried, to yield the title compound (258 mg, yield 96%) as a colorless powder.

IR (KBr)υ: 3290, 2920, 2852, 1735, 1635, 1560, 1461, 1419, 1251, 1228, 1172 cm$^{-1}$ $^1$H-NMR (CDCl$_3$-trifluoroacetic acid)δ:0.88 (6H, t, J=6.6 Hz), 1.26 (48H, s), 1.50–1.70 (4H, m), 2.00–2.45 (6H, m), 2.50–2.65 (2H, m), 2.90–3.00 (2H, m), 4.00–4.50 (8H, m), 4.67 (1H, m), 5.20 (1H, m), 5.93 (1H, d, J=9.8 Hz), 7.05–7.20 (2H, m), 7.63 (1H, d, J=9.8 Hz), 7.75–7.85 (1H, m), 8.02 (1H, brs)

EXAMPLE 37

N(alpha)-Boc-N(delta)-[6,7-bis(nalmi toyloxy)-4-thia-2(E)-heptenoyl]-Orn-Gly-Gly-Glu(OBu$^t$)-OBu$^t$ A solution of 6,7-bis(palmitoyloxy)-4-thia-2(E)-heptenoic acid as obtained in Reference Example 13 (150 mg), N(alpha)-Boc-Orn-Gly-Gly-Glu(OBu$^t$)-OBu$^t$ (170 mg), DEPC (60 mg) and triethylamine (93 mg) in dimethylformamide (6 ml) was stirred at room temperature for 5 hours. After solvent concentration under reduced pressure, the resulting residue was purified by silica gel column chromatography (chloroform:methanol = 50:1) to yield the title compound (151 mg, yield 54%) as a colorless wax-like substance.

IR (Neat)υ: 3300, 2920, 2850, 1730, 1680, 1640, 1580, 1530, 1455, 1365, 1250, 1160 cm$^{-1}$
$^1$H-NMR (CDCl$_3$) δ:0.88 (6H, t, J=6.8 ttz), 1.25 (50H, s), 1.43 (9H, s), 1.44 (9H, s), 1.50–1.70 (6H, m), 1.70–2.20 (2H, m), 2.33 (6H, t, J=7.8 Hz), 2.90–3.10 (2H, m), 3.29 (1H, m), 3.47 (1H, m), 3.96 (4H, d, J=5.4 Hz), 4.00–4.50 (4H, m), 5.20 (1H, m), 5.54 (1H, d, J=7.0 Hz), 5.96 (1H, d, J=14.8 Hz), 6.13 (1H, m) 6.99 (1H, d, J=7.4 Hz), 7.13 (1H, m), 7.37 (1H, m), 7.49 (1H, d, J=14.8 Hz)

EXAMPLE 38

N(delta)-[6,7,bis(palmitoyloxy)-4-thia-2(E)-heptenoyl]-Orn-Gly-Gly-Glu hydrochloride A solution of N(alpha)-Boc-N(delta)-[6,7-bis(palmitoyloxy)-4-thia-2(E)heptenoyl]-Orn-Gly-Gly-Glu(OBu$^t$)-OBu$^t$ as obtained in Example 37 (145 mg) in a 4N solution of hydrochloric acid in ethy acetate (5 ml) was stirred at room temperature for 3 hours, after which the solvent was distilled off under reduced pressure, to yield the title compound (122 mg, yield 98%) as a colorless powder.
IR (KBr)υ: 3360, 2920, 2850, 1725, 1680, 1665, 1650, 1535, 1460, 1260, 1240, 1170 cm$^{-1}$
$^1$H-NMR (CDCl$_3$-trifluoroacetic acid)δ: 0.88 (6H, t, J=6.6 Hz), 1.25 (50H, s), 1.70–2.30 (2H, m), 2.40 (6H, m), 2.90–3.55 (5H, m), 3.85–4.75 (7H, m), 5.2 (1H, m), 6.05 (1H, m), 7.35–8.40 (5H, m)

EXAMPLE 39

4-[6,7-bis(palmitoyloxy)-4-thiaheptanoylaminomethyl] benzoylglutamic acid di-t-butyl ester To a solution of 6,7-bis(palmitoyloxy)-4-thiaheptanoic acid as obtained in Reference Example 4 (210 mg), 4-(aminomethyl)benzoyl-glutamic acid di-t-butyl ester hydrochloride (144 mg), diethylphosphorocyanidate (75 mg) and triethylamine (93 mg) in dimethylformamide (10 ml) was stirred at room temperature for 30 minutes. After solvent concentration under reduced pressure, the resulting residue was purified by silica gel column chromatography (n-hexane:ethyl acetate=8:2) to yield the title compound (328 mg, yield 99%) as a colorless wax-like substance.
IR (Neat)υ: 3300, 2920, 2850, 1730, 1650, 1530, 1500, 1460, 1360, 1250, 1150
$^1$H-NMR (CDCl$_3$) 3:0.88 (6H, t, J=6.8 Hz), 1.25 (48H, s), 1.42 (9H, s), 1.49 (9H, s), 1.50–1.70 (4H, m), 1.95–2.50 (8H, m), 2.55 (2H, t, J=7.4 Hz), 2.72 (2H, d, J=6.8 Hz), 2.93 (2H, t, J=7.4 Hz), 4.13 (1H, dd, J=12.0, 6.4 Hz), 4.38 (1H, dd, J=12.0, 3.2 Hz), 4.50 (2H, d, J=5.8 Hz), 4.66 (1H, m), 5.15 (1H, m), 6.32 (1H, brt, J=5.8 Hz), 7.04 (1H, d, J=7.6 Hz), 7.36 (2H, d, J =8.2 Hz), 7.79 (2H, d, J=8.2 Hz)

EXAMPLE 40

4-[6,7,bis(palmitoyloxy)-4-thiaheptanoylaminomethyl] benzoylglutamic acid

A solution of 4-[6,7-bis(palmitoyloxy)-4-thiaheptanoylaminomethyl] benzoyl-glutamic acid di-t-butyl ester as obtained in Example 39 (325 mg) in dichloromethane (0.5 ml)-trifluoroacetic acid (1 ml) was stirred at room temperature for 30 minutes. After solvent concentration under reduced pressure, the resulting residue was crystallized from methanol-water to yield the title compound (231 mg, yield 80%) as a colorless powder.
IR (KBr)υ: 2918, 2850, 1737, 1639, 1544, 1467, 1243, 1222, 1199, 1174 cm$^{-1}$
$^1$H-NMR (CDCl$_3$)δ:0.88 (6H, t, J=6.6 Hz), 1.25 (48H, s), 1.50–1.70 (4H, m), 1.90–2.65 (10H, m), 2.71 (2H, d, J=6.6 Hz), 2.87 (2H, t, J=6.2 Hz), 4.12 (1H, dd, J=11.6, 5.8 Hz), 4.25–4.50 (3H, m), 4.63 (1H, m), 5.13 (1H, m), 7.16 (2H, d, J=7.8 Hz), 7.31 (1H, brs), 7.61 (2H, d, J = 7.8 Hz), 7.79 (1H, d, J=6.0 Hz)

EXAMPLE 41

N-(5,6-bis(palmitoyloxy)-3-thiahexanesulfonyl]-N-t-butyloxycarbonyl-Gly-Gly-Gly-Glu(O$^t$Bu)$_2$ N-(5,6-dihydroxy-3-thiahexanesulfonyl)-N-t-butyloxycarbonyl-Gly-Gly-Gly-Glu(OtBu)$_2$ as obtained in Reference Example 18 (192 mg, 0.267 mM) and dimethylaminopyridine (68.4 mg, 0.56 mM) in dichloromethane (2 ml) were added to a solution of palmitoyl chloride (154 mg, 0.56 mM) in dichloromethane (1 ml), followed by stirring under ice cooling conditions for 1 hour. To this mixture, chloroform (20 ml), H20 (20 m) and a saturated aqueous solution of sodium hydrogen carbonate (1 ml) were added. With vigorous stirring, the organic layer was collected, purified by silica gel column (12 g), (ethyl acetate-n-hexane (7:3)) to yield the title compound (193 mg, yield 62.9%) as a colorless solid.
IR (Neat)υ: 3320, 2920, 2850, 1735, 1660, 1530, 1460, 1420, 1365, 1245, 1140, 1070, 1020 cm$^{-1}$
$^1$H-NMR (CDCl$_3$)δ: 0.879 (6H, t, J=6.6 Hz), 1.254 (48H, s), 1.443 (9H, s), 1.469 (9H, s), 1.516 (9H, s), 1.605 (4H, m), 1.80–2.25 (2H, m), 2.315 (6H, m) 2.779 (2H, dd, J=5.2, 6.8 Hz), 3.051 (2H, dd, J=6.6, 11.4 Hz), 3.890 (2H, dd, J=5.4, 8.2 Hz), 4.013 (4H, t, J=5.8 Hz), 4.190 (1H, dd, J=6.0, 10.0 Hz), 4.403 (2H, s), 4.449 (1H, m), 5.179 (1H, m), 6.711 (1H, t, J=5.0 Hz), 6.819 (1H, t, J=5.2 Hz), 6.852 (1H, d, J=7.6 Hz)

EXAMPLE 42

N-[5,6-bis(palmitoyloxy)73-thiahexanesulfonyl]-Gly-Gly-Gly-Glu(OH)$_2$

N-[ 5,6-bis(palmi toyloxy)-3-thiahexanesulfonyl ]-N-t-butyloxycarbonyl-Gly-Gly-Gly-Glu(OtBu) 2 as obtained in Example 41 (53 mg, 0.045 mM) was dissolved in dichloromethane (1 ml) and trifluoroacetic acid (1 ml), followed by stirring at room temperature for 1 hour. The reaction mixture was concentrated to dryness under reduced pressure; the resulting residue was purified by silica gel column (5 g) (chloroform-methanol-water (65:25:4)) to yield the title compound (44 mg, yield 100%) as a colorless solid.
IR (Neat)υ: 3320, 2920, 2850, 1735, 1655, 1540, 1460, 1410, 1370, 1325, 1295, 1260, 1240, 1220, 1190, 1150 cm$^{-1}$
$^1$H-NMR (DMSO-d$_6$)δ: 0.880 (6H, t, J=6.6 Hz), 1.233 (48H, s), 1.480 (4H, m), 1.60–2.10 (2H, m), 2.264 (6H, t, J=7.0 Hz), 2.62–3.00 (4H, m), 3.280 (2H, m), 3.64–3.85 (6H, m), 4.00–4.40 (3H, m), 5.121 (1H, m), 7.604 (1H, t, J=6.0 8.05–8.35 (3H, m)

EXAMPLE 43

6-[N-(5,6-bis(palmitoyloxy)-3-thiahexanesulfonyl)-N-(t-butyloxycarbonyl)amino] hexanoylglutamic acid di-t-butyl ester 6-[N-( 5,6-dihydroxy-3-thiahexanesulfonyl )-N-( tbutyloxycarbonyl)amino] -hexanoylglutamic acid di-t-butyl ester as obtained in Reference Example 21 (87 mg, 0.13 mM), dimethylaminopyridine (32 mg, 0.26 mM) and triethylamine (30 mg, 0.30 mM) were dissolved in dichloromethane (1.0 ml). To this solution, a solution of palmitoyl chloride (89 mg, 0.325 mM) in dichloromethane (0.5 ml) was added, followed by stirring under ice cooling conditions for 1 hour and at room temperature for 30 minutes. To the reaction mixture, methanol (0.5 ml) was added, followed by stirring at room temperature for 30 minutes, after which the mixture was concentrated to dryness under reduced pressure. The resulting residue was passed through a purified by silica gel column (5 g) (ethyl acetate-n-hexane (1:4) to yield the title compound (141 mg, yield 94.6%) as a colorless solid.

IR (Neat)$\upsilon$: 3380, 3300, 2910, 2850, 1730, 1650, 1535, 1525, 1460, 1390, 1360, 1350, 1275, 1250, 1210, 1145 cm$^{-1}$
$^1$H-NMR (CDCl$_3$)$\delta$:0.879 (6H, t, J=6.0 Hz), 1.254 (50H, s), 1.443 (9H, s), 1.446 (9H, s), 1.531 (9H, s), 1.639 (8H, m), 1.80–2.13 (2H, m), 2.13–2.40 (6H, m), 2.749 (2H, dd, J=1.8, 6.2 Hz), 2.927 (2H, m), 3.656 (4H, m), 4.159 (1H, dd, J=5.8, 12.0 Hz), 4.338 (1H, dd, J=3.6, 12.0 Hz), 4.469 (1H, m), 5.140 (1H, m), 6.142 (1H, d, J=7.6 Hz)

EXAMPLE 44

6-7[N7(5,6-bis(palmitoyloxy)-3-thiahexanesulfonyl) amino]-hexanoylglutamic acid

6-[N-( 5,6-bis(palmi toyloxy)-3-thiahexanesulfonyl)-N-(tbutyloxycarbonyl)amino] hexanoylglutamic acid di-t-butyl ester as obtained in Example 43 (141 mg, 0.123 mM) was dissolved in dichloromethane (2 ml). To this solution, trifluoroacetic acid (1 ml) was added, followed by stirring at room temperature for 2 hours. To the reaction mixture, toluene (1 ml) was added, followed by two cycles of concentration to dryness under reduced pressure, to yield the title compound (112 mg, yield 97.6%) as a colorless powder.
IR (KBr) $\upsilon$: 3300, 2920, 2850, 1735, 1630, 1540, 1460, 1410, 1375, 1320, 1290, 260, 1240, 1215, 1170, 1140, 1090 cm$^{-1}$
$^1$H-NMR (CDCl$_3$)$\delta$:0.879 (6H, t, J=6.6 Hz), 1.256 (50H, s), 1.608 (8H, m), 1.95–2.25 (2H, m), 2.323 (6H, m), 2.750 (2H, d, J=6.4 Hz), 2.940 (2H, m), 3.141 (2H, bs), 3.267 (2H, m), 4.179 (1H, dd, J= 6.4, 12.0 Hz), 4.394 (1H, dd, J=2.8, 2.0 Hz), 4.622 (1H, m), 5.160 (1H, m), 5.460 (1H, bs), 7.032 (1H, d, J=7.0 Hz

EXAMPLE 45

4-[6,7-bis(palmitoyloxy)4-thiaheptanoylamino]benzoic acid t-butyl ester

A solution of 6,7-bis(palmitoyloxy)-4-thiaheptanoic acid as obtained in Reference Example 4 (2.0 g), 4-aminobenzoic acid t-butyl ester (600 mg) and phosphorus trichloride (207 mg) in pyridine (40 ml) was stirred at room temperature for 30 minutes. After solvent concentration under reduced pressure, the resulting residue was purified by silica gel column chromatography (chloroform) to yield the title compound (2.157 g, yield 99%) as a colorless solid.
IR (Neat)$\upsilon$: 3330, 2920, 2850, 1730, 1705, 1590, 1520, 1450, 1400, 1360, 1290, 1250, 1160, 1110, 900,730 cm$^{-1}$
$^1$H-NMR (CDCl$_3$)$\delta$:0.88 (6H, t, J=6.8 Hz), 1.25 (48H, s), 1.59 (9H, s), 2.25– 2.40 (4H, m), 2.65–2.80 (4H, m), 2.80–3.10 (2H, m), 4.15 (1H, dd, J=12.0, 6.8 Hz), 4.46 (1H, dd, J=12.0, 3.2 Hz), 5.17 (1H, m), 7.62 (2H, d, J=8.8 Hz), 7.95 (2H, d, J=8.8 Hz), 8.07 (1H, brs)

EXAMPLE 46

4-[6,7-bis(palmitoyloxy)-4-thiaheptanoylamino] benzoyl-γ-t-butyl ester-glutamyl-glutamic acid di-t-butyl ester A solution of 4-[6,7-bis(palmitoyloxy)-4-thiaheptanoylamino]benzoic acid t-butyl ester as obtained in Example 45 (1.05 g) in chloroform (5 ml)-trifluoroacetic acid (6 ml) was stirred at room temperature for 2 hours. The solvent was distilled off under reduced pressure, and the residue was crystallized from methanol-water to yield 4-[6,7-bis(palmitoyloxy)-4-thiaheptanoylamino] benzoic acid (992 mg, yield 100%) as a colorless crystal. A solution of 4-[6,7-bis(palmitoyloxy)-4-thiaheptanoylamino]benzoic acid as obtained above (200 mg), 7-t-butyl ester-glutamyl-glutamic acid di-t-butyl ester as obtained in Reference Example 26 (126 mg), DEPC (63 mg) and triethylamine (78 mg) in dimethylformarnide (6 ml) was stirred at room temperature for 30 minutes. The solvent was concentrated; the resulting residue was purified by silica gel column chromatography (n-hexane:ethyl acetate:chloroform=2:1) to yield the title compound (210 mg, yield 68%) as a colorless amorphous substance.
IR (Neat)$\upsilon$: 3300, 2920, 2850, 1730, 1660, 1630, 1525, 1500, 1360, 1250, 1150 cm$^{-1}$
$^1$H-NMR (CDCl$_3$)$\delta$:0.88 (6H, t, J=6.8 Hz), 1.25 (48H, s), 1.41 (9H, s), 1.44 (9H, s), 1.46 (9H, s), 1.50–1.70 (4H, m), 1.80–3.20 (18H, m), 4.15 (1H, dd J=12.0, 7.0 Hz), 4.35–4.50 (2H, m), 4.66 (1H, m), 5.17 (1H, m), 7.23 (1H, d, J=7.6 Hz), 7.35 (1H, d, J=7.0 Hz), 7.63 (2H, d, J=8.8 Hz), 7.80 (2H, d, J= 8.8 Hz), 8.29 (1H, brs)

EXAMPLE 47

4-[6,7-bis(palmitoyloxy)-4-thiaheptanoylamino] benzoylglutamylglutamic acid

A solution of 4-[6,7-bis(palmitoyloxy)-4-thiaheptanoylamino]benzoyl-γ-t -butyl ester-glutamyl-glutamic acid di-t-butyl ester as obtained in Example 46 (205 mg) in trifluoroacetic acid (3 ml) was stirred at room temperature for 2 hours. After the solvent was distilled off under reduced pressure, the resulting residue was crystallized from methanol-water to yield the title compound (165 mg, yield 94%) as a colorless crystal.
IR (KBr)$\upsilon$: 3322, 2919, 2850, 1735, 1666, 1631, 1538, 1409, 1213 cm$^{-1}$ 1H-NMR (CDCl$_3$-trifluoroacetic acid) 3:0.88 (6H, t, J=6.8 Hz), 1.25 (48H, s), 1.50–1.70 (4H, m), 2.00–3.05 (18H, m), 4.18 (1H, dd, J = 12.0, 6.4 Hz), 4.48 (1 H, dd, J=12.0, 2.2 Hz), 4.67 (1H, m), 4.91 (1H, m), 5.19 (1H, m), 7.60 (2H, d, J=8.8 Hz), 7.70–8.05 (4H, m), 8.65 (1H, brs)

EXAMPLE 48

4-[6,7-bis(palmitoyloxy)-4-thia-2(E)-heptenoylaminomethyl]benzoyl-glutamic acid di-t-butyl ester A solution of 6,7-bis(palmitoyloxy)-4-thia-2(E)-heptenoic acid as obtained in Reference Example 13 (150 mg), 4-(aminomethyl)benzoylglutamic acid di-t-butyl ester hydrochloride (110 mg), DEPC (56 mg) and triethylamine (92 mg) in dimethylformamide (7 ml) was stirred at room temperature for 30 minutes. After the solvent was concentrated under reduced pressure, the resulting residue was purified by silica gel column chromatography (n-hexane- :ethyl acetate=1:1) to yield the title compound (234 mg, yield 99%) as a colorless amorphous solid.
IR (Neat)υ: 3300, 2920, 2850, 1735, 1640, 1580, 1540, 1460, 1365, 1250, 1150 cm$^{-1}$
$^1$H-NMR (CDCl$_3$)δ:0.88 (6H, t, J=6.6 Hz), 1.25 (48H, s), 1.42 (9H, s), 1.49 (9H, s), 1.50–1.70 (4H, m), 1.95–2.50 (8H, m), 2.96 (1H, dd, J=14.4, 7.2 Hz), 3.08 (1H, dd, J=14.4, 6.4 Hz), 4.20 (1H, dd, J = 12.0, 5.4 Hz), 4.35 (1H, dd, J=12.0, 3.6 Hz), 4.55 (2H, d, J=5.8 Hz), 4.65 (1H, m), 5.19 (1H, m), 5.94 (1H, brs), 6.00 (1H, d, J=18.6 Hz), 7.02 (1H, d, J=7.6 Hz), 7.34 (2H, d, J=8.2 Hz), 7.57 (1H, d, J=18.6 Hz), 7.77 (2H, d, J=8.2 Hz))

EXAMPLE 49

4-[6,7-bis(palmitoyloxy)-4-thia-2(E)-heptenoylaminomethyl]benzoylglutamic acid

A solution of 4-[6,7-bis(palmitoyloxy)-4-thia-2(E)-heptenoylaminomethyl] benzoyl-glutamic acid di-t-butyl ester as obtained in Example 48 (230 mg) in trifluoroacetic acid (2 ml) was stirred at room temperature for 1 hour. After the solvent was distilled off under reduced pressure, the resulting residue was crystallized from methanol-water to yield the title compound (188 mg, yield 92%) as a colorless crystal.
IR (KBr)υ: 3296, 2919, 2852, 1739, 1633, 1575, 1544, 1247, 1180 cm$^{-1}$
$^1$H-NMR (CDCl$_3$)δ:0.88 (6H, t, J=6.6 Hz), 1.25 (48H, s), 1.50–1.70 (4H, m), 1.95–2.50 (8H, m), 2.90–3.10 (2H, m), 4.16 (1H, dd, J = 12.0, 5.4 Hz), 4.30–4.45 (3H, m), 4.60 (1H, m), 5.20 (1H, m), 6.06 (1H, d, J=15.2 Hz), 7.10 (2H, d, J=8.2 Hz), 7.10–7.20 ( 1H, m), 7.50–7.65 ( 3H, m), 7.82 ( 1H, m)

EXAMPLE 50

4-(6,7-bis(palmitoyloxy)-4- thiaheptanoyl)amino-2-fluorobenzoylglutamic acid di-t-butyl ester To a solution of 4-amino-2-fluorobenzoylglutamic acid di-t-butyl ester (181 mg) in pyridine (2.3 ml), phosphorus trichloride (0.020 ml) was added, followed by stirring at room temperature for 2 hours. To this mixture, 6,7-bis(palmitoyloxy)- 4-thiaheptanoic acid as obtained in Reference Example 24 (150 mg) was added, followed by stirring at room temperature for 24 hours. The reaction mixture was diluted with water, extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (hexane:ethyl acetate=2:1) to yield the title compound (205 mg, yield 87%) as a wax-like substance.
IRυ$_{max}^{neat}$ cm$^{-1}$: 1730 $^1$H-NMR (CDCl$_3$)δ:0.88 (6H, t, J=6.8 Hz), 1.00–1.38 (48H, m), 1.42 (9H, s), 1.50 (9H, s), 1.53–1.72 (4H, m), 1.85–3.15 (14H, m), 4.14 (H, dd, J=7.0, 12.0 Hz), 4.49 (1H, dd, J=3.0, 12.0 Hz), 4.67–4.81 (1H, m), 5.10–5.23 (1H, m), 7.16 (1H, dd, J=2.2, 8.8 Hz), 7.32 (1H, dd, J=7.2, 13.6 Hz), 7.81 (1H, dd, J=2.2, 14.4 Hz), 8.02 (1H, dd, J =8.8, 8.8 Hz), 8.26 (1H, bs)

EXAMPLE 51

4-(6,7-bis(palmitoyloxy)-4- thiaheptanoyl)amino-2-fluorobenzoylglutamic acid

A solution of 4-(6,7-bis(palmitoyloxy)-4-thiaheptanoyl)amino-2-fluorobenzoylglutamic acid di-t-butyl ester as obtained in Example 50 (205 mg) in trifluoroacetic acid (5 ml) was stirred at room temperature for 4 hours, followed by concentration, to yield the title compound (183 mg, yield 100%) as a colorless crystal.
IRυ$_{max}^{neat}$ cm$^{-1}$: 3410, 1730, 1620
$^1$H-NMR (CDCl$_3$+ 5% CD$_3$OD)δ:0.88 (6H, t, J=7.0 Hz), 1.03–1.49 (48H, m), 1.53–1.72 (4H, m), 2.02–2.59 (4H, m), 2.33 (2H, t, J=7.8 Hz), 2.35 (2H, t, J= 7.4 Hz), 2.69 (2H, t, J=7.2 Hz), 2.75 (2H, d, J=6.6 Hz), 2.94 (2H, t, J=7.2 Hz), 4.17 (1H, dd, J=6.4, 12.2 Hz), 4.42 (1H, dd, J=3.0, 12.2 Hz), 4.72–4.85 (1H, m), 5.10–5.25 (1H, m), 7.21 (1H, dd, J=2.0, 8.8 Hz), 7.55 (1H, dd, J=7.2, 12.0 Hz), 7.80 ( 1H, dd, J=2.0, 12.6 Hz), 7.93 ( 1H, dd, J = 8.8, 8.8 Hz)

EXAMPLE 52

4-(6,7-bis(dodecanoyloxy)-4-thiaheptanoylamino)benzoylglutamic acid di-t-butyl ester To a solution of 4-(6,7-dihydroxy-4-thiaheptanoyl-amino)benzoylglutamic acid d-t-butyl ester as obtained in Reference Example 6 (76 mg) in chloroform (1.4 ml), triethylamine (0.39 ml), dodecanoyl chloride (307 mg) and dimethylaminopyridine (1 mg) were added, followed by stirring at room temperature for 24 hours. After addition of water, the reaction mixture was extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (hexane:ethyl acetate=2:1) to yield the title compound (94 mg, yield 74%) as a wax-like substance.
IRυ$_{max}^{neat}$ cm$^{-1}$: 3310, 1720, 1630
$^1$H-NMR (CDCl$_3$)δ:0.88 (6H, t, J=7.0 Hz), 1.07–1.57 (30H, m), 1.42 (9H, s), 1.49 (9H, s), 1.57–1.79 (4H, m), 1.95–3.16 (10H, m), 4.15 (1H, dd, J=6.8, Hz), 4.46 (1H, dd, J=3.2, 12.2 Hz), 4.60–4.71 (1H, m), 5.09–5.23 (1H, m), 7.0 (1H, d, J=7.0 Hz), 7.64 (2H, d, J=8.8 Hz), 7.80 (2H, d, J=8.8 Hz), 8.13 (1 H, bs)

EXAMPLE 53

4,( 6,7-bis (dodecanoyloxy)-4-thiaheptanoylamino)benzoyl)-glutamic acid

A solution of 4-(6,7-bis(dodecanoyloxy)-4-thiaheptanoylamino)benzoylglutamic acid di-t-butyl ester as obtained in Example 52 (94 mg) in trifluoroacetic acid (5 ml) was stirred at room temperature for 4 hours, followed by concentration, to yield the title compound (80 mg, yield 96%) as a colorless crystal.
IRυ$_{max}^{neat}$ cm$^{-1}$: 3300, 1740, 1710, 1640
$^1$H-NMR (CDCl$_3$+ 5% CD$_3$OD)δ:0.88 (6H, t, J=6.8 Hz), 1.03–1.50 (32H, m), 1.50–1.72 (4H, m), 2.03–2.62 (8H, m), 2.69 (2H, t, 7.4 Hz), 2.76 (2H, d, J=6.8 Hz), 2.95 (2H, t, J=7.4 Hz), 4.17 (1H, dd, J=6.4, 12.0 Hz), 4.42 (1H, dd, J=3.2, 12.0 Hz), 4.63–4.77 (1H, m), 5.10–5.26 (1H, m), 7.64 (2H, d, J=8.8 Hz 7.81 (2H, d, J=8.8 Hz)

EXAMPLE 54

(4-6,7-bis(palmitoyloxy)-3-methyl-4-thiaheptanoyl) aminobenzoyl)-glutamic acid di-t-butyl ester To a solution of 4-aminobenzoylglutamic acid di-t-butyl ester (378 mg) in pyridine (5 ml), phosphorus trichloride (0.044 ml) was added, followed by stirring at room temperature for 2 hours. To this mixture, 6,7-bis(palmitoyloxy)-

3-methyl-4-thiaheptanoic acid as obtained in Reference Example 29 (336 mg) was added, followed by stirring at room temperature for 24 hours. After addition of water, the reaction mixture was extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (hexane:ethyl acetate = 2:1) to yield the title compound (306 mg, yield 59%) as a wax-like substance.
IR$v_{max}^{neat}$ cm$^{-1}$: 3350, 1730
$^1$H-NMR (CDCl$_3$) 3:0.88 (6H, t, J=6.8 Hz), 1.03–1.53 (51H, m), 1.42 (9H, s), 1.49 (9H, s), 1.53–1.82 (4H, m), 1.94–3.50 (13H, m), 4.08–5.27 (4H, m), 6.93–7.20 (1H, m), 7.57–8.40 (6H, m)

EXAMPLE 55

(4-(6,7:bis(palmitoyloxy)-3-methyl-4-thiaheptanoyl) aminobenzoyl)-glutamic acid

A solution of (4-(6,7-bis(palmitoyloxy)-3-methyl-4-thiaheptanoyl)aminobenzoyl)glutamic acid di-t-butyl ester as obtained in Example 54 (306 mg) in trifluoroacetic acid (4 ml) was stirred at room temperature for 4 hours, followed by concentration, to yield the title compound (270 mg, yield 99%) as a colorless crystal.
IR$v_{max}^{neat}$ cm$^1$: 3350, 1735, 1640
$^1$H-NMR (CDCl$_3$)δ:0.88 (6H, t, J=6.8 Hz), 1.03–1.50 (48H, m), 1.39 (3H, t, J=6.8 Hz), 1.50–1.73 (4H, m), 2.03–2.88 (9H, m), 4.18 (1H, dd, J=6.2, 11.8 Hz), 4.32–4.45 (1H, m) 4.62–4.77 (1H, m), 5.05–5.23 (1H, m), 7.58–7.83 (4H, m)

EXAMPLE 56

4-(N-(2-((2R)-2,3-bis(palmitoyloxy)prolpylthio) ethylsulfonyl)-N-tbutyloxycarbonylaminomethyl) benzoyl-glutamic acid di-t-butyl ester To a solution of 4-(N-(2-((2R)-2,3-dihydroxypropylthio-)ethylsulfonyl)-N -t-butyloxycarbonylaminomethyl-)benzoyl-glutamic acid di-t-butyl ester as obtained in Reference Example 32 (75 mg), 4-dimethylaminopyridine (30 mg) and triethylamine (80 mg) in dichloromethane (0.5 ml), a solution of palmitoyl chloride (68 mg) in dichloromethane (0.5 ml) was added, followed by stirring under ice cooling conditions for 1 hour. To the reaction mixture, methanol (0.5 ml) was added, followed by stirring at room temperature for 30 minutes. After the mixture was concentrated to dryness under reduced pressure, the residue was purified by silica gel column chromatography (nhexane:ethyl acetate = 7:3) to yield the title compound (108 mg, yield 85.0%) as a colorless solid.
$^1$ H-NMR (CDCl$_3$) 3:0.880 (6H, t, J=7.0 Hz), 1.254 (48H, s), 1.420 (9H, s), 1.476 (9H, s), 1.493 (9H, s), 1.591 (4H, m), 1.90–2.12 (1H, m), 2.12–2.50 (7 H, m), 2.572 (2H, d, J=6.6 Hz), 2.902 (2H, t, J=7.8 Hz), 3.719 (2H, t, J=7.8 4.158 (1H, dd, J=5.8, 11.8 Hz), 4.341 (1H, dd, J=3.8, 11.8 Hz), 4.660 (1H, m), 4.873 (2H, s), 5.120 (1H, m), 7.039 (1H, d,J=7.6 Hz), 7.435 (2H, d, J=8.4 Hz 7.821 (2H, d, J=8.4 Hz)
IR (KBr)$v$: 3400, 2920, 2850, 1730, 1640, 1525, 1500, 1460, 1390, 1365, 1340, 1300, 1275, 1260, 1245, 1220, 1140 cm$^{-1}$

EXAMPLE 57

4-(N-(2-((2R)-2,3-bis(palmitoyloxy)propylthio) ethylsulfonyl)-aminomethyl)benzoyl-glutamic acid A solution of 4-(N-(2-((2R)-2,3-bis(palmitoyloxy)propylthio)-ethylsulfonyl)-N-t-butyloxycarbonylaminomethyl-)benzoyl -glutamic acid de-t-butyl ester as obtained in Example 56 (108 mg) in trifluoroacetic acid (1 ml) was stirred at room temperature for 1 hour, followed by concentration to dryness under reduced pressure, to yield the title compound (89 mg, yield 100%) as a colorless solid.
$^1$H-NMR (CDCl$_3$)δ: 0.877 (6H, t, J=7.0 Hz), 1.251 (48H, s), 1.597 (4H, m), 1.95–2.27 (2H, m), 2.27–2.40 (4H, m), 2.475 (2H, m), 2.727 (2H, d, J=6.6 Hz), 2.932 (2H, m), 3.287 (2H, m), 4.08–4.45 (4H, m), 4.630 (1H, m), 5.1.30 (1H, m), 6.079 (1H, bs), 7.260 (2H, d, J=7.8 Hz), 7.616 (3H, d, J=7.8 Hz)
IR (KBr)$v$: 3370, 2920, 2850, 1735, 1630, 1540, 1460, 1410, 1320, 1260, 1240, 1220, 1170, 1145 cm$^-$

EXAMPLE 58

4-[6,7-bis(12–1phenyldodecanoyloxy)-4-thiaheptanoylaminomethyl] benzoyl-glutamic acid di-t-butyl ester A solution of 6,7-bis(12-phenyldodecanoyloxy)-4-thiaheptanoic acid as obtained in Reference Example 34 (200 mg), 4-(aminomethyl)benzoylglutamic acid di-t-butyl ester hydrochloride as obtained in Reference Example 37 (136 mg), DEPC (71 mg) and triethylamine (120 mg) in dimethylformarnide (6 ml) was stirred at room temperature for 1 hour. After solvent concentration, the resulting residue was purified by silica gel column (n-hexane:ethyl acetate = 2:1 to 1:3) to yield the title compound (260 mg, yield 85%) as a colorless syrup.
IR (Neat)$v$: 3300, 2920, 2850, 1730, 1650, 1630, 1540, 1490, 1450, 1360, 1245, 1150 cm$^{-1}$
$^1$H-NMR (CDCl$_3$)δ:1.26 (28H, s), 1.42 (9H, s), 1.49 (9H, s), 1.50–1.70 (8H, m), 1.90–2.65 (14H, m), 2.72 (2H, t, J=6.6 Hz), 2.92 (2H, t, J=6.0 Hz), 4.13 ( 1H, dd, J=12.0, 6.4 Hz), 4.38 (1H, dd, J=12.0, 3.2 Hz), 4.50 (2H, d, J=5.8 Hz), 4.66 (1H, m), 5.15 (1H, m), 6.27 (1H, t, J=5.8 Hz), 7.03 (1H, d, J=7.2 Hz), 7.10–7.40 (12H, m), 7.79 (2H, d, J=8.4 Hz)

EXAMPLE 59

4-[6,7-bis(12-phenyldodecanoyloxy)-4-thiaheptanoylaminomethyl] benzoyl-glutamic acid A solution of 4-[6,7-bis( 12-phenyldodecanoyloxy)-4-thiaheptanoylaminomethyl] benzoyl-glutamic acid di-t-butyl ester as obtained in Example 58 (255 mg) in trifluoroacetic acid (2 ml) was stirred at room temperature for 2 hours, after which the solvent was distilled off under reduced pressure, to yield the title compound (200 mg, yield 88%) as a syrup.
IR (Neat)$v$: 3300, 2920, 2850, 1730, 1715, 1630, 1535, 1500, 1490, 1450, 1410, 1240, 1160 cm$^{-1}$
$^1$H-NMR (CDCl$_3$)δ: 1.25 (28H, s), 1.50–1.70 (SH, m), 1.90–2.60 (10H, m), 2.58 (4H, t, J=8.0 Hz), 2.69 (2H, d, J=6.2 Hz), 2.75–2.90 (2H, m), 4.11 (1H, dd J=12.0, 6.2 Hz), 4.20–4.40 (3H, m), 4.62 (1H, m), 5.12 (1H, m), 7.00–7.30 (13H, m), 7.59 (2H, d, J=7.8 Hz), 7.75–7.90 (1H, m)

EXAMPLE 60

4-[6,7-bis(12-phenyldodecanoyloxy)-4-thiaheptanoylamino]benzoylglutamic acid di-t-butylester To a solution of 6,7-bis(12-phenyldodecanoyloxy)-4-thiaheptanoic acid as obtained in Reference Example 34 (200 mg) and 4-aminobenzoyl-glutamic acid di-t-butyl ester (108 mg) in pyridine (6 ml), phosphorus trichloride (4 drops) was added drop by drop, followed by stirring at room temperature for 1 hour. After the solvent was concentrated, the residue was purified by silica gel column (n-hexane:ethyl acetate=2:1) to yield the title compound (282 mg, yield 93%) as a colorless oily substance.
IR (Neat)$\upsilon$: 3300, 2920, 2850, 1730, 1700, 1630, 1590, 1520, 1500, 1490, 1360, 250, 1150 cm$^{-1}$
$^1$H-NMR (CDCl$_3$)$\delta$:1.26 (28H, s), 1.42 (9H, s), 1.49 (9H, s), 1.50–1.70 (8H, m), 1.90–2.50 (8H, m), 2.50–3.10 (10H, m), 4.15 (1H, dd, J=12.0, 6.6 Hz), 4.46 (1H, dd, J=12.0, 3.2 Hz), 4.65 (1H, m), 5.17 (1H, m), 6.98 (1H, d, J=7.2 Hz), 7.10–7.35 (10H, m), 7.64 (2H, d, J=8.8 Hz), 7.80 (2H, d, J=8.8 Hz), 8.07 (1H, s)

EXAMPLE 61

4-[6,7-bis(12-phenyldodecanoyloxy)-4-thiaheptanoylamino]benzoylglutamic acid A solution of 4-[6,7-bis(12-phenyldodecanoyloxy)-4-thiaheptanoylamino] benzoyl-glutamic acid di-t-butyl ester as obtained in Example 60 (275 mg) in trifluoroacetic acid (2 ml) was stirred at room temperature for 2 hours, after which the solvent was distilled off under reduced pressure, to yield the title compound (207 mg, yield 84%) as a syrup.
IR (Neat)$\upsilon$: 3300, 2920, 2850, 1730, 1710, 1630, 1600, 1520, 1500, 1490, 1450, 1400, 1305, 1250, 1175 cm$^{-1}$
1H-NMR (CDCl$_3$)$\delta$:1.24 (28H, s), 1.50–1.70 (8H, m), 1.90–2.80 (12H, m), 2.57 (4H, t, J=8.0 Hz), 2.80–3.00 (2H, m), 4.14 (1H, dd, J=12.0, 6.2 Hz), 4.39 (1H, dd, J=12.0, 2.4 Hz), 4.62 (1H, m), 5.16 (1H, m), 7.10–7.30 (10H, m), 7.43 (2H, d, J=8.2 Hz), 7.60 (2H, d, J=8.2 Hz), 7.70–7.85 (1H, m), 8.88 (1H, s)

EXAMPLE 62

5-(6,7-bis(palmitoyloxy)-4-thiaheptanoyl) amino-2-(1,3-bis-(t-butyloxycarbonyl)propyl) isoindolin- 1-one To a solution of 5-amino-2-(1,3-bis-(t-butyloxycarbonyl) propyl)isoindolin- 1-one (178 mg) in pyridine (2.3 ml), phosphorus trichloride (0.020 ml) was added, followed by stirring at room temperature for 2 hours. To this mixture, 6,7-bis(palmitoyloxy)-4-thiaheptanoic acid (150 mg) was added, followed by stirring at room temperature for 24 hours. After addition of water, the reaction mixture was extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (hexane:ethyl acetate = 2:1) to yield the title compound (208 mg, yield 91%) as a wax-like substance.
IR$\upsilon_{max}^{KBr}$ cm$^{-1}$: 1730
$^1$H-NMR (CDCl$_3$)$\delta$: 0.88 (6H, t, J=6.8 Hz), 1.03–1.48 (48H, m), 1.40 (9H, s), 1.44 (9H, s), 1.48–1.82 (4H, m), 2.04–3.14 (10H, m), 2.33 (2H, t, J=7.8 Hz), 2.36 (2H, t, J=7.2 Hz), 4.15 (1H, dd, J=6.8, 12.0 Hz), 4.35 (1H, d, J=16.8 Hz), 4.49 (1H, dd, J=3.2, 12.0 Hz), 4.63 (1H, d, J=16.8 Hz), 4.96 (1H, dd, J=4.6, 10.6 Hz), 5.10–5.26 (1H, m), 7.33 (1H, dd, J=1.8, 8.2 Hz), 7.78 (1H, d, J=8.2 Hz), 8.09 (1H, d, J=1.8 Hz), 8.23 (1H, bs)

EXAMPLE 63

5-(6,7-bis(palmitoyloxy)-4-thiaheptanoyl)amino-2-(1,3-bis(hydroxycarbonyl)propyl)isoindolin- 1-one A solution of 5-(6,7-bis(palmitoyloxy)-4-thiaheptanoyl)amino-2-(1,3 -bis(t-butyloxycarbonyl)propyl)isoindolin-1-one as obtained in Example 62 (208 mg) in trifluoroacetic acid (5 ml) was stirred at room temperature for 4 hours, followed by concentration, to yield the title compound (191 mg, yield 100%) as a colorless crystal.
IR$\upsilon_{max}^{KBr}$ cm$^{-1}$: 3450 1750, 1670, 1620
$^1$H-NMR(CDCl$_3$+5% CD$_3$OD)$\delta$: 0.88 (6H, t, J=6.8 Hz), 1.08–1.53 (48H, m), 2.07–3.09 (14H, m), 4.01–5.30 (5H, m), 7.37 (1H, d, J=8.4 Hz), 7.77 (1H, d, J=8.4 Hz), 8.12 (1H, s)

EXAMPLE 64

4-( 6,7-bis(palmi toyloxy )-4-thiaheptanoyl)amino-N-(1,3-bis-(t-butyloxycarbonyl)propyl)phthalimide To a solution of 4-amino-N-(1,3-bis-(t-butyloxycarbonyl) propyl)phthalimide (178 mg) in pyridine (2.3 ml), phosphorus trichloride (0.020 ml) was added, followed by stirring at room temperature for 2 hours. To this mixture, 6,7-bis(palmitoyloxy)-4-thiaheptanoic acid as obtained in Reference Example 24 (150 mg) was added, followed by stirring at room temperature for 24 hours. After addition of water, the reaction mixture was extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (hexane:acetone=3:1) to yield the title compound (190 mg, yield 80%) as a wax-like substance.
IR$\upsilon_{max}^{KBr}$ cm$^{-1}$: 1730
$^1$H-NMR (CDCl$_3$)$\delta$: 0.88 (6H, t, J=6.6 Hz), 1.02–1.45 (48H, m), 1.41 (9H, s), 1.42 (9H, s), 1.45–1.75 (4H, m), 2.16–3.14 (14H, m), 4.13 (1H, dd, J=7.0, 12 Hz), 4.52 (1H, dd, J=2.8, 12.2 Hz), 4.79 (1H, rid, J=5.0, 9.6 Hz), 5.10–5.26(1H, m), 7.79 (1H, d, J=8.2 Hz), 7.99 (1H, dd, J= 1.6, 8.2 Hz), 8.08 (1H, d, J=1.6 Hz), 8.53 (1H, bs)

EXAMPLE 65

4-(6,7-bis(palmitoyloxy)-4-thiaheptanoyl)amino-N-(1,3 -bis(hydroxycarbonyl)propyl)phthalimide A solution of 4-(6,7-bis(palmitoyloxy)-4-thiaheptanoyl)amino-N-(1,3-bis(t-butyloxycarbonyl)propyl)phthalimide as obtained in Example 64 (191 mg) in trifluoroacetic acid (5 ml) was stirred at room temperature for 4 hours, followed by concentration, to yield the title compound (170 mg, yield 100%) as a colorless crystal.
IR$\upsilon_{max}^{KBr}$ cm$^{-1}$: 3450, 1730, 1610
$^1$H-NMR (CDCl$_3$+5% CD$_3$OD) 3:0.88 (6H, t, J=6.8 Hz), 1.02–1.50 (48H, m), 1.50–1.75 (4H, m), 2.04–3.06 (14H, m), 4.00–4.49 (2H, m), 4.80–4.95 (1H, m), 5.10–5.25 (1H, m), 7.74–8.11 (3H, m)

EXAMPLE 66

4-[6,7-bis(nalmitoyloxy)-4-thiaheptanoylamino] benzoyl-glutamic acid di-t-butyl ester 4:oxide (A) and 4-[6,7-bis(palmitoyloxy)-4-thiaheptanoyl-amino] benzoyl-glutamic acid di-t-butyl ester 4,4-dioxide (B)

To a solution of 4-[6,7-bis(palmitoyloxy)-4-thiaheptanoylamino] benzoyl-glutamic acid di-t-butyl ester as obtained in Example 17 (230 mg) in chloroform (6 ml), a solution of m-chloroperbenzoic acid (67 mg) in chloroform (2 ml) was added drop by drop under ice cooling conditions, followed by stirring for 2 hours. The reaction mixture was diluted with chloroform, washed with a saturated aqueous solution of sodium hydrogen carbonate and water, and dried, after which the solvent was concentrated. The resulting residue was purified by silica gel column chromatography (n-hexane:ethyl acetate=1:1 to 1:5) to yield the title compound (A) (116 mg, yield 50%) as a colorless amorphous substance and the title compound (B) (119 mg, yield 50%) as a colorless amorphous substances.

Compound (A)
IR (Neat)$\upsilon$: 2920, 2850, 1730, 1650, 1595, 1530, 1495, 1360, 1250, 1150 cm$^{-1}$
$^1$H-NMR (CDCl$_3$)$\delta$: 0.88 (6H, t, J=6.8 Hz), 1.25 (48H, s), 1.42 (9H, s), 1.49 (9H, s), 1.50–1.70 (4H, m), 1.90–2.50 (8H, m), 2.90–3.40 (6H, m), 4.10–4.30 (1H, m), 4.35–4.50 (1H, m), 4.60–4.75 (1H, m), 5.50 (1H, m), 7.01 (1H, d, J=7.2 Hz), 7.62 (2H, d, J=8.8 Hz), 7.79 (2H, d, J=8.8 Hz), 8.88 (½×1H, brs), 8.94 (½×1H, brs)

Compound (B)
IR (Neat)$\upsilon$: 3330, 2920, 2850, 1730, 1695, 1640, 1595, 1530, 1495, 1460, 1365, 1310, 1250, 1150, 905,730 cm$^{-1}$
$^1$H-NMR (CDCl$_3$)$\delta$: 0.88 (6H, t, J=6.8 Hz), 1.25 (48H, s), 1.42 (9H, s), 1.49 (9H, s), 1.50–1.70 (4H, m), 2.00–2.50 (8H, m), 2.95 (2H, t, J=7.0 Hz), 3.33 (1H, dd, J=14.8, 4.8 Hz), 3.46 (1H, dd, J=14.8, 7.2 Hz), 3.53 (2H, t, J=7.0 Hz), 4.19 (1H, dd, J=12.0, 5.2 Hz), 4.43 (1H, J=12.0, 3.8 Hz), 4.65 (1H, m), 5.58 (1H, m), 7.05 (1H, d, J=7.8 Hz), 7.57 (2H, d, J=8.8 Hz), 7.78 (2H, d, J=8.8 Hz), 8.23 (1H, brs)

EXAMPLE 67

4-[6,7-bis(palmitoyloxy)-4-thiaheptanoylmino] benzoyl-glutamic acid 4-oxide

A solution of 4-[6,7-bis(palmitoyloxy)-4-thiaheptanoylamino]benzoylglutamic acid di-t-butyl ester 4-oxide as obtained in Example 66 (115 mg) in trifiuoroacetic acid (3 ml) was stirred at room temperature for 2 hours. After the solvent was distilled off under reduced pressure, the resulting residue was crystallized from methanol-water to yield the title compound (165 mg, yield 94%) as a colorless crystal.
IR (KBr) $\upsilon$: 2919, 2852, 1737, 1639, 1531, 1307, 1253, 1178 cm$^{-1}$ $^1$H-NMR (CDCl$_3$-CDSOD-trifiuoroacetic acid) 3:0.88 (6H, t, J=6.6 Hz), 1.25 (48H, s), 1.50–1.70 (4H, m), 2.00–2.40 (8H, m), 2.80–3.40 (6H, m), 4.10–4.30 (1H, m), 4.35–4.80 (2H, m), 5.49 (1H, m), 7.50–7.80 (4H, m)

EXAMPLE 68

4-[6,7-bis(palmitoyloxy)-4-thiaheptanoylamino] benzoyl-glutamic acid 4,4-dioxide A solution of 4-[6,7-bis(palmitoyloxy)-4-thiaheptanoylamino]benzoylglutamic acid di-t-butyl ester 4,4-dioxide as obtained in Example 66 (115 mg) in trifiuoroacetic acid (3 ml) was stirred at room temperature for 2 hours. After the solvent was distilled off under reduced pressure, the resulting residue was crystallized from methanol-water to yield the title compound (165 mg, yield 94%) as a colorless crystal.
IR (KBr)$\upsilon$: 3336, 2919, 2850, 1741, 1641, 1604, 1533, 1463, 1407, 1311, 1255, 1178 cm$^{31\ 1}$
$^1$H-NMR (CDCl$_3$–CD$_3$OD)$\delta$:0.88 (6H, t, J=6.6 Hz), 1.25 (48H, s), 1.50–1.70 (4H, m), 1.90–2.60 (8H, m), 2.92 (2H, t, J=7.0 Hz), 3.35–3.60 (4H, m), 4.18 (1H, dd, J=12.0, 5.0 Hz), 4.42 (1H, dd, J=12.0, 3.2 Hz), 4.69 (1H, m), 5.60 (1H, m), 7.50 (2H, d, J=8.8 Hz), 7.67 (2H, d, J=8.8 Hz)

EXAMPLE 69

(2R,6R) 4-[2-acetoxy-6,7-bis(palmitoyloxy)-4-thiaheptanoylaminomethyl] benzoyl-glutamic acid di-t-butyl ester To a solution of (2R,6R) 4-[2-amino-6,7-bis(palmitoyloxy)-4thiaheptanoylaminomethyl] benzoyl-glutamic acid di-t-butyl ester as obtained in Reference Example 39 (243 mg) in acetic acid (6 ml), an aqueous solution of sodium nitrite (13 mg) (0.3 ml) was added, followed by stirring at room temperature overnight. The solvent was concentrated under reduced pressure; the resulting residue was purified by silica gel column chromatography (n-hexane:ethyl acetate= 2:1 to 1:1) to yield the title compound (94 mg, yield 54%) as a colorless wax-like substance. IR (Neat)$\upsilon$: 3300, 2920, 2850, 1730, 1640, 1530, 1500, 1460, 1450, 1360, 1240, 1220, 1150 cm$^{-1}$
$^1$H-NMR (CDCl$_3$)$\delta$: 0.88 (6H, t, J=7.0 Hz), 1.26 (48H, s), 1.42 (9H, s), 1.49 (9H, s), 1.50–1.70 (4H, m), 1.90–2.50 (8H, m), 2.16 (3H, s), 2.70–2.90 (2H, m), 2.95–3.25 (2H, m), 4.00–4.70 (5H, m), 5.18 (1H, m), 5.39 (1H, m), 6.80–6.95 (1H, m), 7.07 (1H, d, J=7.4Hz), 7.35 (2H, d, J=8.0 Hz), 7.79 (2H, d, J= 8.0 Hz)

EXAMPLE 70

(2R,6R) 4-[2-acetoxy-6,7-bis(palmitoyloxy)-4-thiaheptanoylaminomethyl] benzoyl]glutamic acid A solution of (2R,6R) 4-[2-acetoxy-6,7-bis(palmitoyloxy)-4thiaheptanoylaminomethyl] benzoyl-glutamic acid di-t-butyl ester as obtained in Example 69 (92 mg) in trifiuoroacetic acid (2 ml) was stirred at room temperature for 1 hour. After the solvent was distilled off under reduced pressure, the resulting residue was crystallized from methanol-water to yield the title compound (65 mg, yield 79%) as a colorless crystal.
IR (KBr)$\upsilon$: 3344, 2920, 2850, 1727, 1647, 1540, 1226, 1176 cm$^{-1}$
$^1$H-NMR (CDCl$_3$)$\delta$:0.88 (6H, t, J=6.8 Hz), 1.25 (48H, s), 1.50–1.70 (4H, m), 2.00–2.35 (6H, m), 2.15 (3H, s), 2.40–2.55 (2H, m), 2.70–2.80 (2H, m), 2.95– 3.15 (2H, m), 4.00–4.70 (5H, m), 5.18 (1H, m), 5.37 (1H, m), 7.24 (2H, d, J=8.2 Hz), 7.50–7.80 (2H, m), 7.67 (2H, d, J=8.2 Hz)

EXAMPLE 71

(4-(6,7-bis(palmitoyloxy)-2-methyl-4-thiaheptanoyl)amino-benzoyl)glutamic acid di-t-butyl ester To a solution of 4-aminobenzoylglutamic acid di-t-butyl ester (378 mg) in pyridine (5 ml), phosphorus trichloride (0.044 ml) was added, followed by stirring at room temperature for 2 hours. To this solution, 6,7-bis(palmitoyloxy)-2-methyl-4-thiaheptanoic acid as obtained in Reference Example 42 (336 mg) was added, followed by stirring at room temperature for 24 hours. After addition of water, the reaction mixture was extracted with ethyl acetate. The extract was washed with a 5% aqueous solution of citric acid, a saturated aqueous solution of sodium hydrogen carbonate and saturated saline, and dried over anhydrous sodium sulfate, and the solvent was distilled off. The resulting residue was purified by silica gel column chromatography (hexane:ethyl acetate = 2:1) to yield the title compound (315 mg, yield 62%) as a wax-like substance.
IR$\upsilon_{max}^{KBr}$ cm$^{-1}$: 1750
$^1$H-NMR (CDCl$_3$)δ:0.88 (6H, t, J=6.8 Hz), 1.03–1.53 (51H, m), 1.42 (9H, s), 1.49 (9H, s), 1.53–1.82 (4H, m), 1.95–3.22 (13H, m), 4.00–5.30 (4H, m), 6.94– 7.03 (1H, m), 7.64–8.53 (5H, m)

EXAMPLE 72

(4-(6,7-bis(palmitoyloxy)-2=methyl-4-thiaheptanoyl) aminobenzoyl)glutamic acid

To a solution of (4-(6,7-bis(palmitoyloxy)-2-methyl-4-thiaheptanoyl)aminobenzoyl)glutamic acid di-t-butyl ester as obtained in Example 71 (315 mg) in trifluoroacetic acid (4 ml) was stirred at room temperature for 4 hours. The mixture was concentrated to yield the title compound (280 mg, yield 100%) as a colorless crystal.
IR$\upsilon_{max}^{KBr}$ cm$^-$: 3350, 1750, 1640 1H-NMR (CDCl$_3$)δ:0.88 (6H, t, J=6.8 Hz), 1.03–1.50 (51H, m), 1.50–1.70 ( 4H, m), 2.02–3.15 (13H, m), 4.06–5.26 (4H, m), 7.57–7.90 (4H, m)

EXAMPLE 73

6,7-bis(palmitoyloxy),4-thiaoctanoyl-glutamic acid di-t-butyl ester

A solution of 6,7-dihydroxy-4-thiaoctanoic acid as obtained in Reference Example 45 (168 mg), glutamic acid di-t-butyl ester hydrochloride (256 mg), DEPC (197 mg) and triethylamine (300 μl) in dimethylformamide (2.0 ml) was stirred at room temperature for 1 day. To the mixture, ethyl acetate was added, and the mixture was washed with a saturated saline, a 10% aqueous solution of citric acid and saturated aqueous sodium bicarbonate, after which the organic layer was concentrated under reduced pressure. The residue was dissolved in methylene chloride. To this solution, palmitoyl chloride (484 mg) and dimethylaminopyridine (401 mg) were added, followed by stirring at room temperature for 1 day. To the reaction mixture, ethyl acetate was added, and the reaction mixture was washed with saturated saline, after which the organic layer was concentrated under reduced pressure. The resulting residue was purified by silica gel column chromatography (methylene chloride:acetone=50:1) to yield the title compound (291 mg, yield 55%) as a colorless oily substance.
IR (Neat)υ: 3400, 2975, 2925, 1720, 1670, 1600, 1540, 1500, 1420, 1360, 1150, 890,750,700 cm$^1$
$^1$H-NMR (CDCl$_3$)δ:6.35 (1H, m), 5.15 (1H, m), 5.05 (1H, m), 2.94–2.79 (2 H, m), 2.72–2.64 (2H, m), 2.54–2.43 (2H, m), 2.40–2.24 (6H, m), 2.18 (1H, s), 2.10 (1H, s), 1.94 (1H, m), 1.64 (4H, m), 1.47 (9H, s), 1.45 (9H, s), 1.26 (48H, s 1.22 (3H, d, J=6.6 Hz), 0.88 (6H, t, J=6.6 Hz)

EXAMPLE 74

6,7-bis(palmitoyl0xy)-4-thiaoctanoyl-glutamic acid

A solution of 6,7-bis(palmitoyloxy)-4-thiaoctanoyl-glutamic acid di-tbutyl ester as obtained in Example 73 (280 mg) in methylene chloride (4 ml)trifluoroacetic acid (5 ml) was stirred at room temperature for 4 hours, after which the solvent was distilled off under reduced pressure, to yield the title compound (223 mg, yield 91%) as a light yellow powder.
IR (Neat)υ: 3320, 2918, 2850, 1736, 1653, 1549, 1468, 1417, 1383, 1265, 1246, 1223, 1120, 1178, 1116, 722 cm$^{-1}$
$^1$H-NMR (CDCl$_3$)δ:5.18 (1H, m), 5.05 (1H, m), 4.57 (1H, m), 2.83 (2H, m), 2.68 (2H, t, J=7.6 Hz), 2.52–2.18 (10H, m), 2.02 (1H, m), 1.60 (4H, m), 1.26 (51H, s), 0.88 (6H, t, J=6.6 Hz)

EXAMPLE 75

4-[6,7,bis(palmitoyloxy)-4-thiaoctanoylaminomethyl] benzoyl-glutamic acid di-t-butyl ester A solution of 6,7-dihydroxy-4-thiaoctanoic acid as obtained in Reference Example 45 (151 mg), 4-(aminomethyl)benzoyl-glutamic acid di-t-butyl ester hydrochloride as obtained in Reference Example 37 (506 mg), DEPC (201 mg) and triethylamine (300 ill) in dimethylformamide (2.0 ml) was stirred at room temperature for 1 day. To the mixture, ethyl acetate was added, and the mixture was washed with a saturated saline, a 10% aqueous solution of citric acid and saturated aqueous sodium bicarbonate, after which the organic layer was concentrated under reduced pressure. The residue was dissolved in methylene chloride. To this solution, palmitoyl chloride (487 mg) and dimethylaminopyridine (413 mg) were added, followed by stirring at room temperature for 1 day. To the reaction mixture, ethyl acetate was added, and the reaction mixture was washed with saturated saline, after which the organic layer was concentrated under reduced pressure. The resulting residue was purified by silica gel column chromatography (hexane::ethyl acetate = 1.5:1) to yield the title compound (584 mg, yield 72%) as a colorless solid.
IR (Neat)υ: 3300, 3050, 2925, 2850, 1730, 1650, 1540, 1500, 1460, 1360, 1260, 1150, 840,740,700 cm$^{-1}$ $^1$H-NMR (CDCl$_3$)δ: 7.79 (2H, d, J=8.2 Hz), 7.36 (2H, d, J=8.2 Hz), 7.03 (0.5H, d, J=3.4 Hz), 6.99 (0.5H, d, J=3.2 Hz), 6.45 (0.5H, m), 6.25 (0.5H, m), 5.18 (1.5 H, m), 5.00 (0.5H, m), 4.45 (2H, d, J=6.0 Hz), 3.00–2.84 (2H, m), 2.71–2.63 (2H, m), 2.58–2.49 (2H, m), 2.44–2.17 (7H, m), 2.10–1.98 (2H, m), 1.64 (4H, m), 1.49 (9H, s), 1.42 (9H, s), 1.26 (48H, s), 1.18 (3H, d, J=6.4 Hz), 0.88 ( 6H, t J=6.2 Hz)

EXAMPLE 76

4-[6,7-bis(palmitoyloxy)-4-thiaoctanoylarninomethyl] benzoyl-glutamic acid

A solution of 4-[6,7-bis(palmitoyloxy)-4-thiaoctanoylaminomethyl] benzoyl-glutamic acid di-t-butyl ester as obtained in Example 75 (574 mg) in methylene chloride (4 ml)-trifiuoroacetic acid (5 ml) was stirred at room temperature for 4 hours, after which the solvent was distilled off under reduced pressure. The residue was recrystallized from methanolwater to yield the title compound (505 mg, yield 99%) as a colorless powder.

IR (Neat)υ: 3320, 2914, 2848, 1734, 1637, 1543, 1506, 1468, 1416, 1381, 1265, 1245, 1222, 1198, 1178, 1101, 754, 721 cm$^{-1}$ $^1$H-NMR (CDCl$_3$) 3:7.78 (2H, d, J=8.0 Hz), 7.57 (0.5H, d, J=6.6 Hz), 7.36 (2H, d, J=8.0 Hz), 7.14 (0.5H, m), 5.18 (1H, m), 4.72 (1H, m), 4.47 (2H, d J=5.4 Hz), 2.92–2.79 (2H, m), 2.69 (2H, m), 2.60–2.46 (2H, m), 2.41–2.05 m), 1.61 (4H, m), 1.25 (48H, s), 1.18 (3H, d), 0.88 (6H, t, J=6.2 Hz)

EXAMPLE 77

4-[6,7-bis(12-cyclohexyldodecanoyloxy),4-thiaheptanoylamino)benzoylglutamic acid di-t-butyl ester 6,7-bis( 12-cyclohexyldodecanoyloxy)-4-thiaheptanoic acid ( 166 mg, 0.234 mM) as obtained in Reference Example 47 and 4-aminobenzoylglutamic acid di-t-butyl ester were dissolved in pyridine (2.0 ml). To the mixture, phosphorous trichloride (35 mg, 0.258 mM) was added under ice cooling conditions. The reaction mixture was stirred under ice cooling conditions for 30 minutes and then at room temperature for 1 hour, and then concentrated to dryness under reduced pressure. To the resulting residue, chloroform (20 ml), water ( 15 ml) and saturated saline (5 ml) were added, followed by vigorous stirring, after which the chloroform layer was separated. The chloroform layer was dried over anhydrous sodium sulfate and concentrated to dryness under reduced pressure. The resulting residue was purified by silica gel colum (5 g) (n-hexane-chloroform (1:4)) and then silica gel colum (5 g) (ethyl acetate-chloroform (1:4)) to yield the title compound (67 mg, yield 26.8%) as a colorless solid.

IR(neat)υ; 3300, 2920, 2850, 1730, 1635, 1590, 1520, 1495, 1440, 1360, 1300, 250, 1150 cm$^{-1}$
$^1$H-NMR(CDCl$_3$) 3; 0.866(4H,m), 1.175(4H,m), 1.250(42H,s), 1.422(9H,s), 1.491(9H,s), 1.675(16H,m), 1.90–2.50(SH,m), 2.60–2.80(4H,m), 2.80–3.10(2H,m), 4.155(1H,dd,J=7.2 Hz, 11.6 Hz), 4.468(1H,dd,J=3.0 Hz, 11.6 Hz), 4.527(1H,m), 5.660(1H,m), 6.991(1H,d, J=7.6 Hz), 7.651(2H,d,J=8.8 Hz), 7.809(2H,d,J=8.8 Hz), 8.104(1H,s)

EXAMPLE 78

4-[ 6,7-bis(12-cyclohexyldodecanoyloxy)-4thiaheptanoylamino)benzoylglutamic acid 4-[6,7-bis(12-cyclohexyldodecanoyloxy)-4thiaheptanoylamino)benzoylglutamic acid di-t-butyl ester (67 mg, 0.063 mM) as obtained in Example 77 was dissolved in trifiuoroacetic acid (0.7 ml), followed by stirring at room temperature for 1 hour. The reaction mixture was concentrated to dryness under reduced pressure. To the resulting residue, toluene (1 ml) was added and the mixture was concentrated to dryness under reduced pressure. This operation was repeated again and the resulting residue was dissolved in dichloromethane ( 1 ml) and then concentrated to dryness under reduced pressure to yield the title compound (61 mg, yield 100%) as a colorless solid.

IR(neat)υ; 3320, 2920, 2850, 1730, 1640, 1600, 1535, 1500, 1440, 1400, 1305, 1250, 1170 cm$^{-1}$
$^1$H-NMR(CDCl$_3$)δ; 0.859(4H,m), 1.172(4H,m), 1.244(42H, s), 1.635(16H,m), 1.90–2.20(2H,m), 2.312(2H,t,J=6.8 Hz), 2.330(2H,t,J =6.SHz), 2.440(2H,bs), 2.704(4H,m), 2.891(2H,bs), 4.156(1H,dd,J =6.4 Hz,12.4 Hz), 4.413(1H, dd,J=2.2 Hz, 12.4 Hz), 4.635(1H,m), 5.169(1H,m), 7.444(2H,d,J=9.2 Hz), 7.608(2H,d,J=9.2 Hz), 7.750(1H,m), 8.882(1H,s)

EXAMPLE 79

4-[6,7:bis(12-cyclohexyl dodecanoyloxy)4-thiaheptanoylaminomethyl) benzoylglutamic acid di-t-butyl ester 6,7-bis(12-cyclohexyldodecanoyloxy)-4-thiaheptanoic acid (166 mg, 0.234 mM) as obtained in Reference Example 47 and 4(aminomethyl)benzoylglutamic acid di-t-butyl ester (110 mg, 0.80 mM) as obtained in Reference Example 37 were dissolved in dimethylformamide (2.3 ml). To the mixture, diethyl cyanophosphate (48 mg, 0.29 mM) and triethylamine (80 mg, 0.8 mM) were added under ice cooling conditions. The reaction mixture was stirred under ice cooling conditions for 1 hour, and then concentrated to dryness under reduced pressure. The resulting residue was washed with water (5 ml) and the supernatant was decanted. The residue was purified by silica gel colum (5 g) (n-hexane-chloroform (1:4)) and then silica gel colum (5 g) (chloroform) to yield the title compound (244 mg, yield 96.3%) as a colorless solid.

IR(neat)υ; 3300, 2920, 2850, 1730, 1640, 1535, 1500, 1440, 1360, 1250, 1150 cm$^{-1}$
$^1$H-NMR(CDCl$_3$) 3; 0.870(4H,m), 1.175(4H,m), 1.249(42H,s), 1.442(9H,s), 1.492(9H,s), 1.659(16H,m), 1.90–2.45(8H,m), 2.550(2H,t,J=6.8 Hz), 2.719(2H,d,J=6.6 Hz), 2.928(2H,t,J=8.2 Hz), 2.928(2H,d,J=16 Hz), 4.134(1H, dd,J=6.4 Hz, 12.0 Hz), 4.389(1H,dd,J=3.0 Hz,12.0 Hz), 4.512(2H,d,J=6.0 Hz), 4.664(1H,m), 5.142(1H,m), 6.249(1H,t,J=7.5 Hz), 7.027( 1H,d,J=8.2 Hz), 7.361(2H,d, J=8.4 Hz), 7.794( 2H,d,J=8.4 Hz)

EXAMPLE 80

4-[6,7-bis (12-cyclohexyldodecanoyloxy)-4thiaheptanoylaminomethyl)benzoylglutamic acid 4-[6,7-bis( 12-cyclohexyldodecanoyloxy)-4thiaheptanoy- laminomethyl)benzoylglutamic acid di-t-butyl ester (111 mg, 0.09 mM) as obtained in Reference Example 79 was dissolved in trifiuoroacetic acid (1 ml), followed by stirring at room temperature for 1 hour. The reaction mixture was concentrated to dryness under reduced pressure. To the resulting residue, toluene (1 ml) was added and the mixture was concentrated to dryness under reduced pressure. This operation was repeated again and the resulting residue was dissolved in dichloromethane (1 ml) and then concentrated to dryness under reduced pressure to yield the title compound (182 mg, yield 100%) as a colorless solid.

IR(neat)υ; 3300, 3070, 2920, 2850, 1730, 1630, 1540, 1500, 1460, 1440, 1410, 1340, 1250, 1200, 1160 cm$^{-1}$
$^1$H-NMR(CDCl$_3$)δ; 0.865(4H,m), 1.147(4H,m), 1.246(44H, s), 1.656(14H,m), 1.90–2.20(2H,m), 2.271(4H,dt,J=7.0 Hz,0.8 Hz), 2.436(2H,bs), 2.583(2H,t,J=6.6 Hz), 2.704(2H, d,J=7.0 Hz), 2.870(2H,t,J=6.4 Hz), 4.119(1H,dd,J=5.8 Hz, 12.0 Hz), 4.365( 3H,d,J = 8.6 Hz), 4.636(1H,m), 5.144(1H ,m ), 7.165(2H,d,J=7.6 Hz), 7.426( 1H,bs ), 7.604( 2H,d,J= 7.6 Hz 7.840(1H,d,J=6.8 Hz)

EXAMPLE 81

4-[6,7-bis(11,cyclohexylundecylcarbamoyloxy)-4-thiaheptanoylamino] benzoylglutamic acid di-t-butyl ester 6,7-bis(11-cyclohexylundecylcarbamoyloxy)-4-thiaheptanoic acid (188 mg, 0.25 mM) as obtained in Reference Example 51 and 4aminobenzoylglutamic acid di-t-butyl ester (118 mg, 0.31 mM) were dissolved in pyridine (2.0 ml). To the mixture, phosphorous trichloride (43 mg, 0.31 raM) was added under ice cooling conditions. The reaction mixture was stirred under ice cooling conditions for 30 minutes and then at room temperature for 1 hour, and then concentrated to dryness under reduced pressure. The resulting residue was purified by silica gel colum (7 g) (ethyl acetate-n-hexane (2:3)) to yield the title compound (70 mg, yield 27%) as a colorless solid.

IR(neat) υ; 3320, 2920, 2850, 1730, 1700, 1640, 1600, 1530, 1500, 1440, 1365, 1250, 1150 cm$^{-1}$
$^1$H-NMR(CDCl$_3$)δ; 0.857(4H,m), 1.176(4H,m), 1.250(42H,s), 1.422(9H,s), 1.453(4H,m), 1.491(9H,s), 1.600(12H,m), 1.90–2.52(4H,m), 2.52–3.10(6H, 3.184(4H,m), 4.162(1H,dd,J=7.2 Hz,14.2 Hz), 4.420(1H,dd,J=4.0 Hz,14.2 Hz), 4.651(1H,m), 4.782(1H,t,J=7.5 Hz), 4.908(1H,t,J=7.5 Hz), 5.000(1H,m), 7.978(1H,d,J=7.4 Hz), 7.696(2H,d,J=8.SHz), 7.801(2H,d,J=8.8 Hz), 8.734(1H,s)

EXAMPLE 82

4-[6,7-bis(11-cyclohexylundecylcarbamoyloxy)-4-thiaheptanoylamino] benzoylglutamic acid 4-[6,7-bis(11-cyclohexylundecylcarbamoyloxy)-4-thiaheptanoylamino] benzoylglutamic acid di-t-butyl ester (70 mg, 0.07 mM) as obtained in Example 81 was dissolved in trifiuoroacetic acid (1.0 ml), followed by stirring at room temperature for 1 hour. The reaction mixture was concentrated to dryness under reduced pressure. To the resulting residue, toluene (1 ml) was added and the mixture was concentrated to dryness under reduced pressure. This operation was repeated again and the resulting residue was dissolved in dichloromethane (1 ml) and then concentrated to dryness under reduced pressure to yield the title compound (69 mg, yield 100%) as a colorless solid.

IR(neat) υ; 3300, 2920, 2850, 1700, 1530, 1500, 1440, 1400, 1250, 1180, 1150 cm$^{-1}$
$^1$H-NMR(CDCl$_3$+CD$_3$OD)3; 0.858(4H,m), 1.190(4H,m), 1.252(42H,s), 1.493(4H,m), 1.697(12H,m), 2.00–2.42(2H, m), 2.512(2H,q,J=5.2 Hz), 2.736(4H,m), 2.931(2H,m), 3.140(4H,t,J =7.2 Hz), 4.10–4.45(2H,m), 4.711(1H,m), 4.981(1H,m), 7.652(2H,d,J =8.8 Hz), 7.784(2H,d,J=8.8 Hz)

EXAMPLE 83

4-[6,7,bis(11-cyclohexylundecylcarbamoyloxy)-4-thiaheptanoylminomethyl] benzoylglutamic acid di-t-butyl ester 6,7-bi s( 11-cyclohexylundecylcarbamoyloxy)-4-thiaheptanoic acid (145 mg, 0.196 mM) as obtained in Reference Example 51 and 4aminomethylbenzoylglutamic acid di-t-butyl ester (101 mg, 0.235 mM) and diethyl cyanophosphate (48 mg, 0.234 raM) were dissolved in dimethylformamide (2.0 ml). To the mixture, triethylamine (80 mg, 0.8 mM) was added under ice cooling conditions. The reaction mixture was stirred under ice cooling conditions for 1 hour, and then concentrated to dryness under reduced pressure. The resulting residue was washed with water (5 ml) and then purified by silica gel colum (5 g) (n-hexane-chloroform (1:4) -+ chloroform) to yield the title compound (221 mg, yield 100%) as a colorless solid.

IR(neat) υ; 3300, 2920, 2850, 1720, 1700, 1645, 1535, 1500, 1445, 1360, 1250, 1145 cm$^{-1}$ 1H-NMR(CDCl$_3$)δ; 0.865(4H,m), 1.177(4H,m), 1.248(42H,s), 1.422(9H,s), 1.455(4H,m), 1.492(9H,s), 1.680(12H,m), 1.95–2.28(2H,m), 2.28–2.48(2H,m 2.572(2H,t,J=6.6 Hz), 2.692(2H,m), 2.928(2H,m), 3.120(4H,m), 4.00– 4.35(2H,m), 4.504(2H, m), 4.650(1H,m), 4.933(3H,m), 6.685(1H,m), 7.062( 1H,d, J=7.0 Hz), 7.382(2H,d,J=8.2 Hz), 7.793(2H,d,J=8.2 Hz)

EXAMPLE 84

4-[6,7-bis(11-cyclohexylundecylcarbamoyloxy)-4thiaheptanoylamino)benzoylglutamic acid di-t-buty ester 4-[6,7-bis(11-cyclohexylundecylcarbamoyloxy)-4-thiaheptanoylaminomethyl] benzoylglutamic acid di-t-butyl ester (140 mg, 0.133 mM) as obtained in Example 83 was dissolved in trifluoroacetic acid (1 ml), followed by stirring at room temperature for 1 hour. The reaction mixture was concentrated to dryness under reduced pressure. To the resulting residue, toluene (1 ml) was added and the mixture was concentrated to dryness under reduced pressure. This operation was repeated again to yield the title compound (126 mg, yield 100%) as a colorless solid.

IR(KBr) υ; 3340, 2920, 2850, 1730, 1690, 1635, 1530, 1500, 1440, 1300, 1290, 270, 1250, 1200, 1150, 1115 cm$^{-1}$
$^1$H-NMR(CDCl$_3$) δ; 0.862(2H,m), 1.155(10H,m), 1,246(36H,s), 1.482(4H,m), 1.676(10H,m), 2.282(2H,m), 2.568(2H,m), 2.290(2H,m), 3.153(6H,m), 4.224(2H,m), 4.325(2H,m), 4.739(1H,m), 4.92–5.25(2H,m), 6.224(1H,m), 7.442(2H,d,J=8.2 Hz), 7.808(2H,d,J=8.2 Hz)

EXAMPLE 85

4-((2R,6R)-6,7-bis(palmitoyloxy)-2-methyl-4-thiaheptanoylamino)benzoylglutamic acid di-t-butyl ester To a solution of 4-((2R,6R)-6,7-dihydroxy-2-methyl-4-thiaheptanoylamino)benzoylglutamic acid di-t-butyi ester(58 mg) as obtained in Reference Example 57 in chloroform (2 ml), triethylamine (0.29 ml), palmitoyl chloride (287 mg) and dimethylaminopyridine (1 mg) were added, followed by stirring at room temperature for 3 days. After addition of water, the reaction mixture was extracted with ethyl acetate. The extract was washed with a 5% aqueous solution of citric acid, a saturated aqueous solution of sodium hydrogen carbonate and saturated saline, dried over anhydrous sodium sulfate, and the solvent was distilled off. The resulting residue was purified by silica gel column chromatography (hexane:ethyl acetate=2:1 to 1:1) to yield the title compound (27 mg, yield 25%) as a colorless wax-like substance.

IR(KBr)cm$^{-1}$; 3350, 2920, 2850, 1780, 1640, 1590, 1530, 1500, 1365, 1250, 1150
$^1$H-NMR(CDCl$_3$) δ; 0.88(6H,t,J=6.6 Hz), 1.03–1.40 (51H, m), 1.42(9H,s), 1.49(9H,s), 1.53–1.90(4H,rr,), 1.90–3.10(18H,m), 4.20(1H,dd,J=6.4,12.0H 4.36(1H,dd,J= 3.2,12.0 Hz), 4.61–4.78(1H,m), 5.13–5.28(1H,m), 7.02( 1H,d,J=7.6 Hz), 7.69(2H,d,J=8.6 Hz), 7.80(2H,d,J=8.6 Hz), 8.10( 1H,bs)

EXAMPLE 86

4-((2R,6R)-6,7-bis(palmitoyloxy)-2-methyl-4-thiaheptanoylamino)benzoylglutamic acid 4-((2R,6R)-6,7-bis(palmitoyloxy)-2-methyl-4-thiaheptanoylamino)benzoylglutamic acid di-t-butyl ester (87 mg) as obtained in Example 85 was dissolved in trifluoroacetic acid (4 ml), followed by stirring at room temperature for 24 hours. The reaction mixture was concentrated. The resulting residue was washed with acetonitrile to yield the title compound (87 mg, yield 100%) as a colorless powder.
IR(KBr)cm$^1$; 3280, 2920, 2850, 1735, 1640, 1520, 1465, 1405, 1305, 1240, 1220, 1170
$^1$H-NMR(CDCl$_3$+5% CD$_3$OD) δ; 0.88(6H,t,J=6.8 Hz), 1.03–1.48(51H,m), 1.48– 1.75(4H,s), 2.05–3.20(13H,m), 4.18(1H,dd,J=6.2,12.0 Hz), 4.33(1H,dd,J=3.0,12.0 Hz), 4.65–4.75(1H,m), 5.10–5.25(1H,m), 7.67(2H,d,J=8.6 Hz), 7.80(2H,d,J=8.6 Hz)

EXAMPLE 87

4-(6,7-bis(palmitoyloxy)-4-thiaheptanoylamino) benzoylphenylalanine methyl ester To a solution of 6,7-bis(palmitoyloxy)-4-thiaheptanoic acid (329 mg) as obtained in Reference Example 4 and 4-aminobenzoylphenylalanine methyl ester (149 mg) in pyridine (5 ml), phospholic trichloride (0.044 ml) was added, followed by stirring at room temperature for 72 hours. After addition of water, the reaction mixture was extracted with ethyl acetate. The extract was washed with a 5% aqueous solution of citric acid, a saturated aqueous solution of sodium hydrogen carbonate and saturated saline, dried over anhydrous sodium sulfate, and the solvent was distilled off. The resulting residue was purified by silica gel column chromatography (hexane:ethyl acetate=3:2) to yield the title compound (210 mg, yield 45%) as a colorless wax-like substance.
IR(KBr)cm$^{-1}$; 3320, 2910, 2840, 1730, 1665, 1630, 1500, 1170
$^1$H-NMR(CDCl$_3$) δ; 0.88(6H,t,J=6.8 Hz), 1.05–1.48(48H,m), 1.52–1.74(4 H,m), 2.32(2H,t,J=7.8 Hz), 2.35(2H,t,J=7.6 Hz), 2.62–3.36(8H,m), 3.76(3H,s), 4.14(1H,dd,J=6.6,11.8 Hz), 4.47(1H,dd,J=3.2,11.8 Hz), 5.02–5.25(2H,m), 6.51(1H, d,J=7.8 Hz), 7.07–7.36(8H,m), 7.60–7.74(4H,m), 8.09(1H, bs)

EXAMPLE 88

4-(6,7-bis(palmitoyloxy)-4-thiaheptanoylamino) benzoyltryptophan methyl ester

To a solution of 6,7-bis(palmitoyloxy)-4-thiaheptanoic acid (329 mg) as obtained in Reference Example 4 and 4-aminobenzoyltryptophan methyl ester (169 mg) in pyridine (5 ml), phospholic trichloride (0.022 ml) was added, followed by stirring at room temperature for 24 hours. After addition of water, the reaction mixture was extracted with ethyl acetate. The extract was washed with a 5% aqueous solution of citric acid, a saturated aqueous solution of sodium hydrogen carbonate and saturated saline, dried over anhydrous sodium sulfate, and the solvent was distilled off. The resulting residue was purified by silica gel column chromatography (hexane:acetone = 3:2) to yield the title compound (190 mg, yield 39%) as a colorless wax-like substance.
IR(KBr)cm$^{-1}$; 3390, 3320, 2920, 2850, 1730, 1665, 1630, 1515, 1500, 1170
$^1$H-NMR(CDCl$_3$) δ; 0.88(6H,t,J=6.6 Hz), 1.03–1.50(48H, m), 1.50–1,75(4 H,m), 2.34(2H,t,J=7.6 Hz), 2.35(2H,t,J=7.6 Hz), 2.60–3.10(6H,m), 3.44(2H,d,J=5.2 Hz), 3.71(3H,s), 4.03–4.50(2H,m), 5.04–5.22(2H,m), 6.65(1H,d,J=7.6 Hz), 6.96–7.67(9H,m), 8.25(1H,s), 8.36(1H,s)

EXAMPLE 89

4-(6,7-bis(palmitoyloxy)-4-thiaheptanoylamino) benzoylphenylalanine t-butyl ester To a solution of 4-aminobenzoylphenylalanine t-butyl ester (170 mg) in pyridine (5 ml), phospholic trichloride (0.022 ml) was added, followed by stirring at room temperature for 2 hours. After addition of 6,7-bis(palmitoyloxy)- 4-thiaheptanoic acid (164 mg) as obtained in Reference Example 4, the reaction mixture was stirred at room temperature for 24 hours. After addition of water, the reaction mixture was extracted with ethyl acetate. The extract was washed with a 5% aqueous solution of citric acid, a saturated aqueous solution of sodium hydrogen carbonate and saturated saline, dried over anhydrous sodium sulfate, and the solvent was distilled off. The resulting residue was purified by silica gel column chromatography (hexane:ethyl acetate=3:2) to yield the title compound (208 mg, yield 86%) as a colorless wax-like substance.
IR(KBr)cm$^{-1}$; 3320, 2920, 2850, 1730, 1635, 1500, 1160
$^1$H-NMR(CDCl$_3$)δ; 0.88(6H,t,J=6.6 Hz), 1.04–1.40(48H, m), 1.44(9H,s), 1.52– 1.77(4H,m), 2.33(2H,t,J=7.6 Hz), 2.35(2H,t,J = 7.6 Hz), 2.62–3.15(6H,m), 3.22(2H,d,J=5.8 Hz), 4.14(1H,dd,J=6.6,12.0 Hz), 4.47(1H,dd,J=3.2,12.0 Hz), 4.87–5.00(1H,m), 5.10–5.23(1H,m), 6.58(1H,d,J = 7.4 Hz), 7.13–7.34(5H 7.58–7.76(4H,m), 8.07(1H,bs)

EXAMPLE 90

4-(6,7-bis(palmitoyloxy)-4-thiaheptanoylamino) benzoylphenylalanine 4-(6,7-bis(palmitoyloxy)-4-thiaheptanoylamino)benzoylphenylalanine t-butyl ester (206 mg) as obtained in Example 89 was dissolved in trifluoroacetic acid (4 ml), followed by stirring at room temperature for 4 hours. The reaction mixture was concentrated and the resulting residue was washed with acetonitrile to yield the title compound (182 mg, yield 92%) as a colorless powder.
IR(KBr)cm$^1$; 3320, 2910, 2840, 1730, 1710, 1665, 1635, 1510
$^1$H-NMR(CDCl$_3$)δ; 0.88(6H,t,J=6.8 Hz), 1.02–1.48(48H, m), 1.52–1.72(4H,m), 2.32(2H,t,J=7.6 Hz), 2.35(2H,t,J=7.4 Hz), 2.62–3.44(4H,m), 4.14( 1H,dd, J=6.6,11.8 Hz), 4.46(1H,dd, J=3.0,11.8 Hz), 4.95–5.23(2 6.54(1H,d, J=7.4 Hz), 7.16–7.65(9H,m), 8.23(1H,bs)

EXAMPLE 91

4-(6,7-bis(palmitoyloxy)-4-thiaheptanoylamino) benzoylmethionine t-butyl ester

To a solution of 4-aminobenzoylmethionine t-butyl ester (160 mg) in pyridine (5 ml), phospholic trichloride (0.022 ml) was added, followed by stirring at room temperature for 2 hours. After addition of 6,7-bis(palmitoyloxy)- 4-thiaheptanoic acid ( 164 mg) as obtained in Reference Example 4, the reaction mixture was stirred at room temperature for 24 hours. After addition of water, the reaction mixture was extracted with ethyl acetate. The extract was washed with a 5% aqueous solution of citric acid, a saturated aqueous solution of sodium hydrogen carbonate and saturated saline, dried over anhydrous sodium sulfate, and the solvent was distilled off. The resulting residue was purified by silica gel column chromatography (hexane:ethyl acetate=3:2) to yield the title compound (163 mg, yield 68%) as a colorless wax-like substance.
IR(KBr)cm$^{-1}$; 3310, 2910, 2850, 1735, 1670, 1630, 1590, 1530, 1500, 1150
$^1$H-NMR(CDCl$_3$)δ; 0.88(6H,t,J=6.6 Hz), 1.05–1.43(48H, m), 1.45(9H,s), 1.54– 1.73(4H,m), 1.95–3.10(14H,m), 2.11(3H,s), 4.15(1H,dd,J=6.8,12.2 Hz), 4.46( 1H,dd,J=2.6, 12.2 Hz), 4.72–4.86(1H,m), 5.10–5.25(1H,m), 6.88(1H,d,J= 7.8 Hz), 7.67(2H,d,J=8.4 Hz), 7.79(2H,d,J=8.4 Hz), 8.10 (1 H,bs)

EXAMPLE 92

4-(6,7-bis(palmitoyloxy)-4-thiaheptanoylamino) benzoylmethionine 4-(6,7-bis(palmitoyloxy)-4-thiaheptanoylamino)benzoyl-methionine t-butyl ester (162 mg) as obtained in Example 91 was dissolved in trifluoroacetic acid (4 ml), followed by stirring at room temperature for 24 hours. The reaction mixture was concentrated and the resulting residue was washed with acetonitrile to yield the title compound (149 mg, yield 100%) as a colorless powder.
IR(KBr)cm$^{-1}$; 2900, 2840, 1730, 1520, 1175
$^1$H-NMR(CDCl$_3$)δ; 0.88(6H,t,J=6.8 Hz), 1.03–1.48(48H, m), 1.48–1.73( 4H,m), 2.12(3H,s), 2.16–3.06(10H,m), 4.10–5.28(4H,m), 7.57(2H,d,J=8.2 Hz), 7.71(2H,d,J=8.2 Hz), 8.49(1H,s)

EXAMPLE 93

4-[6(R),7-bis(palmitoyloxy)-4-thiaheptanoylamino] benzoylglutamic acid di-t-butyl ester To a solution of 4-[6(R),7-dihydroxy-4thiaheptanoy-lamino] benzoylglutamic acid di-t-butyl ester (825 mg) as obtained in Reference Example 58 and dimethylaminopyridine (470 mg) in dichloromethane (15 ml), palmitoyl chloride (882 mg)was added, followed by stirring at room temperature for 2 hours. The solvent was concentrated and the resulting residue was purified by silica gel column chromatography (nhexane: ethyl acetate=2:1) to yield the title compound (1.377 g, yield 89%) as a colorless amorphous substance.
IR(neat)υ; 3330, 2920, 2850, 1730, 1635, 1595, 1520, 1500, 1360, 1250, 1150 cm$^{-1}$
$^1$H-NMR(CDCl$_3$)δ; 0.88(6H,t,J=6.8 Hz), 1.25(48H,s), 1.42(9H,s), 1.49 (9H,s), 1.50–1.75(4H,m), 1.90–2.50(8H, m), 2.60–3.10(6H,m), 4.15(1H,dd,J=12.0,6.6 Hz), 4.46(1H, J=12.0,3.0 Hz), 4.66(1H,m), 5.18(1H,m), 7.00(1H,d,J=7.2 Hz), 7.65(2H,d,J=8.5Hz), 7.80( 2H,d,J=8.8 Hz), 8.16( 1H,brs)

EXAMPLE 94

4-[6(R), 7- bis(palmitoyloxy)-4-thiaheptanoyl amino]benzoylglutamic acid

To a solution of 4-[6(R),7-bis(palmitoyloxy)-4thiahep-tanoylamino] benzoylglutamic acid di-t-butyl ester (1.375 g) as obtained in Example 93 in dichloromethane (2 ml), trifluoroacetic acid (6 ml) was added, followed by stirring at room temperature for 1 hour. After solvent concentration under reduced pressure, the resulting residue was crystallized from methanol-water to yield the title compound (1.12 g, yield 92%) as a colorless powder.
IR(KBr)υ; 3450, 1735, 1640 cm$^{-1}$
$^1$H-NMR(CDCl$_3$–CD$_3$OD)δ; 0.88(6H,t,J=6.8 Hz), 1.25(48H,s), 1.50– 1.70(4H,m), 2.05–3.00(14H,m), 4.16(1H,dd,J=12.0,6.4 Hz), 4.42(1H,dd,J=12.0,2.6 Hz), 4.70(1H,m), 5.17(1H,m), 7.51(1H,d,J=7.2 Hz), 7.63(2H,d, J=8.8 Hz), 7.78(2H,d,J=8.8 Hz), 9.00(1H,s)

EXAMPLE 95

4-[6(R),7-bis(12-phenyldodecanoyloxy)-thiaheptanoylamino] benzoylglutamic acid di-t-butyl ester To a solution of 4-[6(R),7-dihydroxy-4thiaheptanoy-lamino] benzoylglutamic acid di-t-butyl ester (900 mg) as obtained in Reference Example 58, 12-phenyldodecanoic acid (966 mg) and dimethylaminopyridine (520 mg) in acetonitrile (15 ml)-tetrahydrofuran (3 ml), diisopropylcar-bodiimide (525 mg) was added, followed by stirring at room temperature for 1 night. The solvent was concentrated and the resulting residue was purified by silica gel column chromatography (n-hexane: ethyl acetate = 2:1) to yield the title compound (937 mg, yield 53%) as a colorless amorphous substance.
IR(neat)υ; 3300, 2920, 2850, 1730, 1700, 1630, 1590, 1520, 1500, 1490, 1360, 250, 1150 cm$^{-1}$
$^1$H-NMR(CDCl$_3$)δ; 1.26(28H,s), 1.42(9H,s), 1.49(9H,s), 1.50–1.70(8H,m), 1.90–2.50(8H,m), 2.50–3.10(10H,m), 4.15(1H,dd,J=12.0,6.6 Hz), 4.46(1H,dd,J=12.0,3.2 Hz), 4.65(1H,m), 5.17(1H,m), 6.98(1H,d,J=7.2 Hz), 7.10–7.35(10H,m), 7.64(2H,d,J=8.8 Hz), 7.80(2H,d,J=8.8 Hz), 8.07(1H,s)

EXAMPLE 96

4-[6(R ), 7-bis(12-phenyldodecanoyloxy)-4thiaheptanoylamino] benzoylglutamic acid 4-[ 6(R ), 7-bis(12-phenyldodecanoyloxy)-4-thiahep-tanoylamino] benzoylglutamic acid di-t-butyl ester (935 mg) as obtained in Example 95 in dichloromethane (2 ml), trifluoroacetic acid (6 ml) was added, followed by stirring at room temperature for 1 hour. The solvent was distilled off under reduced to yield the title compound (181 mg, yield 83%) as a colorless syrup.
IR(neat)υ; 3300, 2920, 2850, 1730, 1710, 1630, 1600, 1520, 1500, 1490, 1450, 1400, 1305, 1250, 1175 cm$^{-1}$
$^1$H-NMR(CDCl$_3$)δ; 1.24(28H,s), 1.50–1.70(8H,m), 1.90–2.80(12H,m), 2.57(4H,t,J=8.0 Hz), 2.80–3.00(2H,m), 4.11(1H,dd,J=12.0,6.2 Hz), 4.39(1H,dd,J=12.0,2.4 Hz), 4.62(1H,m), 5.16(1H,m), 7.10–7.30(10H,m), 7.43(2H,d,J= 8.2 Hz), 7.66(2H,d,J=8.2 Hz), 7.70–7.85(1H,m), 8.88(1H,s

EXAMPLE 97

4-[6(R), 7-bis(palmitoyloxy)-4-thia-2(E)-heptenoylaminomethyl] benzoylglutamic acid di-t-butyl ester 6(R),7-bis(palmitoyloxy)-4-thia-2(E)-heptenoic acid (1.0 g) as obtained in Reference Example 62 and a solution of 4-(aminomethyl)benzoylglutamic acid di-t-butyl ester hydrochloride (735 mg) as obtained in Reference Example 37, DEPC (375 mg) and triethylamine (600 mg) in dimeth-ylformamide (15 ml)-dichloromethane (5 ml) were stirred at room temperature for 1 hour. The solvent was concentrated under reduced pressure and the resulting residue was purified by silica gel column chromatography (n-hexane: ethyl acetate= 1) to yield the title compound (893 mg, yield 57%) as a colorless amorphous substance.
IR(neat)υ; 8300, 2920, 2850, 1735, 1640, 1580, 1540, 1460, 1365, 1250, 1150 cm$^{-1}$ ¹H-NMR(CDCl₃)δ; 0.88(6H,t,J=6.6 Hz), 1.25(48H,s), 1.42(9H,s), 1.49 (9H,s), 1.50–1.70(4H,m), 1.95–2.50(8H,m), 2.96(1H,dd,J=14.4,7.2 Hz), 3.08(1H,dd,J=14.4,6.4 Hz), 4.20(1H,dd,J=12.0,5.4 Hz), 4.35( 1H,dd,J=12.0,8.6 Hz), 4.55(2H,d,J=5.8 Hz), 4.65(1H,m), 5.19(1H,m), 5.94(1H, brs), 6.00(1H,d,J=18.6 Hz), 7.02(1H,d,J=7.6 Hz), 7.34(2H, d,J=8.2 Hz), 7.57(1H,d,J=18.6 Hz), 7.77(2H,d,J=8.2 Hz)

EXAMPLE 98

4-[6(R), 7-bis(palmitoyloxy)-4-thia-2(E)-heptenoylaminomethyl] benzoylglutamic acid 4-[6(R ), 7-bis(palmitoyloxy)-4-thia-2(E)-heptenoylaminomethyl] benzoylglutamic acid di-t-butyl ester (890 mg) as obtained in Example 97 was dissolved in trifluoroacetic acid (6 ml), followed by stirring at room temperature for 1 hour. After solvent concentration under reduced pressure, the resulting residue was crystallized from methanol-water to yield the title compound (730 mg, yield 92%) as a colorless crystal.

IR(KBr) υ; 3296, 2919, 2852, 1739, 1633, 1575, 1544, 1247, 1180 cm⁻¹

¹H-NMR(CDCl₃)δ; 0.88(6H,t,J=6.6 Hz), 1.25(48H,s), 1.50–1.70(4H,m), 1.95–2.50(8H,m), 2.90–3.10(2H,m), 4.16(1H,dd,J=12.0,5.4 Hz), 4.30–4.45(3H,m), 4.60(1H,m), 5.20(1H,m), 6.06(1H,d,J=15.2 Hz), 7.10(2H,d,J=8.2 Hz), 7.10–7.20(1H,m), 7.50–7.65(3H,m), 7.82(1H,m)

Tables 1 through 10 show the structures of the compounds [I] of the present invention or salts thereof obtained in Examples above.

TABLE 1

| Example Number | R¹ | R² | R³ | R⁴ | R⁵ | R⁶ | R⁷ | n | X | Y |
|---|---|---|---|---|---|---|---|---|---|---|
| 1 | COC₁₅H₃₁ | COC₁₅H₃₁ | H | H | H | H | H | 0 | CO | Gly(OᵗBu) |
| 2 | COC₁₅H₃₁ | COC₁₅H₃₁ | H | H | H | H | H | 0 | CO | Gly—OH |
| 3 | COC₁₅H₃₁ | COC₁₅H₃₁ | H | H | H | H | H | 0 | CO | Gly—Gly(OᵗBu) |
| 4 | COC₁₅H₃₁ | COC₁₅H₃₁ | H | H | H | H | H | 0 | CO | Gly—Gly—OH |
| 5 | COC₁₅H₃₁ | COC₁₅H₃₁ | H | H | H | H | H | 0 | CO | (Gly)₂—Gly(OᵗBu) |
| 6 | COC₁₅H₃₁ | COC₁₅H₃₁ | H | H | H | H | H | 0 | CO | (Gly)₂—Gly—OH |
| 7 | COC₁₅H₃₁ | COC₁₅H₃₁ | H | H | H | H | H | 0 | CO | (Gly)₃—Glu(OᵗBu)₂ |
| 8 | COC₁₅H₃₁ | COC₁₅H₃₁ | H | H | H | H | H | 0 | CO | (Gly)₃—Glu(OH)₂ |
| 9 | COC₁₅H₃₁ | COC₁₅H₃₁ | H | H | H | H | H | 0 | CO | NH(CH₂)₇CO—Glu(OᵗBu)₂ |
| 10 | COC₁₅H₃₁ | COC₁₅H₃₁ | H | H | H | H | H | 0 | CO | NH(CH₂)₇CO—Glu(OH)₂ |

TABLE 2

| Example Number | R¹ | R² | R³ | R⁴ | R⁵ | R⁶ | R⁷ | n | X | Y |
|---|---|---|---|---|---|---|---|---|---|---|
| 11 | COC₁₅H₃₁ | COC₁₅H₃₁ | H | H | H | H | H | 0 | CO | NH(CH₂)₃CHCO(Gly)₂Glu(OᵗBu)₂<br>                   \|<br>                   NHCOOᵗBu |
| 12 | COC₁₅H₃₁ | COC₁₅H₃₁ | H | H | H | H | H | 0 | CO | NH(CH₂)₃CHCO(Gly)₂Glu(OH)₂<br>                   \|<br>                   NH₂.HCl |
| 13 | COC₁₅H₃₁ | COC₁₅H₃₁ | H | H | H | H | H | 0 | CO | NHCHCO(Gly)₂—Glu(OᵗBu)₂<br>    \|<br>(CH₂)₃—NHCOOᵗBu |
| 14 | COC₁₅H₃₁ | COC₁₅H₃₁ | H | H | H | H | H | 0 | CO | NHCHCO(Gly)₂—Glu(OH)₂<br>    \|<br>(CH₂)₃—NH₂.HCl |
| 15 | COC₁₅H₃₁ | COC₁₅H₃₁ | H | H | H | H | H | 0 | CO | NHCHCO(Gly)₂—Glu(OᵗBu)₂<br>    \|<br>(CH₂)₄NHCOOᵗBu |
| 16 | COC₁₅H₃₁ | COC₁₅H₃₁ | H | H | H | H | H | 0 | CO | NHCHCO(Gly)₂—Glu(OH)₂<br>    \|<br>(CH₂)₄—NH₂.HCl |
| 17 | COC₁₅H₃₁ | COC₁₅H₃₁ | H | H | H | H | H | 0 | CO | 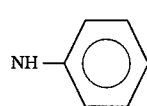 NH—C₆H₄—CO—Glu(OᵗBu)₂ |
| 18 | COC₁₅H₃₁ | COC₁₅H₃₁ | H | H | H | H | H | 0 | CO | 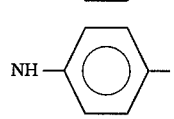 NH—C₆H₄—CO—Glu(OH)₂ |

TABLE 2-continued

| Example Number | R¹ | R² | R³ | R⁴ | R⁵ | R⁶ | R⁷ | n | X | Y |
|---|---|---|---|---|---|---|---|---|---|---|
| 19 | $COC_{15}H_{31}$ | $COC_{15}H_{31}$ | H | H | H | H | H | 0 | CO | NH—⟨C₆H₄⟩—$SO_2$—Glu(O$^t$Bu)$_2$ |
| 20 | $COC_{15}H_{31}$ | $COC_{15}H_{31}$ | H | H | H | H | H | 0 | CO | NH—⟨C₆H₄⟩—$SO_2$—Glu(OH)$_2$ |

TABLE 3

| Example Number | R¹ | R² | R³ | R⁴ | R⁵ | R⁶ | R⁷ | n | X | Y |
|---|---|---|---|---|---|---|---|---|---|---|
| 21 | $COC_{15}H_{31}$ | $COC_{15}H_{31}$ | H | H | H | H | H | 0 | CO | NH—⟨C₆H₄⟩—CO—Asp(O$^t$Bu)$_2$ |
| 22 | $COC_{15}H_{31}$ | $COC_{15}H_{31}$ | H | H | H | H | H | 0 | CO | NH—⟨C₆H₄⟩—CO—Asp(OH)$_2$ |
| 23 | $COC_{13}H_{27}$ | $COC_{13}H_{27}$ | H | H | H | H | H | 0 | CO | NH—⟨C₆H₄⟩—CO—Glu(O$^t$Bu)$_2$ |
| 24 | $COC_{13}H_{27}$ | $COC_{13}H_{27}$ | H | H | H | H | H | 0 | CO | NH—⟨C₆H₄⟩—CO—Glu(OH)$_2$ |
| 25 | $COC_{17}H_{35}$ | $COC_{17}H_{35}$ | H | H | H | H | H | 0 | CO | NH—⟨C₆H₄⟩—CO—Glu(O$^t$Bu)$_2$ |
| 26 | $COC_{17}H_{35}$ | $COC_{17}H_{35}$ | H | H | H | H | H | 0 | CO | NH—⟨C₆H₄⟩—CO—Glu(OH)$_2$ |
| 27 | $CO(CH_2)_7CH=CHC_8H_{17}$ | $CO(CH_2)_7CH=CHC_8H_{17}$ | H | H | H | H | H | 0 | CO | NH—⟨C₆H₄⟩—CO—Glu(O$^t$Bu)$_2$ |
| 28 | $CO(CH_2)_7CH=CHC_8H_{17}$ | $CO(CH_2)_7CH=CHC_8H_{17}$ | H | H | H | H | H | 0 | CO | NH—⟨C₆H₄⟩—CO—Glu(OH)$_2$ |
| 29 | $CONHC_{18}H_{37}$ | $COC_{15}H_{31}$ | H | H | H | H | H | 0 | CO | NH—⟨C₆H₄⟩—CO—Glu(O$^t$Bu)$_2$ |
| 30 | $CONHC_{18}H_{37}$ | $COC_{15}H_{31}$ | H | H | H | H | H | 0 | CO | NH—⟨C₆H₄⟩—CO—Glu(OH)$_2$ |

TABLE 4

| Example Number | R¹ | R² | R³ | R⁴ | R⁵ | R⁶ | R⁷ | n | X | Y |
|---|---|---|---|---|---|---|---|---|---|---|
| 31 | CONHC$_{18}$C$_{37}$ | CONHC$_{18}$C$_{37}$ | H | H | H | H | H | 0 | CO | NH—⟨C$_6$H$_4$⟩—CO—Glu(O$^t$Bu)$_2$ |
| 32 | CONHC$_{18}$C$_{37}$ | CONHC$_{18}$C$_{37}$ | H | H | H | H | H | 0 | CO | NH—⟨C$_6$H$_4$⟩—CO—Glu(OH)$_2$ |
| 33 | COC$_{15}$H$_{31}$ | COC$_{15}$H$_{31}$ | H | Bond | H | H | 0 | | CO | (Gly)$_3$—Glu(O$^t$Bu)$_2$ |
| 34 | COC$_{15}$H$_{31}$ | COC$_{15}$H$_{31}$ | H | Bond | H | H | 0 | | CO | (Gly)$_3$—Glu(OH)$_2$ |
| 35 | COC$_{15}$H$_{31}$ | COC$_{15}$H$_{31}$ | H | Bond | H | H | 0 | | CO | (Gly)$_3$—Glu(O$^t$Bu)$_2$ |
| 36 | COC$_{15}$H$_{31}$ | COC$_{15}$H$_{31}$ | H | Bond | H | H | 0 | | CO | (Gly)$_3$—Glu(OH)$_2$ |
| 37 | COC$_{15}$H$_{31}$ | COC$_{15}$H$_{31}$ | H | Bond | H | H | 0 | | CO | NH(CH$_2$)$_3$CH(NH—Boc)CO(Gly)$_2$—Glu(O$^t$Bu)$_2$ |
| 38 | COC$_{15}$H$_{31}$ | COC$_{15}$H$_{31}$ | H | Bond | H | H | 0 | | CO | NH(CH$_2$)$_3$CH(NH$_2$·HCl)CO(Gly)$_2$—Glu(OH)$_2$ |
| 39 | COC$_{15}$H$_{31}$ | COC$_{15}$H$_{31}$ | H | H | H | H | H | 0 | CO | NHCH$_2$—⟨C$_6$H$_4$⟩—CO—Glu(O$^t$Bu)$_2$ |
| 40 | COC$_{15}$H$_{31}$ | COC$_{15}$H$_{31}$ | H | H | H | H | H | 0 | CO | NHCH$_2$—⟨C$_6$H$_4$⟩—CO—Glu(OH)$_2$ |

TABLE 5

| Example Number | R¹ | R² | R³ | R⁴ | R⁵ | R⁶ | R⁷ | n | X | Y |
|---|---|---|---|---|---|---|---|---|---|---|
| 41 | COC$_{15}$H$_{31}$ | COC$_{15}$H$_{31}$ | H | H | H | H | H | 0 | SO$_2$ | N(COO$^t$Bu)—CH$_2$CO(Gly)$_2$—Glu(OtBu)$_2$ |
| 42 | COC$_{15}$H$_{31}$ | COC$_{15}$H$_{31}$ | H | H | H | H | H | 0 | SO$_2$ | NH=CH$_2$CO(Gly)$_2$—Glu(OH)$_2$ |
| 43 | COC$_{15}$H$_{31}$ | COC$_{15}$H$_{31}$ | H | H | H | H | H | 0 | SO$_2$ | N(Boc)—(CH$_2$)$_5$CO—Glu(O$^t$Bu)$_2$ |
| 44 | COC$_{15}$H$_{31}$ | COC$_{15}$H$_{31}$ | H | H | H | H | H | 0 | SO$_2$ | NH—(CH$_2$)$_5$CO—Glu(OH)$_2$ |
| 45 | COC$_{15}$H$_{31}$ | COC$_{15}$H$_{31}$ | H | H | H | H | H | 0 | CO | NH—⟨C$_6$H$_4$⟩—COO$^t$Bu |
| 46 | COC$_{15}$H$_{31}$ | COC$_{15}$H$_{31}$ | H | H | H | H | H | 0 | CO | NH—⟨C$_6$H$_4$⟩—CO—Glu(O$^t$Bu)—Glu(O$^t$Bu)$_2$ |
| 47 | COC$_{15}$H$_{31}$ | COC$_{15}$H$_{31}$ | H | H | H | H | H | 0 | CO | NH—⟨C$_6$H$_4$⟩—CO—Glu(OH)—Glu(OH)$_2$ |
| 48 | COC$_{15}$H$_{31}$ | COC$_{15}$H$_{31}$ | H | Bond | H | H | 0 | | CO | NHCH$_2$—⟨C$_6$H$_4$⟩—CO—Glu(O$^t$Bu)$_2$ |

TABLE 5-continued
| Example Number | R¹ | R² | R³ | R⁴ | R⁵ | R⁶ | R⁷ | n | X | Y |
|---|---|---|---|---|---|---|---|---|---|---|
| 49 | $COC_{15}H_{31}$ | $COC_{15}H_{31}$ | H | Bond | H | H | H | 0 | CO | 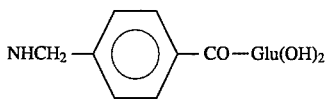 |
| 50 | $COC_{15}H_{31}$ | $COC_{15}H_{31}$ | H | H | H | H | H | 0 | CO | 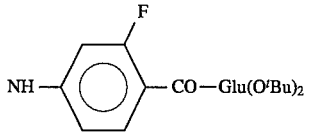 |
TABLE 6
| Example Number | R¹ | R² | R³ | R⁴ | R⁵ |
|---|---|---|---|---|---|
| 51 | $COC_{15}H_{31}$ | $COC_{15}H_{31}$ | H | H | H |
| 52 | $COC_{11}H_{23}$ | $COC_{11}H_{23}$ | H | H | H |
| 53 | $COC_{11}H_{23}$ | $COC_{11}H_{23}$ | H | H | H |
| 54 | $COC_{15}H_{31}$ | $COC_{15}H_{31}$ | $CH_3$ | H | H |
| 55 | $COC_{15}H_{31}$ | $COC_{15}H_{31}$ | $CH_3$ | H | H |
| 56 | $COC_{15}H_{31}$ | $COC_{15}H_{31}$ | H | H | H |
| 57 | $COC_{15}H_{31}$ | $COC_{15}H_{31}$ | H | H | H |
| 58 | 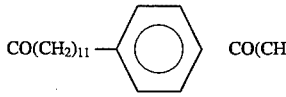 | 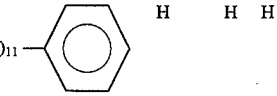 | H | H | H |
| 59 | 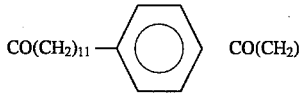 | 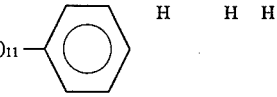 | H | H | H |
| 60 | 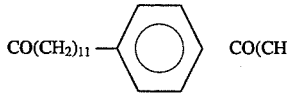 | 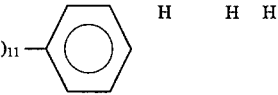 | H | H | H |
| Example Number | R⁶ | R⁷ | n | X | Y |
|---|---|---|---|---|---|
| 51 | H | H | 0 | CO | 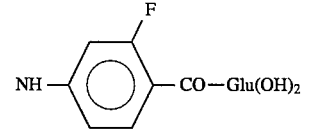 |
| 52 | H | H | 0 | CO | 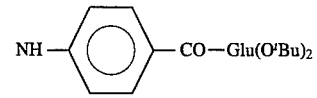 |
| 53 | H | H | 0 | CO | 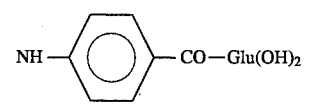 |
| 54 | H | H | 0 | CO | 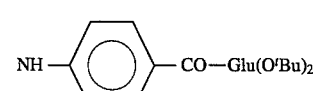 |
| 55 | H | H | 0 | CO | 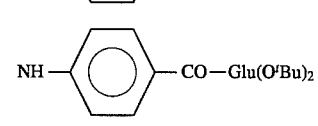 |

TABLE 6-continued

| | | | | | | |
|---|---|---|---|---|---|---|
| 56 | H | H | 0 | SO$_2$ | NCH$_2$—⟨Ph⟩—CO—Glu(O$^t$Bu)$_2$ with Boc on N | |
| 57 | H | H | 0 | SO$_2$ | NHCH$_2$—⟨Ph⟩—CO—Glu(OH)$_2$ | |
| 58 | H | H | 0 | CO | NHCH$_2$—⟨Ph⟩—CO—Glu(O$^t$Bu)$_2$ | |
| 59 | H | H | 0 | CO | NHCH$_2$—⟨Ph⟩—CO—Glu(OH)$_2$ | |
| 60 | H | H | 0 | CO | NH—⟨Ph⟩—CO—Glu(O$^t$Bu)$_2$ | |

TABLE 7

| Example Number | R$^1$ | R$^2$ | R$^3$ | R$^4$ | R$^5$ | R$^6$ | R$^7$ |
|---|---|---|---|---|---|---|---|
| 61 | CO(CH$_2$)$_{11}$—⟨Ph⟩ | CO(CH$_2$)$_{11}$—⟨Ph⟩ | H | H | H | H | H |
| 62 | COC$_{15}$H$_{31}$ | COC$_{15}$H$_{31}$ | H | H | H | H | H |
| 63 | COC$_{15}$H$_{31}$ | COC$_{15}$H$_{31}$ | H | H | H | H | H |
| 64 | COC$_{15}$H$_{31}$ | COC$_{15}$H$_{31}$ | H | H | H | H | H |
| 65 | COC$_{15}$H$_{31}$ | COC$_{15}$H$_{31}$ | H | H | H | H | H |
| 66(A) | COC$_{15}$H$_{31}$ | COC$_{15}$H$_{31}$ | H | H | H | H | H |
| 66(B) | COC$_{15}$H$_{31}$ | COC$_{15}$H$_{31}$ | H | H | H | H | H |
| 67 | COC$_{15}$H$_{31}$ | COC$_{15}$H$_{31}$ | H | H | H | H | H |

| Example | n | X | Y |
|---|---|---|---|
| 61 | 0 | CO | NH—⟨Ph⟩—CO—Glu(OH)$_2$ |
| 62 | 0 | CO | NH—⟨Ph with ortho-CO-N-CH(COO$^t$Bu)—CH$_2$CH$_2$COO$^t$Bu⟩ |
| 63 | 0 | CO | NH—⟨Ph with ortho-CO-N-CH(COOH)—CH$_2$CH$_2$COOH⟩ |

TABLE 7-continued
| | | | |
|---|---|---|---|
| 64 | 0 | CO | 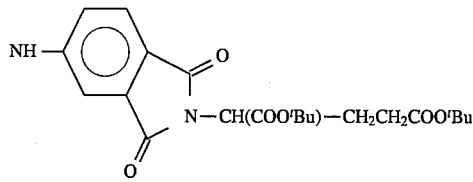 |
| 65 | 0 | CO | 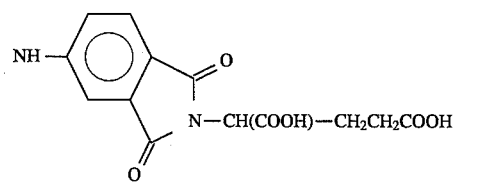 |
| 66(A) | 1 | CO | 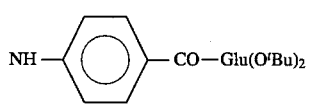 |
| 66(B) | 2 | CO | 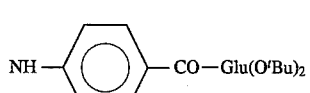 |
| 67 | 1 | CO | 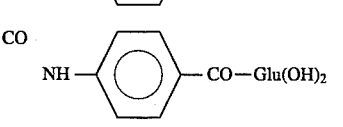 |
TABLE 8
| Example Number | R¹ | R² | R³ | R⁴ | R⁵ | R⁶ | R⁷ | n | X | Y |
|---|---|---|---|---|---|---|---|---|---|---|
| 68 | COC$_{15}$H$_{31}$ | COC$_{15}$H$_{31}$ | H | H | H | H | H | 2 | CO | 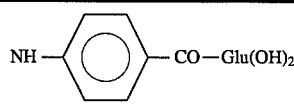 |
| 69 | COC$_{15}$H$_{23}$ | COC$_{15}$H$_{31}$ | H | H | CH$_3$COO | H | H | 0 | CO | 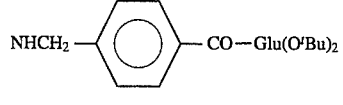 |
| 70 | COC$_{15}$H$_{31}$ | COC$_{15}$H$_{31}$ | H | H | CH$_3$COO | H | H | 0 | CO | 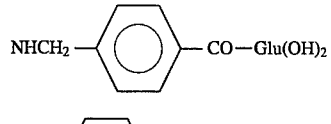 |
| 71 | COC$_{15}$H$_{31}$ | COC$_{15}$H$_{31}$ | H | H | CH$_3$ | H | H | 0 | CO | 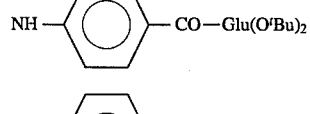 |
| 72 | COC$_{15}$H$_{31}$ | COC$_{15}$H$_{31}$ | H | H | CH$_3$ | H | H | 0 | CO | 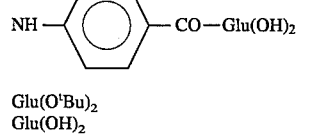 |
| 73 | COC$_{15}$H$_{31}$ | COC$_{15}$H$_{31}$ | H | H | H | CH$_3$ | H | 0 | CO | Glu(O$^t$Bu)$_2$ |
| 74 | COC$_{15}$H$_{31}$ | COC$_{15}$H$_{31}$ | H | H | H | CH$_3$ | H | 0 | CO | Glu(OH)$_2$ |
| 75 | COC$_{15}$H$_{31}$ | COC$_{15}$H$_{31}$ | H | H | H | CH$_3$ | H | 0 | CO | 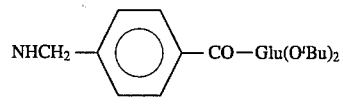 |

TABLE 8-continued

| Example Number | R¹ | R² | R³ | R⁴ | R⁵ | R⁶ | R⁷ | n | X | Y |
|---|---|---|---|---|---|---|---|---|---|---|
| 76 | $COC_{15}H_{31}$ | $COC_{15}H_{31}$ | H | H | H | $CH_3$ | H | 0 | CO | $-NHCH_2-\bigcirc-CO-Glu(OH)_2$ |

TABLE 9

| Example Number | R¹ | R² | R³ | R⁴ | R⁵ |
|---|---|---|---|---|---|
| 77 | $CO(CH_2)_{11}-\bigcirc$ | $CO(CH_2)_{11}-\bigcirc$ | H | H | H |
| 78 | $CO(CH_2)_{11}-\bigcirc$ | $CO(CH_2)_{11}-\bigcirc$ | H | H | H |
| 79 | $CO(CH_2)_{11}-\bigcirc$ | $CO(CH_2)_{11}-\bigcirc$ | H | H | H |
| 80 | $CO(CH_2)_{11}-\bigcirc$ | $CO(CH_2)_{11}-\bigcirc$ | H | H | H |
| 81 | $CONH(CH_2)_{11}-\bigcirc$ | $CONH(CH_2)_{11}-\bigcirc$ | H | H | H |
| 82 | $CONH(CH_2)_{11}-\bigcirc$ | $CONH(CH_2)_{11}-\bigcirc$ | H | H | H |
| 83 | $CONH(CH_2)_{11}-\bigcirc$ | $CONH(CH_2)_{11}-\bigcirc$ | H | H | H |
| 84 | $CONH(CH_2)_{11}-\bigcirc$ | $CONH(CH_2)_{11}-\bigcirc$ | H | H | H |
| 85 | $COC_{15}H_{31}$ | $COC_{15}H_{31}$ | H | H | $CH_3$ |
| 86 | $COC_{15}H_{31}$ | $COC_{15}H_{31}$ | H | H | $CH_3$ |
| 87 | $COC_{15}H_{31}$ | $COC_{15}H_{31}$ | H | H | H |

| Example Number | R⁶ | R⁷ | n | X | Y |
|---|---|---|---|---|---|
| 77 | H | H | 0 | CO | $-NH-\bigcirc-CO-Glu(O^tBu)_2$ |
| 78 | H | H | 0 | CO | $-NH-\bigcirc-CO-Glu(OH)_2$ |
| 79 | H | H | 0 | CO | $-NHCH_2-\bigcirc-CO-Glu(O^tBu)_2$ |

TABLE 9-continued

| | | R³ | R⁴ | n | X | Y |
|---|---|---|---|---|---|---|
| 80 | | H | H | 0 | CO | NHCH₂—⟨C₆H₄⟩—CO—Glu(OH)₂ |
| 81 | | H | H | 0 | CO | NH—⟨C₆H₄⟩—CO—Glu(O$^t$Bu)₂ |
| 82 | | H | H | 0 | CO | NH—⟨C₆H₄⟩—CO—Glu(OH)₂ |
| 83 | | H | H | 0 | CO | NHCH₂—⟨C₆H₄⟩—CO—Glu(O$^t$Bu)₂ |
| 84 | | H | H | 0 | CO | NHCH₂—⟨C₆H₄⟩—CO—Glu(OH)₂ |
| 85 | | H | H | 0 | CO | NH—⟨C₆H₄⟩—CO—Glu(O$^t$Bu)₂ |
| 86 | | H | H | 0 | CO | NH—⟨C₆H₄⟩—CO—Glu(OH)₂ |
| 87 | | H | H | 0 | CO | NH—⟨C₆H₄⟩—CO—Phe(OCH₃) |

TABLE 10

| Example Number | R¹ | R² | R³ | R⁴ | R⁵ | R⁶ | R⁷ | n | X | Y |
|---|---|---|---|---|---|---|---|---|---|---|
| 88 | COC₁₅H₃₁ | COC₁₅H₃₁ | H | H | H | H | H | 0 | CO | NH—⟨C₆H₄⟩—CO—Trp(OCH₃) |
| 89 | COC₁₅H₃₁ | COC₁₅H₃₁ | H | H | H | H | H | 0 | CO | NH—⟨C₆H₄⟩—CO—Phe(O$^t$Bu) |
| 90 | COC₁₅H₃₁ | COC₁₅H₃₁ | H | H | H | H | H | 0 | CO | NH—⟨C₆H₄⟩—CO—Phe(OH) |
| 91 | COC₁₅H₃₁ | COC₁₅H₃₁ | H | H | H | H | H | 0 | CO | NH—⟨C₆H₄⟩—CO—Met(O$^t$Bu)₂ |

TABLE 10-continued

| Example Number | R¹ | R² | R³ | R⁴ | R⁵ | R⁶ | R⁷ | n | X | Y |
|---|---|---|---|---|---|---|---|---|---|---|
| 92 | $COC_{15}H_{31}$ | $COC_{15}H_{31}$ | H | H | H | H | H | 0 | CO | NH—⟨◯⟩—CO—Met(OH) |
| 93 | $COC_{15}H_{31}$ | $COC_{15}H_{31}$ | H | H | H | H | H | 0 | CO | NH—⟨◯⟩—CO—Glu(O$^t$Bu)$_2$ |
| 94 | $COC_{15}H_{31}$ | $COC_{15}H_{31}$ | H | H | H | H | H | 0 | CO | NHCH$_2$—⟨◯⟩—CO—Glu(OH)$_2$ |
| 95 | $CO(CH_2)_{11}$—⟨◯⟩ | $CO(CH_2)_{11}$—⟨◯⟩ | H | H | H | H | H | 0 | CO | NH—⟨◯⟩—CO—Glu(O$^t$Bu)$_2$ |
| 96 | $CO(CH_2)_{11}$—⟨◯⟩ | $CO(CH_2)_{11}$—⟨◯⟩ | H | H | H | H | H | 0 | CO | NHCH$_2$—⟨◯⟩—CO—Glu(OH)$_2$ |
| 97 | $COC_{15}H_{31}$ | $COC_{15}H_{31}$ | H | Bond | H | H | H | 0 | CO | NHCH$_2$—⟨◯⟩—CO—Glu(O$^t$Bu)$_2$ |
| 98 | $COC_{15}H_{31}$ | $COC_{15}H_{31}$ | H | Bond | H | H | H | 0 | CO | NHCH$_2$—⟨◯⟩—CO—Glu(OH)$_2$ |

TEST EXAMPLE 1

Table 11 shows the mouse bone marrow cell growth promoting activities of compounds of the present invention. Each test compound was added at given concentrations to an RPMI medium (Bio-Wittaker Inc., USA) containing $2\times10^6$/ml BALB/c mouse bone marrow cells, 2 mM L-glutamine, 20/μg/gentamicin (Flow Laboratories, Scotland) and 10% fetal calf serum [Bio-Wittaker Inc., USA], followed by 8 days of incubation at 37° C. in 5% carbon dioxide gas, after which bone marrow cell growth was determined by the MTT reduction method [Tada et al., Journal of Immunological Methods, Vol. 93, p. 157 (1986)].

TABLE 11

Mouse Bone Marrow Cell Growth Promoting Action

| Test Compound | Minimum Effective Concentration (MEC, ng/ml)*¹ |
|---|---|
| Compound of Example 8 | 3.9 |
| Compound of Example 18 | 0.156 |
| Compound of Example 20 | 0.39 |
| Compound of Example 24 | 0.625 |
| Compound of Example 28 | 6.25 |
| Compound of Example 32 | 3.13 |
| Compound of Example 34 | 3.9 |
| Compound of Example 47 | 0.78 |
| Compound of Example 57 | 0.78 |
| Compound of Example 61 | 0.078 |
| Compound of Example 72 | 0.313 |

TABLE 11-continued

Mouse Bone Marrow Cell Growth Promoting Action

| Test Compound | Minimum Effective Concentration (MEC, ng/ml)*¹ |
|---|---|

*¹Minimum concentrations at which growth over 1.3 times that in the control group.

TEXT EXAMPLE 2

Table 12 shows the leukocyte increasing activities of compounds of the present invention.

To 6-week-old female CDF1/Crj mice (5 animals per group), cyclophosphamide in solution in physiological saline was orally administered at a dose of 150 mg/kg. Starting on the following day, each test compound in suspension in 5% glucose was subcutaneously administered once daily for 5 days at the doses shown below. On the day following final administration, an about 100/μl peripheral blood sample was taken via the orbital vein using an EDTA-treated glass capillary, and WBC counts were taken using an full-automatic multiple-parameter blood cell counter (Sysmex K-2000, Toa Medical Electronics Co., Ltd.).

TABLE 12

Leukocyte Increasing Activities

| Test Compound | Dose (mg/kg/day) | WBC Count (%)[*1] |
|---|---|---|
| Compound of Example 18 | 0.031 | 107 |
| Compound of Example 24 | 0.031 | 117 |

[*1]Percent ratios to the WBC count in mice receiving oral administration of physiological saline, in place of cyclophosphamide, at 0.2 ml/20 g body weight, followed by subcutaneous administration of the same dose of 5% glucose once daily for 5 days, starting on the following day. Cyclophosphamide was orally administered at a dose of 150 mg/kg. The mean WBC count and standard deviation in mice receiving subcutaneous administration of 5% glucose at 0.2 ml per 20 g body weight once daily for 5 days were 41 ± 11%, starting at one day following cyclophosphamide administration.

TEXT EXAMPLE 3

Table 13 shows the Ache (acetylcholine esterase) positive cell increasing activities of compounds of the present invention.

Ache activity was determined by the fluorometric method [Ishibashi et al., Proceedings of the National Academy of Sciences, USA, Vol. 86, pp. 5953– 5957 (1989)]. Specifically, non-adherent bone marrow cells of BALB/c mice were suspended to $1\times10^6$/ml in a Iscove's modified Dulbecco's medium (produced by Gibco BRL Inc., USA) containing 1% Neutridoma-SP (Boehringer Mannheim, Germany). This suspension was added to a 96-well flat based plate, previously dispensed with 25 μl of a solution of each inventive compound, at 100 μl per plate, followed by incubation at 37° C. in the presence of 5% $CO_2$ for 5 days. After completion of incubation, 25 μl of 6% glutaraldehyde was added, followed by 30 minutes of fixation at 4° C. This mixture was centrifuged at 850×g and 5° C. for 5 minutes; the supernatant was removed, followed by washing with 100 μl of phosphate-buffered saline (PBS). Then, to each well, 100 μl of buffer (pH 7.5) containing 0.2% polyoxyethylene-10-octylphenyl ether (abbreviated POPE), 1 mM EDTA, 0.12 M sodium chloride and 50 mM N-2-hydroxyethylpiperazine-N'-2ethanesulfonic acid (HEPES) was injected, and 10 μl of a 1.6 mg/ml solution of acetylthiocholine iodide was added to each well, followed by reaction at 33° C. for 3 hours. After completion of the reaction, each 10 μl was mixed with 10 μl of 0.4 mM 7-diethylamino-3-(4'-maleimidylphenyl)-4-methylcoumarin and 100 μl of a buffer (pH 5.0) containing 0.2% POPE, 1 mM EDTA and 50 mM sodium acetate, followed by determination of fluorescence intensity at an excitation wavelength of 365 nm and a fluorescence wavelength of 450 nm.

TABLE 13

AchE Positive Cell Increasing Action

| Test Compound | Concentration (ng/ml) | AchE Activity Increasing Rates[a)] |
|---|---|---|
| Compound of Example 22 | 1 | 2.07 |
| Compound of Example 24 | 1 | 2.02 |
| Compound of Example 26 | 1 | 2.09 |
| Compound of Example 40 | 1 | 1.67 |
| Compound of Example 51 | 1 | 1.88 |
| Compound of Example 72 | 1 | 2.23 |

[a)]Relative to the AchE activity in the control group

From the above results, it is evident that compound [I] or salt thereof of the present invention promotes megakaryocyte differentiation in mouse bone marrow cells; drugs containing it as an active ingredient are useful as therapeutic drugs for thrombocytopenia.

PREPARATION EXAMPLE 1

The following components, including the compound of Example 18, were kneaded and packed in gelatin capsules to yield capsules each containing 30 mg of the inventive compound.

| Compound of Example 18 | 30 mg |
|---|---|
| Lactose | 100 mg |
| Corn starch | 40 mg |
| Magnesium stearate | 10 mg |
| Total | 180 mg |

PREPARATION EXAMPLE 2

The compound of Example 18 and magnesium stearate were granulated using an aqueous solution of soluble starch, dried and then mixed with lactose and corn starch. The resulting mixture was subjected to compressive shaping to yield tablets of the following composition.

| Compound of Example 18 | 30 mg |
|---|---|
| Lactose | 65 mg |
| Corn starch | 30 mg |
| Soluble starch | 35 mg |
| Magnesium stearate | 20 mg |
| Total | 180 mg |

PREPARATION EXAMPLE 3

The compound of Example 18 was dissolved in saline containing 30% (w/v) polyethylene glycol 400 to yield a 0.05% solution of the inventive compound, which was then sterilized and filtered and dispensed to vials at 30 ml/vial to yield intravenous injections each containing 15 mg of the inventive compound per vial.

Compound [I] or salt thereof of the present invention possesses immunoenhancing activity and platelet reduction recovery activity, and can be used as a prophylactic/therapeutic agent for leukocytopenia in cancer chemotherapy or radiotherapy, as an immunoenhancing agent in bone marrow transplantation therapy and the treatment of osteomyelodysplasia and aplastic anemia, and as a prophylactic/therapeutic agent for thrombocytopenia.

What is claimed is:

1. A compound represented by the formula:

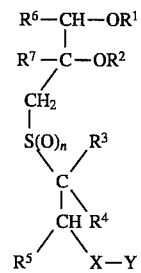

wherein $R^1$ and $R^2$ are the same or different, and each is an acyl group selected from the group consisting of an aliphatic acyl group having 6 to 26 carbon atoms and a substituted carbamoyl group; $R^3$, $R^6$ and $R^7$ are the same or different, and each is hydrogen or an alkyl group; $R^5$ is hydrogen, an alkyl group or a hydroxyl group which may optionally be protected, or $R^4$ and $R^5$ are combined to form a chemical bond; X is a carbonyl group or a sulfonyl group; Y is an amino acid sequence consisting of 1 to 7 amino acid residues which may optionally be protected and having optionally an intervening —$SO_2NH$— group; and n is an integer of 0 to 2, or a salt thereof.

2. The compound according to claim 1, wherein $R^1$ and $R^2$ are the same or different acyl group; $R^3$ and $R^4$ are the same or different hydrogen or an alkyl group; $R^5$, $R^6$ and $R^7$ are hydrogen, or $R^4$ and $R^5$ are combined to form a chemical bond; X is a carbonyl group or a sulfonyl group; Y is an amino acid sequence consisting of 1 to 7 amino acids residues which may optionally be protected and having optionally an intervening —$SO_2NH$—; and n is 0, or a salt thereof.

3. The compound according to claim 1, wherein the aliphatic acyl group has 10 to 20 carbon atoms.

4. The compound according to claim 1, wherein the substituent in the substituted carbamoyl group is an aliphatic hydrocarbon group having 4 to 24 carbon atoms.

5. The compound according to claim 1, wherein $R^3$ and $R^4$ are hydrogen.

6. The compound according to claim 1, wherein the amino acid sequence represented by Y consists of 1 to 5 amino acid residues.

7. The compound according to claim 1, wherein $R^5$ is hydrogen or an alkyl group having 1 to 4 carbon atoms.

8. The compound according to claim 1, wherein $R^6$ and $R^7$ are hydrogen.

9. The compound according to claim 1, wherein n is 0.

10. A compound according to claim 1, wherein the compound is 4-[6,7-bis( 12-phenyldodecanoyloxy)-4-thiaheptanoylaminomethyl]benzoyl-glutamic acid.

11. A compound according to claim 1, wherein the compound is 4-[6,7-bis(palmitoyloxy)- 4-thiaheptanoylamino] benzoyl-glutamic acid.

12. A compound according to claim 1, wherein the compound is 4-[6,7-bis( 12-phenyldodecanoyloxy)-4-thiaheptanoylamino]benzoyl-glutamic acid.

13. A compound according to claim 1, wherein the compound is 4-[6,7-bis(palmitoyloxy)- 4-thia-2(Z)-heptenoylaminomethyl]benzoyl-glutamic acid.

14. A compound according to claim 1, wherein the compound is 4-[6,7-bis(palmitoyloxy)- 2-methyl-4-thiaheptanoylamino]benzoyl-glutamic acid.

15. A compound according to claim 1, wherein the compound is 4-[6,7bis(palmitoyloxy)- 4-thiaheptanoylamino]benzoylphenylalanine.

16. A composition for immuno-enhancement, which comprises a compound or a salt thereof as claimed in claim 1 and an excipient.

17. A method for enhancing immunity in a mammal, which comprises administering an immunity-enhancing effective mount of the compound as claimed in .claim 1 or a pharmacologically acceptable salt thereof to the mammal.

18. A method for treating thrombocytopenia in a mammal, which comprises administering a thrombocytopenia-treating effective amount of the compound as claimed in claim 1 or a pharmacologically acceptable salt thereof to the mammal.

* * * * *